(12) United States Patent
Wichterle et al.

(10) Patent No.: US 8,969,081 B2
(45) Date of Patent: Mar. 3, 2015

(54) CAUDAL MOTOR NEURON DERIVED FROM EMBRYONIC STEM CELLS UNDER CONDITIONS ESSENTIALLY FREE OF ANY RETINOID

(75) Inventors: Hynek Wichterle, New York, NY (US); Thomas M. Jessell, Bronx, NY (US); Mirza Peljto, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 967 days.

(21) Appl. No.: 12/653,217

(22) Filed: Dec. 9, 2009

(65) Prior Publication Data

US 2010/0196332 A1    Aug. 5, 2010

Related U.S. Application Data

(60) Provisional application No. 61/201,491, filed on Dec. 10, 2008.

(51) Int. Cl.
| | |
|---|---|
| *C12N 5/02* | (2006.01) |
| *C12N 5/0793* | (2010.01) |
| C12N 5/074 | (2010.01) |
| C12N 5/0735 | (2010.01) |
| C12N 5/0797 | (2010.01) |
| A61K 35/30 | (2006.01) |

(52) U.S. Cl.
CPC ........ *C12N 5/0619* (2013.01); *C12N 2501/385* (2013.01); *C12N 5/0696* (2013.01); *C12N 5/0606* (2013.01); *C12N 2506/45* (2013.01); *C12N 5/0623* (2013.01); *C12N 2501/155* (2013.01); *C12N 2501/41* (2013.01); *A61K 35/30* (2013.01); *C12N 2501/115* (2013.01); *C12N 2501/13* (2013.01); *C12N 2501/19* (2013.01); *C12N 2506/02* (2013.01)
USPC ............................ 435/377; 435/384; 435/389

(58) Field of Classification Search
CPC .. A61K 35/30; C12N 5/0619; C12N 2506/02; C12N 2501/115; C12N 2501/385; C12N 5/0606; C12N 5/0696; C12N 5/0623; C12N 2501/13; C12N 2501/41; C12N 2506/45; C12N 2501/155
See application file for complete search history.

(56) References Cited

U.S. PATENT DOCUMENTS

| | | | |
|---|---|---|---|
| 5,753,506 | A | 5/1998 | Johe |
| 5,817,773 | A | 10/1998 | Wilson et al. |
| 5,844,079 | A | 12/1998 | Ingham et al. |
| 5,851,832 | A | 12/1998 | Weiss et al. |
| 5,980,885 | A | 11/1999 | Weiss et al. |
| 6,040,180 | A | 3/2000 | Johe |
| 6,277,820 | B1 | 8/2001 | Rosenthal et al. |
| 6,294,346 | B1 | 9/2001 | Weiss et al. |
| 6,432,711 | B1 | 8/2002 | Dinsmore et al. |
| 6,552,016 | B1 | 4/2003 | Baxter et al. |
| 6,613,798 | B1 | 9/2003 | Porter et al. |
| 6,646,113 | B1 | 11/2003 | Dreyfuss et al. |
| 6,683,108 | B1 | 1/2004 | Baxter et al. |
| 6,683,192 | B2 | 1/2004 | Baxter et al. |
| 6,833,269 | B2 | 12/2004 | Carpenter |
| 7,115,653 | B2 | 10/2006 | Baxter et al. |
| 7,250,294 | B2 | 7/2007 | Carpenter |
| 7,294,510 | B2 | 11/2007 | Okano et al. |
| 7,390,659 | B2 | 6/2008 | Jessell et al. |
| 7,632,679 | B2 | 12/2009 | Jessell et al. |
| 7,632,680 | B2 | 12/2009 | Neuman et al. |
| 2002/0009743 | A1 | 1/2002 | Carpenter |
| 2002/0151056 | A1 | 10/2002 | Sasai et al. |
| 2003/0068819 | A1 | 4/2003 | Zhang et al. |
| 2004/0023949 | A1 | 2/2004 | Baxter et al. |
| 2004/0224302 | A1 | 11/2004 | Jessell et al. |
| 2005/0014796 | A1 | 1/2005 | Baxter et al. |
| 2005/0019801 | A1 | 1/2005 | Rubin et al. |

(Continued)

FOREIGN PATENT DOCUMENTS

| | | |
|---|---|---|
| EP | 1500399 A1 | 1/2005 |
| WO | WO 2004/007665 | 1/2004 |

(Continued)

OTHER PUBLICATIONS

GIBCO™ Advanced Reduced Serum Media, Invitrogen Corporation, Carlsbad CA, Jul. 2004, pp. 1-2.*
U.S. Appl. No. 12/450,830, filed Apr. 10, 2008, Wichterle et al.
PCT International Preliminary Examination Report issued Jun. 13, 2005, in connection with PCT/US03/20399, filed on Jun. 26, 2003.
Written Opinion of International Searching Authority issued on Jun. 14, 2007 in connection with PCT/US05/05166, filed on Feb. 18, 2005.
PCT International Preliminary Report on Patentability issued on Jul. 10, 2007 in connection with PCT/US05/05166, filed on Feb. 18, 2005.

(Continued)

*Primary Examiner* — Deborah Crouch
(74) *Attorney, Agent, or Firm* — John P. White; Cooper & Dunham LLP

(57) ABSTRACT

Disclosed are methods for generating a neuron expressing Hoxc8 transcription factor or a caudal motor neuron comprising culturing an embryonic stem cell in a composition which is essentially free of retinoids and comprises an isotonic salt solution, so as to generate the neuron which expresses Hoxc8 transcription factor or the caudal motor neuron. Disclosed are also methods for generating a caudal brachial motor neuron, a thoracic motor neuron, or a lumbar motor neuron from an embryonic stem cell in a composition essentially free of retinoids and comprising ADFNK medium, an amount of FGF-2, or Gdf11 respectively. Disclosed are also methods of transplanting a motor neuron into a subject comprising generating the motor neuron and transplanting the motor neuron into the subject. Disclosed is also a population of motor neuron cells enriched for motor neuron cells expressing Foxp1 and expressing a gene associated with Spinal Muscular Atrophy (SMA) or Amyotrophic Lateral Sclerosis (ALS).

18 Claims, 34 Drawing Sheets

(56) References Cited

U.S. PATENT DOCUMENTS

| | | | |
|---|---|---|---|
| 2005/0080138 | A1 | 4/2005 | Guicherit et al. |
| 2005/0203014 | A1 | 9/2005 | Rubin |
| 2005/0266555 | A1 | 12/2005 | Lu et al. |
| 2006/0275290 | A1 | 12/2006 | Barbeito et al. |
| 2006/0281179 | A1 | 12/2006 | Sasai et al. |
| 2007/0185024 | A1 | 8/2007 | Jessell et al. |
| 2007/0224650 | A1 | 9/2007 | Jessell et al. |

FOREIGN PATENT DOCUMENTS

| | | |
|---|---|---|
| WO | WO 2005/081857 | 9/2005 |
| WO | WO 2005/082002 | 9/2005 |
| WO | WO 2008/127974 | 10/2008 |

OTHER PUBLICATIONS

Written Opinion of International Searching Authority issued on Jun. 26, 2007 in connection with PCT/US05/005877, filed on Feb. 22, 2005.
PCT International Preliminary Report on Patentability issued on Jul. 17, 2007 in connection with PCT/US05/005877, filed on Feb. 22, 2005.
PCT International Preliminary Report on Patentability issued on Oct. 13, 2009 in connection with PCT/US08/59883, filed on Apr. 10, 2008.
Written Opinion of International Searching Authority issued on Jun. 30, 2008 in connection with PCT/US08/59883, filed on Apr. 10, 2008.
Supplementary European Search Report issued on Jun. 19, 2009 in connection with European Application No. 05723654.9.
Nov. 19, 2007 Office Action issued from the Australian Patent and Trademark Office in connection with application No. AU2003247809.
Oct. 1, 2004 Office Action issued from the U.S. Patent and Trademark Office in connection with U.S. Appl. No. 10/196,882.
Jul. 19, 2004 Office Action issued from the U.S. Patent and Trademark Office in connection with U.S. Appl. No. 10/196,882.
May 3, 2005 Office Action issued from the U.S. Patent and Trademark Office in connection with U.S. Appl. No. 10/196,882.
Feb. 22, 2006 Office Action issued from the U.S. Patent and Trademark Office in connection with U.S. Appl. No. 10/196,882.
Oct. 27, 2006 Final Office Action issued from the U.S. Patent and Trademark Office in connection with U.S. Appl. No. 10/196,882.
Jun. 22, 2007 Office Action issued from the U.S. Patent and Trademark Office in connection with U.S. Appl. No. 10/196,882.
Aug. 14, 2006 Office Action issued from the U.S. Patent and Trademark Office in connection with U.S. Appl. No. 10/789,266.
Apr. 30, 2007 Office Action issued from the U.S. Patent and Trademark Office in connection with U.S. Appl. No. 10/789,266.
May 15, 2007 Office Action issued from the U.S. Patent and Trademark Office in connection with U.S. Appl. No. 10/789,308.
Jan. 16, 2008 Final Office issued from the U.S. Patent and Trademark Office in connection with U.S. Appl. No. 10/789,308.
Apr. 9, 2008 Advisory Action issued from the U.S. Patent and Trademark Office in connection with U.S. Appl. No. 10/789,308.
Oct. 3, 2008 Office Action issued from the U.S. Patent and Trademark Office in connection with U.S. Appl. No. 10/789,308.
May 29, 2009 Notice of Allowability issued from the U.S. Patent and Trademark Office in connection with U.S. Appl. No. 10/789,308.
Jul. 24, 2009 Notice of Allowability issued from the U.S. Patent and Trademark Office in connection with U.S. Appl. No. 10/789,308.
Apr. 30, 2008 Office Action issued from the U.S. Patent and Trademark Office in connection with U.S. Appl. No. 11/510,038.
Dec. 12, 2008 Office Action issued from the U.S. Patent and Trademark Office in connection with U.S. Appl. No. 11/510,038.
May 9, 2008 Office Action issued from the U.S. Patent and Trademark Office in connection with U.S. Appl. No. 11/510,366.
Dec. 17, 2008 Office Action from the U.S. Patent and Trademark Office issued in connection with U.S. Appl. No. 11/510,366.
Nov. 19, 2009 Office Action issued from the U.S. Patent and Trademark Office in connection with U.S. Appl. No. 11/510,038.
Oct. 2, 2009 Office Action issued from the U.S. Patent and Trademark Office in connection with U.S. Appl. No. 11/510,366.
Jan. 3, 2005 Response to Oct. 1, 2004 Office Action issued in connection with U.S. Appl. No. 10/196,882.
Nov. 3, 2005 Amendment in Response to May 3, 2005 Office Action issued in connection with U.S. Appl. No. 10/196,882.
Jul. 24, 2006 Amendment in Response to Feb. 22, 2006 Office Action issued in connection with U.S. Appl. No. 10/196,882.
Apr. 27, 2007 Amendment in Response to Oct. 27, 2006 Office Action issued in connection with U.S. Appl. No. 10/196,882.
Nov. 21, 2007 Amendment in Response to Jun. 22, 2007 Office Action issued in connection with U.S. Appl. No. 10/196,882.
Sep. 3, 2008 Communication in Response to May 9, 2008 Office Action issued in connection with U.S. Appl. No. 11/510,366.
May 18, 2009 Amendment in Response to Dec. 17, 2008 Office Action issued in connection with U.S. Appl. No. 11/510,366.
Mar. 2, 2010 Amendment in Response to Oct. 2, 2009 Office Action issued in connection with U.S. Appl. No. 11/510,366.
Nov. 14, 2007 Response to May 15, 2007 Office Action issued in connection with U.S. Appl. No. 10/789,308.
Feb. 27, 2008 Response to Jan. 16, 2008 Final Office Action issued in connection with U.S. Appl. No. 10/789,308.
Jan. 5, 2009 Communication in Response to Oct. 3, 2008 Office Action issued in connection with U.S. Appl. No. 10/789,308.
Sep. 2, 2008 Communication in Response to Apr. 30, 2008 Office Action issued in connection with U.S. Appl. No. 11/510,038.
May 12, 2009 Amendment in Response to Dec. 12, 2008 Office Action issued in connection with U.S. Appl. No. 11/510,038.
Bain, G, et al. (1995) "Embryonic stem cells express neuronal properties in vitro." Dev Biol. 168:342-357.
Briscoe, J, et al. (2001) "Specification of neuronal fates in the ventral neural tube." Curr. Opin. Neurobiol. 11:43-49.
Briscoe, J, et al. (2000) "A homeodomain protein code specifies progenitor cell identity and neuronal fate in the ventral neural tube." Cell. 101:435-445.
Gage, FH. (2000) "Mammalian neural stem cells." Science. 287: 1433-1438.
Harper JM, et al. (2004) "Axonal growth of embryonic stem cell-derived motoneurons in vitro and in motoneuron-injured adult rats." Proc Natl Acad Sci USA. 101:7123-7128.
Hollyday, M. (1980) "Motoneuron histogenesis and the development of limb innervations." Curr Top Dev Biol. 15(1):181-215.
Hollyday, M. (1980) "Organization of motor pools in the chick lumbar lateral motor column." J Comp Neurol. 194:143-70.
Hollyday, M., et al. (1990) "Location of motor pools innervating chick wing." J Comp Neurol. 302:575-588.
Jessell, TM. (2000) "Neuronal specification in the spinal cord: inductive signals and transcriptional codes." Nat Rev Genet. 1:20-29.
Kawasaki, H, et al. (2000) "Induction of midbrain dopaminergic neurons from ES cells by stromal cell-derived inducing activity." Neuron. 28:31-40.
Lee, SK, et al. (2001) "Transcriptional networks regulating neuronal identity in the developing spinal cord." Nat Neurosci 4 Suppl. 1183-1191.
Lee, H, et al. (Aug. 2007) "Directed differentiation and transplantation of human embryonic stem cell-derived motorneurons." Stem Cells. 8:1931-9.
Li XJ, et al. (2005) "Specification of motorneurons from human embryonic stem cells." Nat. Biotechnol. 23(2):215-21.
Li XJ, et al. (Jan. 2008) "Directed Differentiation of Ventral Spinal Progenitors . . . Small Molecules." Stem Cells. 26(4):886-93.
Lim UM, et al. (Nov. 2006) "Derivation of Motor Neurons from three Clonal Human Embryonic Stem Cell Lines." Curr Neurovasc Res. 3(4):281-8.
Miles GB, et al. (2004) "Functional properties of motoneurons derived from mouse embryonic stem cells." J Neurosci. 24:7848-7858.
Mizuguchi, R, et al. (2001) "Combinatorial roles of olig2 and neurogenin2 . . . motoneurons." Neuron. 31:757-771.
Mizuseki, K, (May 2003) "Generation of neural crest-derived peripheral neurons . . . stem cells." Proc Natl Acad Sci USA. 100(100):5828-33.

(56) References Cited

OTHER PUBLICATIONS

Muhr, J, et al. (1999) "Convergent inductive signal specify midbrain, hindbrain, and spinal cord identity in gastrula stage chick embryos." Neuron. 23:689-702.
Munoz-Sanjuan, I, et al. (2002) "Neural induction, the default model and embryonic stem cells." Nat Rev Neurosci. 3:271-280.
Novitch, BG, et al. (2003) "A requirement for retinoic acid-mediated transcriptional activation in ventral neural patterning and motor neuron specification." Neuron. 40:81-95.
Renoncourt, Y, et al. (1998) "Neurons derived in vitro from ES cells express homeoproteins characteristic of motoneurons and interneurons." Mech Dev. 79:185-197.
Shin et al., (2005) "Human Motor Neuron Differentiation from Human Embryonic Stem Cells." Stem Cells and Development. 14:1-4.
Soundararajan, et al. (2007) "Easy and Rapid Differentiation of Embryonic Stem Cells . . . Sonic Hedgehog Producing Cells." Stem Cells. 25(7):1697-1707.
Tropepe, V, et al. (2001) "Direct neural fate specification from embryonic stem cells . . . default mechanism." Neuron. 30:65-78.
Uchida, N, et al. (2000) "Direct isolation of human central nervous system stem cells." Proc Natl Acad Sci USA. 97:14720-14725.
Wichterle, H, et al. (2002) "Directed differentiation of embryonic stem cells into motor neurons." Cell. 110:385-397.
Wichterle, H, et al. (2008) "Differentiation of mouse embryonic stem cells to spinal motor neurons." In Current Protocols in Stem Cell Biology. Chapter 1:Unit 1H.1.1-1H.1.9.
Wichterle, H, et al. (2009) "Xenotransplantation of Embryonic Stem Cell-Derived . . . Spinal Cord." In Stem Cells in Regenerative Medicine. 171-183.
Zhou, Q, et al. (2002) "The bHLH transcription factors OLIG2 and LIG1 couple neuronal and glial subtype specification." Cell. 109: 61-73.
Carpenter et al. (2001) "Enrichment of neurons and neural precursors from human embryonic stem cells", Experimental Neurology, 172(2):383-397.
Castelo-Branco et al. (2003) "Differential regulation of midbrain dopaminergic neuron development by Wnt-1, Wnt-3a, and Wnt5a", PNAS, 100(22):12747-12752.
Dann et al. (2001) "Insights into Wnt binding and signaling from the structures of two Frizzeled cysteine-rich domains" Nature, 412:86-90.
Kawasaki et al. (2000) "Induction of midbrain dopaminergic neurons from ES cells by stromal cell-derived inducing activity", Neuron, 28:31-40.
Muroyama et al. (2004) "Want proteins promote neuronal differentiation in neural stem cell culture", Biochemical and biophysical Research Communications, 313:915-921.
Shin et al, (2007) "Stage-Dependent lig2 Expression in Motor Neurons and Oligodendrocytes Differentiated from Embryonic Stem Cells", Stem Cells and Development, 16:131-141.
Jul. 7, 2010 Final Office Action issued in connection with U.S. Appl. No. 11/510,038, filed Aug. 25, 2006.
Dec. 8, 2010 Office Action issued in connection with U.S. Appl. No. 11/510,038, filed Aug. 25, 2006.
Nov. 25, 2009 Communication Pursuant to Article 94(3) EPC issued in connection with European Application No. 03764327.7.
Oct. 7, 2010 Amendment Under 37 C.F.R. 1.116 in Response to Jul. 7, 2010 Final Office Action issued in connection with U.S. Appl. No. 11/510,038, filed Aug. 25, 2006.
Jun. 7, 2010 Response to Nov. 25, 2009 Communication Pursuant to Article 94(3) EPC issued in connection with European Application No. 03764327.7.
Jan. 4, 2013 Office Action issued in connection with U.S. Appl. No. 12/450,830, §371 national stage of PCT International Application No. PCT/US2008/059883.
Jul. 25, 2013 Final Office Action issued in connection with U.S. Appl. No. 12/450,830, §371 national stage of PCT International Application No. PCT/US2008/059883.
May 6, 2013 Amendment in Response to Jan. 4, 2013 Office Action issued in connection with U.S. Appl. No. 12/450,830.

\* cited by examiner

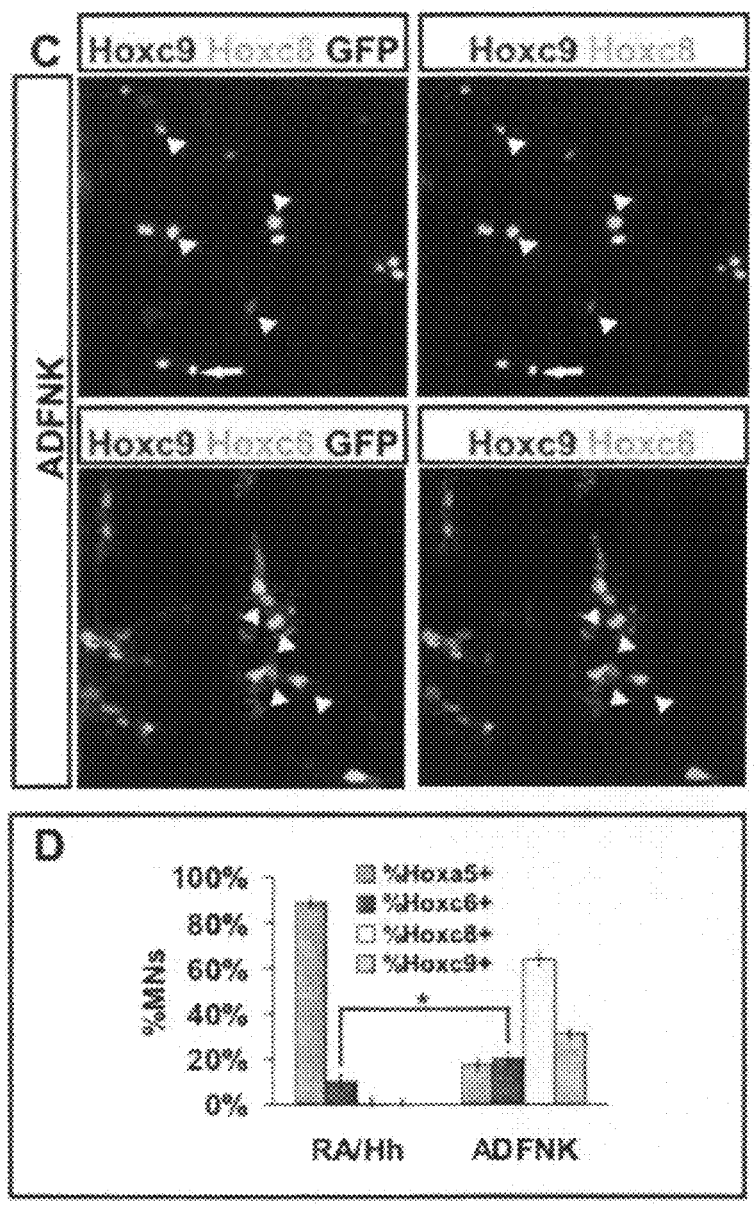

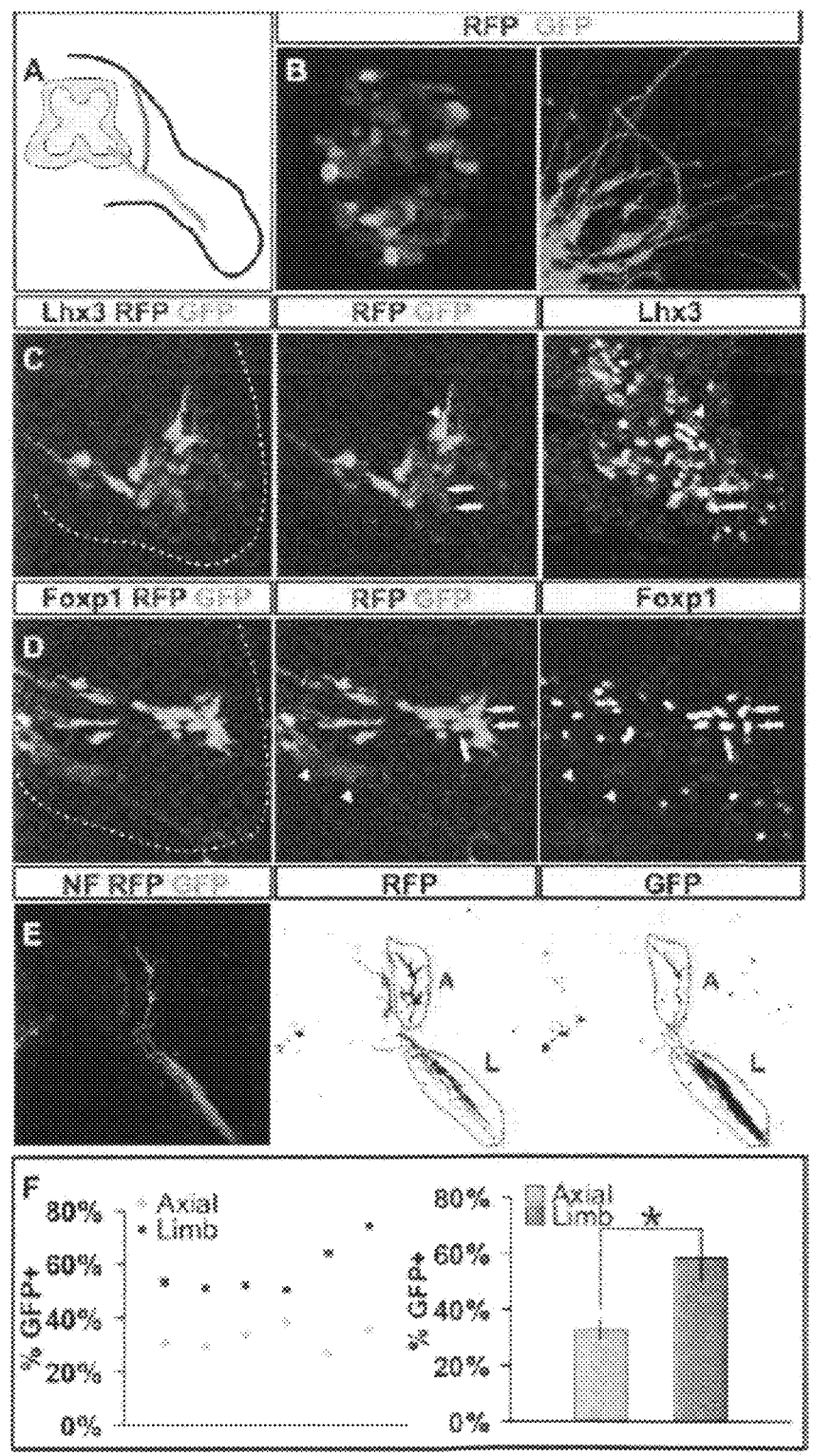

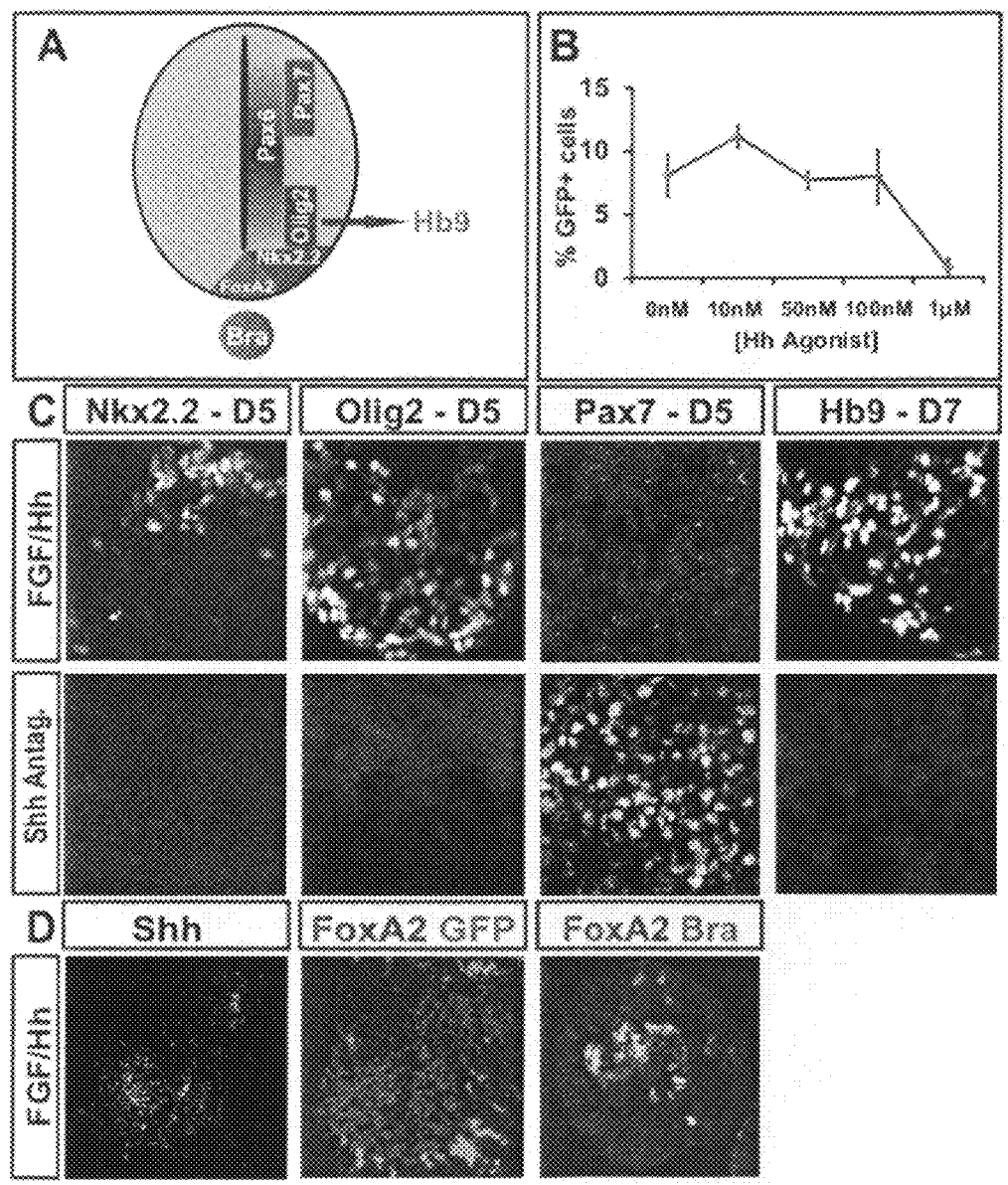

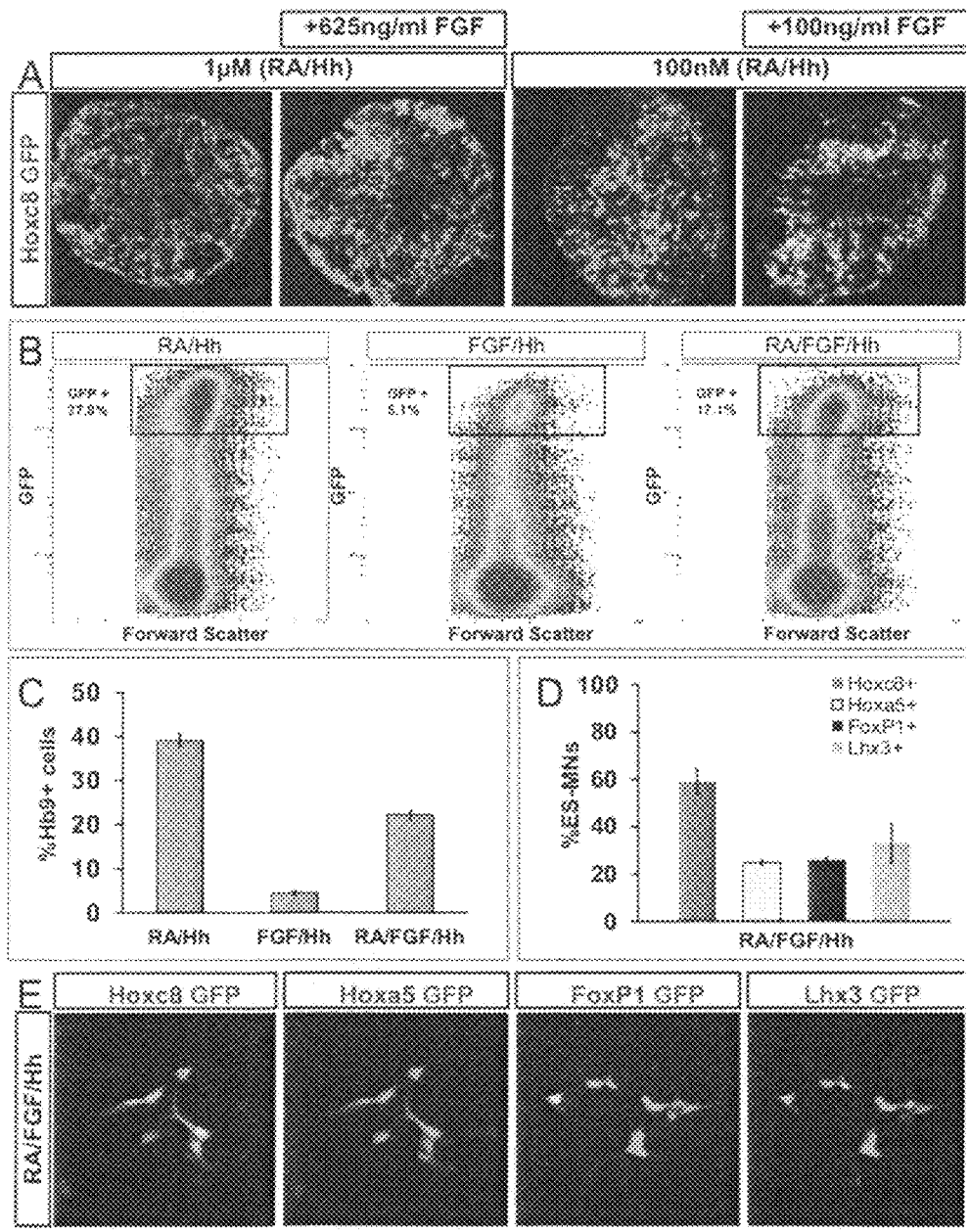

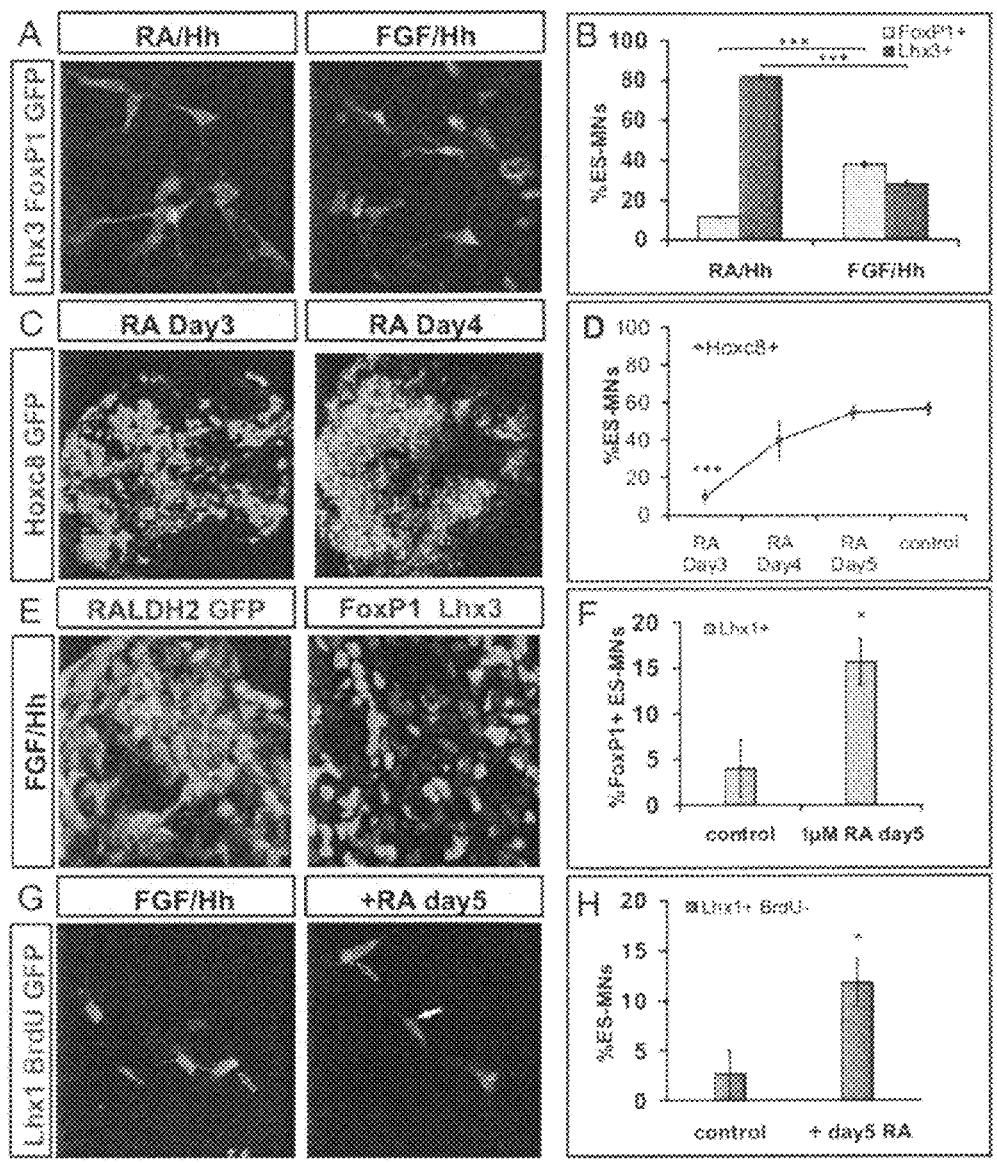

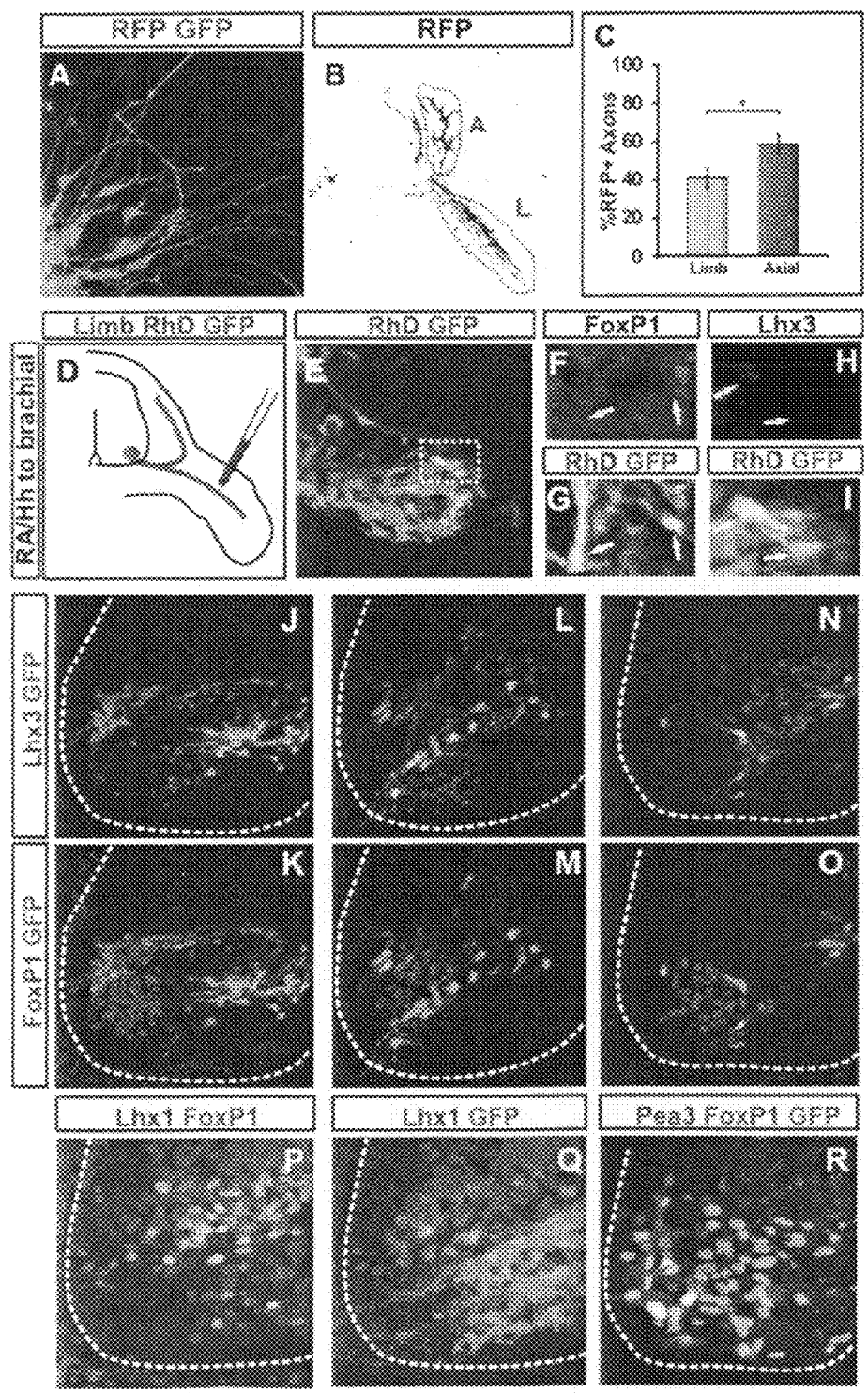

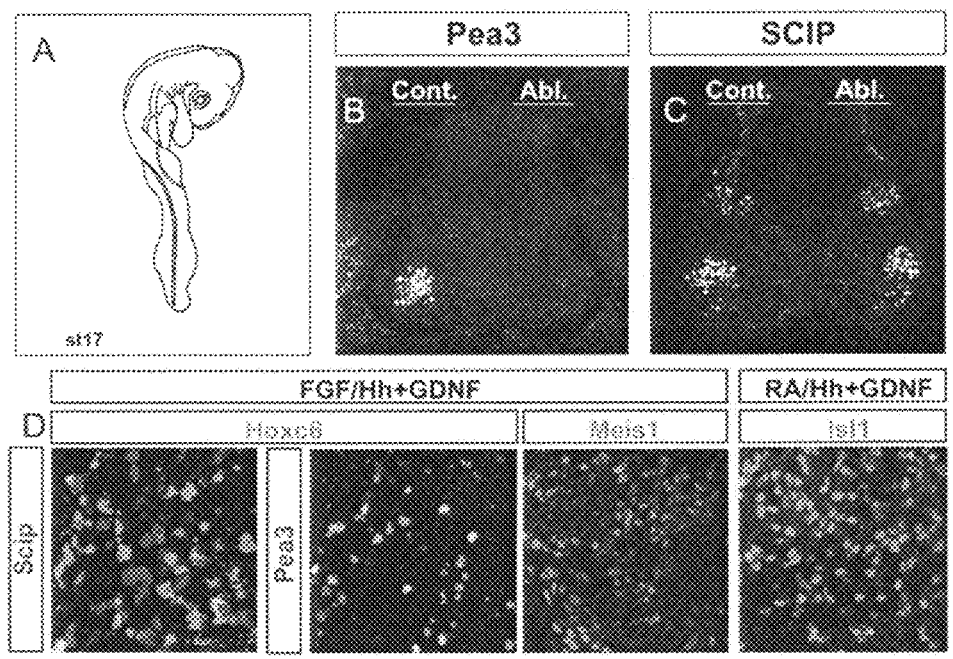

CAUDAL MOTOR NEURON DERIVED FROM EMBRYONIC STEM CELLS UNDER CONDITIONS ESSENTIALLY FREE OF ANY RETINOID

This invention was made with government support under grant numbers 1R01NS058502-01 and HD055165 awarded by the National Institutes of Health (NIH). The government has certain rights in the invention.

This application claims the benefit of U.S. Provisional Application No. 61/201,491, filed Dec. 10, 2008.

Throughout this application, various publications are referred to by first author and year of publication. Full citations for these publications are presented in a References section immediately before the claims. Disclosures of the publications cited in the References section in their entireties are hereby incorporated by reference into this application in order to more fully describe the state of the art as of the date of the invention described herein.

BACKGROUND

During the development of the vertebrate central nervous system (CNS), hundreds of distinct neuronal types are generated, establishing a diversity that is essential for the formation of neuronal circuits. The degeneration of specific classes of CNS neurons is the hallmark of many neurological disorders, a realization that has prompted interest in defining proliferative cell populations that could serve as replenishable sources of neurons for the treatment of neurodegenerative diseases. Studies by a number of different groups have provided evidence that murine embryonic stem cells can be directed along specific pathways of neuronal differentiation in a systematic manner (Bain et al., 1995; Kawasaki et al., 2000; Munoz-Sanjuan 35 al., 2002; Tropepe et al., 2001; Uchida et al., 2000), raising the possibility that such stem cell-derived neurons could have clinical utility (Gage, 2000).

Generation of neuronal diversity during the vertebrate CNS development involves multiple steps, beginning with neural induction and patterning of the neural plate into broad anteroposterior domains: the prospective forebrain, midbrain, hindbrain and spinal cord (Muhr et al., 1999) Subsequently, neuroepithlial cells within each domain are patterned along dorso-ventral (DV) and antero-posterior (AP) axes to establish the principal fate map for future neurons.

Spinal motor neurons represent the class of CNS neuron that is perhaps best understood, both in the context of their mature function, and their developmental origins (Hollyday, 1980; Jessell, 2000; Lee and Pfaff, 2001). The DV patterning of the spinal cord leads to specification of ~15 distinct classes of neurons, including the ventral MNs. Generic MN identity is established by the joint actions of two extrinsic signals: a long range gradient of Sonic hedgehog (Shh) activity provided by the notochord and floor plate, and a more diffuse influence of retinoid signals provided by the paraxial mesoderm (Briscoe and Ericson, 2001; Briscoe et al., 2000; Novitch et al., 2003).

Cells in the developing neural tube interpret these two signals by expressing a set of homeodomain proteins that define five principal progenitor domains within the ventral half of the spinal cord (Jessell, 2000; Lee and Pfaff, 2001). One of these—the pMN domain—which is marked by the expression of homeodomain transcription factor Nkx6.1 and basic helix-loop-helix (bHLH) transcription factor Olig2 is the sole source of motor neuron progenitors (Briscoe et al., 2000; Mizuguchi et al., 2001; Novitch et al., 2001; Zhou and Anderson, 2002). Expression of Olig2 within MN progenitors leads to the induction of pro-neural gene Neurogenin 2 (Ngn2) that governs cell cycle exit, acquisition of pan-neuronal identity, and induction of a set of transcription factors (Hb9, Lhx3 and Isl1) transiently expressed in all nascent spinal MNs, thus specifying generic motor neuron identity (Briscoe and Ericson, 2001).

With this information about the normal pathway of motor neuron generation, it has become possible to examine whether embryonic stem (ES) cells can respond to the same extrinsic signals to generation post-mitotic motor neurons through the same molecular pathway. Studies over the past few years have revealed that mouse ES cells can indeed generate spinal motor neurons at high efficiency, and that the pathway of motor neuron (MN) generation from ES cells recapitulates the steps of motor neuron generation in vivo. (Renoncourt et al., 1998; Wichterle et al., 200). ES cell-derived MNs in vitro acquire electrophysiological properties that resemble their embryo-derived counterparts, they develop appropriate ionic currents in response to neurotransmitters, they can receive synaptic inputs and fire repetitively at rates sufficient for functional muscle contract and they form functional synapses with cultured muscle cells (Miles et al., 2004).

Moreover, ES cell-derived MNs can repopulate the embryonic and adult spinal cord in vivo (Wichterle et al., 2002). In an embryonic environment ES cell MNs can extend axons into the periphery and form synapses with muscle targets (Wichterle et al., 2002). In an embryonic environment ES cell MNs can extend axons into the periphery and form synapses with muscle targets (Wichterle et al., 2002). In an adult environment, in which MNs degenerate, some limited axon extension out of the spinal cord is observed under pharmacological conditions that promote axonal regeneration (Harper et al., 2004). Together, these studies have indicated the feasibility of applying insights into normal developmental signaling cascades, in particular the control of extracellular inductive signals, to direct the differentiation of ES cells into spinal MNs. The potential for ES cell-derived MNs to innervate target muscle cells thus opens the way for a systematic evaluation of the use of such neuron to restore motor function, initially in mammalian models of spinal cord injury and motor neuron degenerative diseases.

There are, however, challenges in the basic study of cell differentiation into MNs which remain unaddressed.

All the studies performed on ES cell differentiation into MNs have assessed simply a set of generic motor neuron properties (Wichterle et al., 2002). Yet in the intact spinal cord, there are approximately one hundred different classes of MNs, each acquiring subtype specializations that are critical for the effective innervations of their cognate muscle and neuronal targets. Given the extensive evidence for MN specialization in situ, it remains unclear whether ES cells-derived MNs are capable of acquiring these highly specialized MN subtype characters. This is in part due to limited understanding of developmental processes and transcriptional programs controlling neuronal subtype diversification and in part due to technically demanding analysis of neuronal migratory and axon pathfinding properties by transplantation into the developing mammalian embryo.

At this point, no systematic effort has been made to regulate MN subtype identity in a developmentally sensible manner. Moreover, due to the state of knowledge of brachial Motor Neurons (bMNs) in comparison to cervical spinal motor neurons, methods for directed differentiation of ES cells into brachial spinal motor neuron and other more caudal motor neurons in vitro which can produce MNs that can acquire similarly complex and specialized subtype phenotypes as MN generated in the same section of the spinal cord in vivo needs to be investigated.

SUMMARY OF INVENTION

The subject invention provides a method for generating a caudal motor neuron comprising culturing an embryonic stem cell in a composition which is essentially free of retinoids and comprises an isotonic salt solution, so as to generate the caudal motor neuron.

The subject invention also provides a method of generating a neuron expressing Hoxc8, comprising culturing an embryonic stem cell in a composition which is essentially free of retinoids and comprises an isotonic salt solution, so as to generate the neuron which expresses Hoxc8 transcription factor.

The subject invention also provides a method for generating a caudal brachial motor neuron from an embryonic stem cell, comprising culturing the embryonic stem cell in a composition essentially free of retinioids and comprising an amount of Advanced Dulbecco's Modified Eagle's Medium/F12 and Neurobasal medium that has been supplemented with 10% Knockout-Serum Replacement (ADFNK medium) effective to produce the caudal brachial motor neuron.

The subject invention also provides a method of transplanting a motor neuron into a subject comprising: a) generating a motor neuron by culturing an embryonic stem cell in a composition essentially free of retinoids and comprising an isotonic salt solution, so as to generate the motor neuron; and b) transplanting the motor neuron into the subject.

The subject invention also provides a method for generating a thoracic motor neuron from an embryonic stem cell comprising contacting the embryonic stem cell with a composition essentially free of retinoids and comprising an amount of Fibroblast Growth Factor-2 (FGF-2) effective to produce the thoracic motor neuron.

The subject invention also provides a method of transplanting a thoracic motor neuron into a subject comprising: a) generating a motor neuron by culturing an embryonic stem cell in a composition essentially free of retinoids and comprising an isotonic salt solution, so as to generate the motor neuron; b) administering Fibroblast Growth Factor-2 (FGF-2) to the generated motor neuron so as to generate the thoracic motor neuron; and c) transplanting the thoracic motor neuron into the subject.

The subject invention also provides a method for generating a lumbar motor neuron from an embryonic stem cell comprising contacting the embryonic stem cell with a composition essentially free of retinoids and comprising an amount of Growth differentiation factor 11 (Gdf11) effective to produce the lumbar motor neuron.

The subject invention also provides a method of transplanting a lumbar motor neuron into a subject comprising: a) generating a motor neuron by culturing an embryonic stem cell in a composition essentially free of retinoids and comprising an isotonic salt solution, so as to generate the motor neuron; b) administering Growth differentiation factor 11 (Gdf11) to the generated motor neuron so as to generate the lumbar motor neuron; and c) transplanting the lumbar motor neuron into the subject.

The subject invention also provides a population of motor neuron cells enriched for motor neuron cells expressing Foxp1 and expressing a gene associated with Spinal Muscular Atrophy (SMA) or Amyotrophic Lateral Sclerosis (ALS).

BRIEF DESCRIPTION OF THE DRAWINGS

FIG. 3: FIGS. 3A-D show the expression profiles of Hox proteins in ES cell-derived MNs.

FIG. 4: FIGS. 4A and 4B show Hb9-RFP ES cells differentiated to cervical MNs in the presence of Retinoic Acid (RA) and Hedgehog (Hh) were mixed with Hb9-GFP brachial MNs differentiated in ADFNK medium and transplanted into the chick brachial neural tube. FIGS. 4C and 4D show transplanted cells maintained their columnar identity in vivo, with a majority of RFP+ cervical MNs expressing MMC marker Lhx3 and a significant fraction of FGP+ brachial MNs expressing LMC marker Foxp1. FIG. 4E shows axon pathfinding preference of RFP+ and GFP+ MNs as quantified by measuring red (dark gray) and green (light gray) fluorescence intensities in axial and limb branches of motor neurons. FIG. 4F shows cervical (RFP+) and brachial (GFP+) motor axons consistently exhibit distinct pathfinding preference at the axial nerve branch point.

FIG. 5: shows Hb9-GFP ES cells differentiated into brachial MNs and transplanted into the brachial spinal cord were retrogradely labeled with rhodamine-dextran (RhD) either from the axial or limb motor nerve branch.

FIG. 6: shows caudal brachial MMC MNs acquire properties of cutaneous maximus (CM) and flexor carpii ulnaris (FCU) motor pools. FIGS. 6B and 6D show that, consistent with in vivo observation, supplementing ES cell-derived caudal brachial MNs on Day 5 of differentiation with 10 ng/ml of GDNF resulted in a robust induction of Pea3 expression in a subset (~20%) of LMC MNs. FIG. 6D show that in the absence of exogenous GDNF, brachial MNs that would normally express Pea3 are not re-specified into Scip+ MNs as the percentage of Scip+ MNs in the presence or absence of GDNF is not significantly different. FIG. 6E shows that nearly 90% of Pea3+ MNs expressed Isl1+ while less than 10% express Lhx1. FIG. 6D and FIGS. 6F-G show that while Scip expression is not dependent on GDNF signaling it is expressed in a mutually exclusive manner with Pea3.

Figure 1:
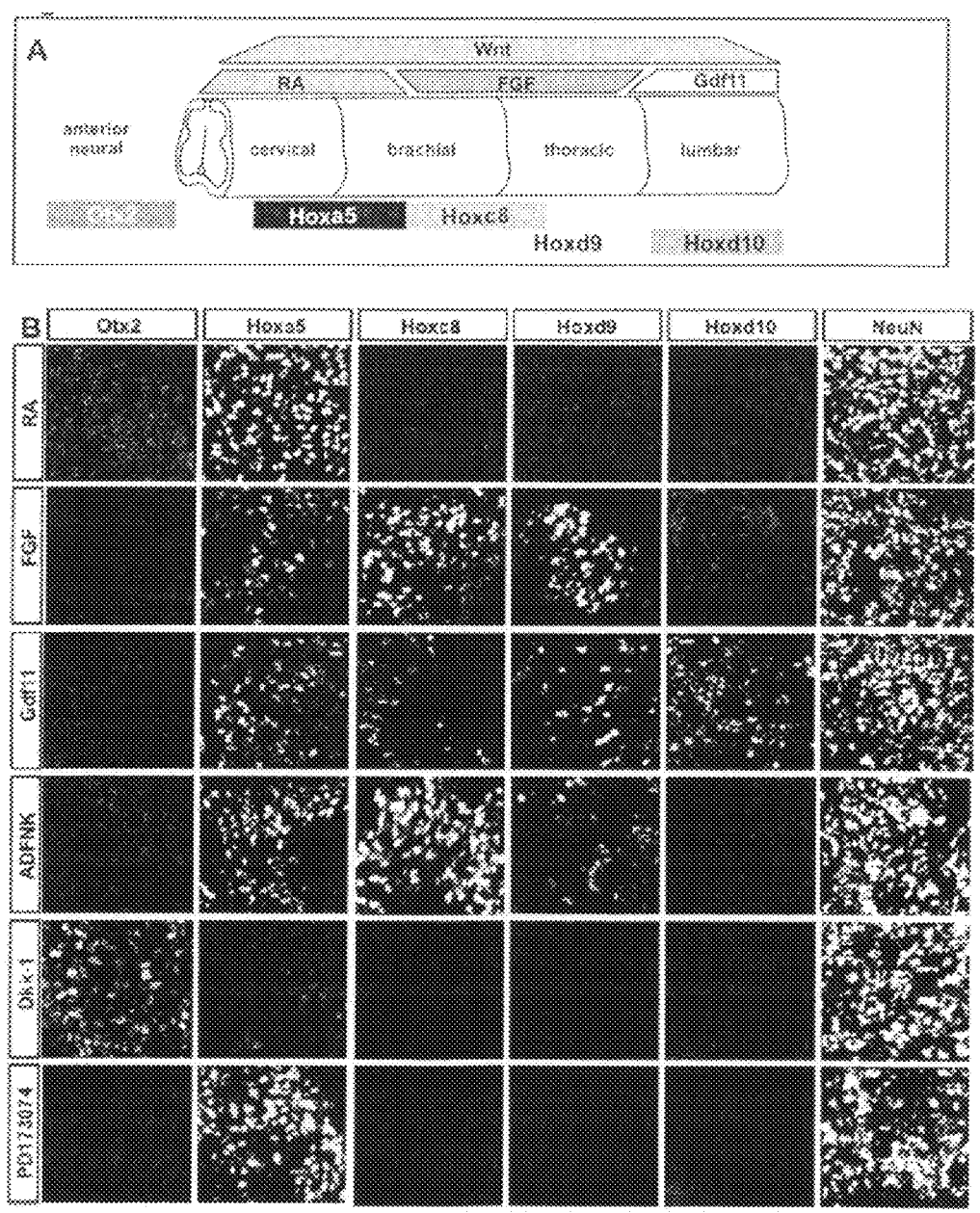
FIG. 1: shows the rostro-caudal patterning of differentiated ES cells in response to various developmentally relevant signals.

FIG. 23: Endogenous Shh Signal Controls Ventralization of Spinal Progenitors: A) Schematic of Shh signaling and specification of dorso-ventral progenitor domains in the developing spinal cord. Shh signal secreted from the floor plate and notochord patterns ventral spinal cord and specifies Olig2$^+$ MN progenitor identity. B) To test if Shh signaling is the limiting factor in the efficiency of ES-MN generation in the absence of extrinsic factors, ES cells were differentiated in the presence of increasing concentration of Hh agonist (10 nM, 50 nM, 100 nM, and 1 µM Hh agonist were supplemented on day 2 of differentiation). The resulting EBs were dissociated on day 7 of differentiation and the number of Hb9-GFP expressing and total cells was determined. Addition of increasing concentrations of Hh agonist does not significantly change the percentage of Hb9-GFP$^+$ cells obtained during differentiation suggesting that Shh signaling is not the limiting factor during differentiation. Graphed are results from three independent differentiation experiments (mean±SEM). C) To test if the induction of ES-MNs in the absence of exogenous signals depends on Shh generated by the EBs during differentiation, EBs differentiated in FGF/Hh conditions were treated with 100 nM Shh antagonist on day 2 of differentiation and the expression of Pax7, Olig2, Nkx2.2 (on day 5), and Hb9 (on day 7) was examined. Inhibition of endogenous Shh signaling by addition of Shh antagonist resulted in the loss of Nkx2.2 and Olig2 expression and failure of MN differentiation (lack of Hb9$^+$ cells). When treated with Shh antagonist, the majority of cells acquired expression of dorsal spinal progenitor marker Pax7. These results suggest that ES-MN differentiation in the absence of exogenous factors is dependent on Shh signaling induced in differentiating EBs. D) To determine the sources of Shh signaling in the EBs, immunohistochemistry was performed again using antibodies against Shh, FoxA2 and Bra. on day 5 of differentiation. Endogenous signaling centers express floor-plate/notochord marker FoxA2 and Shh on day 5 of differentiation. A subset of FoxA2 cells co-expressed notochord marker Brachyury. These results indicate that notochord and floor-plate like cells express Shh signal in the differentiating EBs, required for the ventralization of MN progenitors and specification of ES-MNs in the absence of added extrinsic factors.

FIG. 24: Rostro-caudal Patterning of ES-MNs under Combined RA/FGF exposure: A) To test if RA and FGF signaling together may lead to specification of Hoxc8$^+$ ES-MNs during differentiation, different concentrations of RA and FGF together were tested and the rostro-caudal identity of the resulting cells was determined. Addition of up to 625 ng/ml of FGF2 to 1 µM RA/Hh differentiation condition did not result in the specification of Hoxc8$^+$ ES-MNs. Treatment of differentiating ES cells with 100 nM RA/Hh and 100 ng/ml of FGF2 on day 3 of differentiation resulted in specification of Hoxc8$^+$ ES-MNs, demonstrating that under reduced retinoid conditions differentiating ES cells can acquire brachial identity in response to high concentrations of FGF2. B) To compare the efficiency of MN generation between 1 µM RA/1 µM Hh, 100 nM RA/Hh and 100 ng/ml FGF, and endogenous FGF/Hh conditions, fluorescence activated cell sorting analysis was performed on day 7 dissociated Hb9-GFP$^+$ ES-MNs. Differentiation of ES cells in the presence of 100 nM RA/Hh and 100 ng/ml FGF resulted in a more efficient specification of caudal brachial MNs as compared to differentiation guided solely by endogenous signals (~17% v. ~5%). C) To compare the efficiency of ES-MN induction between 1 µM RA/1 µM Hh, 100 nM RA/Hh and 100 ng/ml FGF, and endogenous FGF/Hh conditions, EBs were dissociated on day 6 of differentiation and plated on laminin coated coverslips. Immunostainings were performed to obtain fractions of Hb9$^+$ cells for each differentiation condition. Graphed are results from three independent differentiation experiments (mean±SEM). D) To define the rostro-caudal and columnar identity of ES-MNs obtained using 100 nM RA/Hh and 100 ng/ml FGF differentiation condition, day 6 EBs were dissociated into single cells and these were plated on laminin coated coverslips. Immunostainings for Hoxa5, Hoxc8, Lhx3, and FoxP1 were performed on day 7 of differentiation. Over 50% of ES-MNs acquire expression of Hoxc8 and ~25% acquire expression of FoxP1 suggesting that a fraction of ES-MNs acquired caudal brachial identity. Graph represents three independent experiments (mean±SEM). E) Representative images of Hoxa5, Hoxc8, Lhx3 and FoxP1 expressing ES-MNs derived using RA/Hh/FGF differentiation conditions.

FIG. 25: Columnar and divisional identity of ES-MNs: A) To define the exact populations of Lhx3$^+$ and FoxP1$^+$ ES-MNs, RA/Hh and FGF/Hh differentiated EBs were dissociated on day 6 of differentiation into single cells and plated on laminin coated coverslips. Majority of RA/Hh derived MNs express Lhx3 while FGF/Hh differentiation leads to a mixture of FoxP1$^+$ and Lhx3$^+$ ES-MNs. FoxP1 and Lhx3 expression in MNs was mutually exclusive. B) ~80% of RA/Hh ES-MNs express Lhx3 in contrast to ~30% in FGF/Hh condition (p<0.0001). ~40% of ES-MNs generated in FGF/Hh condition express FoxP1 while FoxP1 is expressed only in ~10% of RA/Hh differentiated ES-MNs (p<0.001). Graph shows three independent experiments (mean±SEM). C) To determine whether RA can influence rostro-caudal identity of ES-MNs in a time-dependent fashion, the inventors treated EBs with 10 nM RA on day 3, day 4, and day 5 of differentiation. While treatment of EBs with RA on day 3 leads to a loss of Hoxc8 expression by ES-MNs, treatment on day 4 does not. These results suggest that differentiating cells in the EBs are responsive to a rostralizing activity of RA on day 3 but not day 4 of differentiation. D) Quantification of RA influence on the rostro-caudal identity of differentiated ES-MNs when EBs are treated with RA on day 3, 4 or 5 of differentiation. While treatment on day 3 leads to a loss (~10%) of Hoxc8 expression in ES-MNs (p<0.001), treatment on day 4 or 5 does not result in significant changes in the numbers of Hoxc8$^+$ ES-MNs. Graphed are results from two independent experiments, (mean±SEM). E) Subset of ES-MNs derived under FGF/Hh conditions express LMC marker RALDH2 (shown is a section of a representative embryoid body). Within embryoid bodies, ES-MNs are incapable of clustering according to their columnar identity as determined by intermingling of FoxP1 and Lhx3 expressing ES-MNs within embryoid bodies. F) To determine if RA treatment of EBs on day5 of differentiation may result in the specification of Lhx1$^+$ ES-MNs, EBs were treated with RA on day5-7 and expression of Lhx1 in FoxP1 expressing ES-MNs was quantified. While <5% of FoxP1$^+$ ES-MNs express Lhx1 in the control condition (without late RA), addition of RA on day 5 results in a significant increase in Lhx1 expressing FoxP1$^+$ ES-MNs (~15%, p=0.044). Graphed are results of three independent experiments, (mean±SEM). G) To determine if RA treatment on day 5 results in the specification of Lhx1$^+$ LMCl identity in postmitotic MNs, the inventors treated differentiating cells on day 5 with BrdU several hours prior to addition of RA. Control (without RA) and RA treated EBs were dissociated on day 6 of differentiation and expression of Lhx1 and BrdU was examined in GFP$^+$ ES-MNs. In the control condition few MNs are BrdU$^+$, while Lhx1$^+$ MNs resulting from RA treatment not labeled with BrdU. H) While 10% of ES-MNs resulting from day 5 RA treatment were Lhx1$^+$ and were not labeled with BrdU, only ~2% of control cells (not treated with RA on day 5) were Lhx1$^+$ and were not labeled with BrdU (p=0.028). These results suggest that day 5 treatment of EBs with RA results in the specification of LMCl character in postmitotic MNs. Graphed are results from three independent experiments (mean±SEM).

FIG. 26: Analysis of Axonal Projections, Settling Position and Divisional Identity of Transplanted ES-MNs: A) Aggregates containing RA/Hh differentiated Hb9-RFP$^+$ ES-MNs and FGF/Hh differentiated Hb9-GFP$^+$ ES-MNs were plated on laminin coated coverslips to monitor axonal outgrowth of RFP$^+$ and GFP$^+$ over three day period in parallel to transplantation of the aggregates in the chick developing spinal cord. $^{++}$ Individual axons of GFP$^+$ brachio-thoracic ES-MNs (FGF/Hh condition) and RFP$^+$ cervical MNs (RA/Hh condition) can be distinguished by the expression of fluorescent proteins. B) To determine if RA/Hh derived ES-MNs prefer projecting into axial or limb muscles after transplantation into chick developing spinal cord, the inventors examined the distribution of RFP$^+$ axons along axial (A) and limb (L) branches three days post-transplantation. RFP$^+$ axons were detected in axial and limb nerve branches (image is the same section as in FIG. 6B). C) Significantly higher fraction of RA/Hh differentiated ES-MNs projects axially (p=0.036). Graph shows results for six different embryos containing RFP$^+$/GFP$^+$ grafts (mean±SEM). D) To determine the identity of RA/Hh differentiated ES-MNs that project to the limb, ES-MNs were retrogradely labeled from the limb using RhD three days after transplantation when the axonal trajectories of endogenous and grafted MNs are well defined. E) A subset of GFP$^+$ RA/Hh derived ES-MNs are retrogradely labeled with RhD from the limb (yellow cells). F, G, H, I) Retrogradely labeled GFP$^+$ MNs do not express FoxP1 (F, G) or Lhx3 (H, I) indicating their HMC-like columnar identity. F, G and H, I are same image pairs. J-O) Three days after transplantation of GFP$^+$ FGF/Hh induced brachial ES-MNs, the inventors examined the settling positions of FoxP1$^+$ and Lhx3$^+$ transplanted and endogenous MNs. These results support our observation that FoxP1$^+$ ES-MNs to settle laterally and Lhx3$^+$ ES-MNs settle medially within the developing chick spinal cord after grafting. Images in (J,K), (L,M), (M,O) are same images triple labeled for FoxP1, Lhx3 and GFP. P, Q) To determine the divisional identity of transplanted FGF/Hh derived GFP$^+$ transplanted ES-MNs, Lhx1 and FoxP1 expression were analyzed three days after transplantation into the brachial level of the chick spinal cord. Few if any FoxP1$^+$ ES-MNs express LMCl divisional marker Lhx1. P and Q are same images triple labeled for Lhx1, FoxP1, and GFP.

Figure 27:
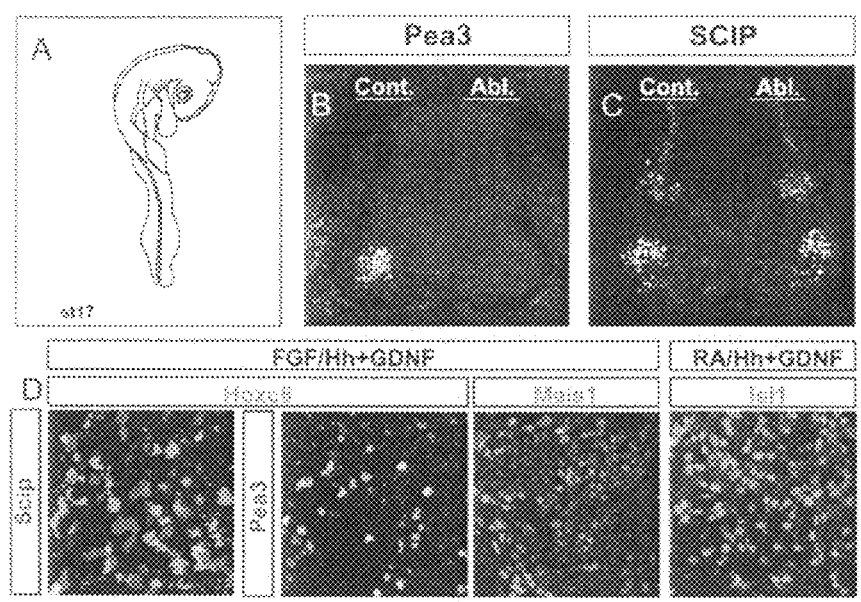

FIG. 27: Analysis of Motor Pool Identity of Caudal Brachial ES-MNs: (A-C) To test whether expression of Pea3 or Scip depends on limb derived signals, limb ablation was performed in the HH stage 17 developing chick embryo (A). Limb ablation led to a loss of Pea3 expression on the ablated side (A) but expression of Scip was not affected (C) by the procedure. Therefore, while Pea3 expression is dependent on limb derived signals, the expression of Scip is independent of the presence of the limb. D) Pea3$^+$ and Scip$^+$ motor pools are in addition marked by distinct profiles of Hoxc6 and Meis1 expression. In vivo, in addition to Pea3 expression, CM/LD motor pools can be marked by expression of Hoxc6 and lack of Meis1. In contrast, in vivo Scip$^+$ FCU MNs do not express Hoxc6. The inventors tested whether ES cell derived CM/LD motor neurons and FCU ES cell derived motor neurons express similar profile of Hoxc6. As in vivo, the majority of Pea3$^+$ (CM/LD) ES-MNs maintained expression of Hoxc6. In contrast, Hoxc6 expression was extinguished in Scip$^+$ (FCU) ES-MNs. As in vivo, Pea3$^+$ ES-MNs do not express Meis1. When treated with GDNF, RA/Hh differentiated cervical ES-MNs do not acquire expression of Pea3 suggesting that only a subset of MNs that express correct Hox profile are capable of inducing expression of Pea3.

FIG. 28: Specification of MN Subtypes from Mouse ES Cells: In response to Wnt and FGF signals, ES cells differentiate into spinal progenitors (SP) that can be patterned along the rostro-caudal axis by RA and FGF. MNs generated in the presence of RA acquire cervical identity while increasing concentrations of FGF specify brachial and thoracic MNs, as determined by differential expression of Hox genes. Correct rostro-caudal specification of MNs is demonstrated by acquisition of spinal level-appropriate columnar and motor pool identities. In vitro generated MMC and LMC ES-MNs settle in appropriate motor columns and exhibit correct axon pathfinding towards axial and limb muscles after transplantation in vivo.

DETAILED DESCRIPTION OF INVENTION

Terms

As used herein, and unless stated otherwise, each of the following terms shall have the definition set forth below.

"ADFNB" is a mammalian cell-culturing medium composed of a mixture of Advanced DMEM/F12, Neurobasal™ medium, and 1 ml B27 50× supplement. "DMEM" refers to Dulbecco's Modified Eagle Medium, a growth media commonly used in mammalian tissue culture experiments available, for example, from Invitrogen Corporation, Delaware (e.g. Cat. No. 12634-010). Neurobasal™ media are basal media formulated for neuronal cells available, for example, from Invitrogen Corporation, Delaware (e.g. Cat. No. 21103). B-27 supplements are 50× liquid serum-free supplements for growth and long-term viability of neurons available, for example, from Invitrogen Corporation, Delaware (e.g. Cat. No. 17504). Optionally, the ADFNB media can comprise Glial cell-derived neurotrophic factor (GDNF) to enhance survival of MN cultures.

"ADFNK" is a mammalian cell-culturing medium composed of a mixture of Advanced DMEM/F12 and Neurobasal™ medium that has been supplemented with 10%

Knockout™-SR media available, for example, from Invitrogen Corporation, Delaware (e.g. Cat. No. 10828). Knockout™-SR, or Knockout-Serum Replacement is a serum replacement for embryonic stem cells.

"Administering to the subject" means the giving of, dispensing of, or application of medicines, drugs, or remedies to a subject to relieve or cure a pathological condition.

"DV", or "Dorsoventral" axis is an anatomical term of location describing the anatomical axis running from spinal column (back) to belly (front).

"EBs" means Embryoid Bodies, which are aggregates of cells derived from embryonic stem cells.

"ES cells" means Embryonic Stem cells which are stem cells derived from the inner cell mass of an early stage embryo known as a blastocyst.

"Essentially free" means that zero or a de minimus amount of the component that the composition is essentially free from, such as retinoic acid, may be present that does not prevent the generation of caudal Motor Neurons. In one embodiment of the present invention, a medium that is essentially free of retinoic acid does not contain exogenously added retinoic acid, or only contains a trace amount of retinoic acid/all-trans retinoid acid as are present from the isolation of other components that are added to the media and which does not prevent generation of a caudal motor neuron.

"FCU" means the Flexor Carpi Ulnaris muscle, a muscle of the human forearm that acts to flex and adduct the hand.

"FGFs", or Fibroblast Growth Factors, refers to a family of growth factors involved in angiogenesis, wound healing, and embryonic development. FGF is further divided into two forms: the acidic fibroblast growth factor" (FGF-1) and the basic fibroblast growth factor (bFGF or FGF-2).

"GDFs", or Growth Differentiation Factors, are a subfamily of proteins belonging to the transforming growth factor beta (TGFβ) family that have functions predominantly in development. One member of the GDF family, GDF-11, controls the anterior-posterior patterning by regulating the expression of Hox genes. It determines Hox gene expression domains and rostrocaudal identity in the caudal spinal cord.

"GFP", or Green Fluorescent Protein, is a protein derived from jellyfish Aequorea victoria used as a marker for genetic activity due to its natural and spontaneous fluorescence.

"Isotonic solution" as used herein means a solution in which nerve cells or nerve cell precursors can be bathed without a net flow of water across a semi-permeable cell membrane. Non-limiting examples include a physiologic salt solution and blood serum. An "isotonic salt solution" means aqueous solution of 0.9 percent of one or more salts such as sodium chloride, isotonic with the tissue fluid, or cerebrospinal fluid, and in which nerve cells can be bathed without a net flow of water across their cell membranes.

"LMC", or Lateral Motor Column neurons are motor neurons that develop only at limb levels and innervate limb muscles in mammals.

"MMC", or Median Motor Column neurons are motor neurons that innervate axial and body wall muscles in mammals.

"MN", or Motor Neuron, is a neuron that conveys impulses from the central nervous system to a muscle, gland, or other effector tissue in a mammal.

"Neuronal cell", or "neuron", as used herein, refers to a conducting or excitable mammalian nerve cell of the nervous system. Examples of neurons include, without limitation, neurons of the dorsal root ganglia (DRG), motor neurons, peripheral neurons, sensory neurons, neurons of the spinal cord, and ventral interneurons.

"Nervous tissue" refers to tissue of the nervous system, both central and peripheral, which includes the differentiated neural cells of the present invention and progenitors thereof, unless otherwise stated.

"Nervous tissue degeneration" means a condition of deterioration of nervous tissue, wherein the nervous tissue changes to a lower or less functionally-active form.

"Peripheral neuropathy" refers to a nervous tissue-based syndrome of sensory loss, muscle weakness, muscle atrophy, decreased deep-tendon reflexes, and/or vasomotor symptoms. In a subject who has peripheral neuropathy, myelin sheaths (or Shwann cells) may be primarily affected, or axons may be primarily affected. The peripheral neuropathy may affect a single nerve (mononeuropathy), two or more nerve in separate areas (multiple mononeuropathy), or many nerves simultaneously (polyneuropathy).

"RA," as used herein means retinoic acid, which is the oxidized form of Vitamin A. It functions in determining position along embryonic anteroposterior axis in chordates. It acts through Hox genes, which ultimately controls anterior/posterior patterning in early developmental stages. RAs belong to the retinoids class of chemical compounds.

"Retinoids" are a class of chemical compounds that are related chemically to vitamin A. The basic structure of the retinoid molecule consists of a cyclic end group, a polyene side chain and a polar end group.

"RC", or Rostrocaudal, (also known as "AP", or Anteroposterior) is an anatomical term of location describing the anatomical axis running from head end to opposite end of body or tail.

"SHh" or Sonic hedgehog homolog is one of three proteins in the mammalian hedgehog family, the others being desert hedgehog "DHh" and Indian hedgehog "IHh". SHh is the best studied ligand of the hedgehog signaling pathway. It plays a key role in regulating vertebrate organogenesis, such as in the growth of digits on limbs and organization of the brain.

Embodiments of the Invention

The subject invention provides a method for generating a caudal motor neuron comprising culturing an embryonic stem cell in a composition which is essentially free of retinoids and comprises an isotonic salt solution, so as to generate the caudal motor neuron.

In one embodiment, the composition is essentially free of all-trans retinoic acid.

In one embodiment, the method further comprises contacting the generated caudal motor neuron with retinoic acid, so as to produce a cervical motor neuron. The another embodiment, the method further comprises contacting the generated caudal motor neuron with Fibroblast Growth Factor-2 (FGF-2), so as to produce a thoracic motor neuron. In yet another embodiment, the method further comprises contacting the generated caudal motor neuron with Growth differentiation factor 11 (Gdf11), so as to produce a lumbar motor neuron.

In an embodiment, the cells are primarily maintained in culture.

In an embodiment, the cells are cultured in an isotonic salt solution at or about 37° C. in a 5% $CO_2$/95% $O_2$ atmosphere, which salt solution comprises glucose. The culture may be an adhesion culture or a suspension culture. The isotonic salt solution may be supplemented with serum, for example, calf serum at 1-10%.

The subject invention also provides a method of generating a neuron expressing Hoxc8, comprising culturing an embryonic stem cell in a composition which is essentially free of retinoids and comprises an isotonic salt solution, so as to generate the neuron which expresses Hoxc8 transcription factor.

In one embodiment, the method further comprises contacting the generated neuron with retinoic acid, so as to produce a neuron which expresses Hoxa5 or Hoxc6 transcription factors. In another embodiment, the method further comprises contacting the generated neuron with Fibroblast Growth Factor-2 (FGF-2), so as to produce a neuron which expresses Hoxd9 transcription factor. In yet another embodiment, the method further comprises contacting the generated neuron with Growth differentiation factor 11 (gdf11), so as to produce a neuron which expresses Hoxd10 transcription factor.

The subject invention also provides a population of cells comprising the neuron produced by the above-described methods.

The subject invention also provides a method for generating a caudal brachial motor neuron from an embryonic stem cell, comprising culturing the embryonic stem cell in a composition essentially free of retinoids and comprising an amount of Advanced Dulbecco's Modified Eagle's Medium/F12 and Neurobasal medium that has been supplemented with 10% Knockout-Serum Replacement (ADFNK medium) effective to produce the caudal brachial motor neuron.

In one embodiment, the method further comprises contacting the caudal brachial motor neuron with at least one neurotrophic factor. In another embodiment, the caudal brachial motor neuron expresses Hoxc8 transcription factor. In yet another embodiment, the caudal brachial motor neuron expresses Hox6 transcription factor.

In one embodiment, the caudal brachial motor neuron is transfected so that it expresses enhanced green fluorescent protein (eGFP).

In one embodiment, the embryonic stem cell is a murine embryonic stem cell. In another embodiment, the embryonic stem cell is a human embryonic stem cell.

In one embodiment, the culturing is effected in vivo in a subject. In another embodiment, the culturing is effected in vivo.

In one embodiment, the embryonic stem cell is further contacted with. Fibroblast Growth Factor (FGF). In another embodiment, the contacting is effected in vivo in a subject. In another embodiment, the contacting is effected in vivo in a subject by administering the Fibroblast Growth Factor (FGF) to the subject. In yet another embodiment, the contacting is effected in vitro.

The subject invention also provides a method of transplanting a motor neuron into a subject comprising: a) generating a motor neuron by culturing an embryonic stem cell in a composition essentially free of retinoids and comprising an isotonic salt solution, so as to generate the motor neuron; and b) transplanting the motor neuron into the subject.

In one embodiment, the motor neuron is a caudal brachial motor neuron.

In one embodiment, the caudal brachial motor neuron is transplanted into a spinal cord of the subject.

In one embodiment, the subject is an adult. In another embodiment, the subject is human.

In one embodiment, the subject has nervous tissue degeneration. In another embodiment, the nervous tissue degeneration is a peripheral neuropathy or a neurodegenerative disease. In another embodiment, the peripheral neuropathy is a symptom of amyotrophic lateral sclerosis (ALS), neural trauma, paraneoplastic syndrome, polio, postpolio syndrome, progressive bulbar palsy, or spinal muscular atrophy (SMA). In yet another embodiment, the neurodegenerative disease is Alzheimer's disease, amyotrophic lateral sclerosis (Lou Gehrig's Disease), Binswanger's disease, Huntington's chorea, multiple sclerosis, myasthenia gravis, Parkinson's disease, or Pick's disease.

The subject invention also provides a caudal brachial motor neuron produced by the above-described methods. In one embodiment, the caudal brachial motor neuron expresses enhanced green fluorescent protein (eGFP).

The subject invention also provides a population of cells comprising the caudal brachial motor neuron produced by the above-described methods. In one embodiment, some or all of the caudal brachial motor neurons express enhanced green fluorescent protein (eGFP).

The subject invention also provides a method for generating a thoracic motor neuron from an embryonic stem cell comprising contacting the embryonic stem cell with a composition essentially free of retinoids and comprising an amount of Fibroblast Growth Factor-2 (FGF-2) effective to produce the thoracic motor neuron.

In one embodiment, the method further comprise contacting the thoracic motor neuron with at least one neurotrophic factor. In another embodiment, the thoracic motor neuron expresses Hoxd9 transcription factor. In another embodiment, the thoracic motor neuron expresses Hoxc9 transcription factor. In yet another embodiment, the thoracic motor neuron expresses Hoxc8 transcription factor.

In one embodiment, the embryonic stem cell is a murine embryonic stem cell. In another embodiment, the embryonic stem cell is a human embryonic stem cell.

In one embodiment, the thoracic motor neuron is transfected so that it expresses enhanced green fluorescent protein (eGFP).

In one embodiment, the contacting is effected in vivo in a subject. In another embodiment, the contacting is effected in vivo in a subject by administering the Fibroblast Growth Factor-2 (FGF-2) to the subject. In yet another embodiment, the contacting is effected in vitro.

The subject invention also provides a method of transplanting a thoracic motor neuron into a subject comprising: a) generating a motor neuron by culturing an embryonic stem cell in a composition essentially free of retinoids and comprising an isotonic salt solution, so as to generate the motor neuron; b) administering Fibroblast Growth Factor-2 (FGF-2) to the generated motor neuron so as to generate the thoracic motor neuron; and c) transplanting the thoracic motor neuron into the subject.

In one embodiment, the thoracic motor neuron is a human thoracic motor neuron.

In one embodiment, the thoracic motor neuron is transplanted into a spinal cord of the subject.

In one embodiment, the subject is an adult. In another embodiment, the subject is a human.

In one embodiment, the subject has nervous tissue degeneration. In another embodiment, the nervous tissue degeneration is a peripheral neuropathy or a neurodegenerative disease. In another embodiment, the peripheral neuropathy is a symptom of amyotrophic lateral sclerosis (ALS), neural trauma, paraneoplastic syndrome, polio, postpolio syndrome, progressive bulbar palsy, or spinal muscular atrophy (SMA). In yet another embodiment, the neurodegenerative disease is Alzheimer's disease, amyotrophic lateral sclerosis (Lou Gehrig's Disease), Binswanger's disease, Huntington's chorea, multiple sclerosis, myasthenia gravis, Parkinson's disease, or Pick's disease.

The subject invention also provides a thoracic motor neuron produced by the above-described methods. In one embodiment, the thoracic motor neuron expresses enhanced green fluorescent protein (eGFP).

The subject invention also provides a population of cells comprising the thoracic motor neuron produced by the above-described methods. In one embodiment, some or all of the thoracic motor neurons express enhanced green fluorescent protein (eGFP).

The subject invention also provides a method for generating a lumbar motor neuron from an embryonic stem cell comprising contacting the embryonic stem cell with a composition essentially free of retinoids and comprising an amount of Growth differentiation factor 11 (Gdf11) effective to produce the lumbar motor neuron.

In one embodiment, the method further comprises contacting the lumbar motor neuron with at least one neurotrophic factor.

In one embodiment, the lumbar motor neuron expresses Hoxd10 transcription factor.

In one embodiment, the embryonic stem cell is a murine embryonic stem cell. In another embodiment, the embryonic stem cell is a human embryonic stem cell.

In one embodiment, the lumbar motor neuron is transfected so that it expresses enhanced green fluorescent protein (eGFP).

In one embodiment, the contacting is effected in vivo in a subject. In another embodiment, the contacting is effected in vivo in a subject by administering the Growth differentiation factor 11 (Gdf11) to the subject. In another embodiment, the contacting is effected in vitro in a subject.

In one embodiment, the embryonic stem cell is further contacted with an amount of Fibroblast Growth Factor 2 (FGF-2). In another embodiment, the contact with Fibroblast Growth Factor 2 (FGF-2) is effected in vivo in a subject. In another embodiment, the contact with Fibroblast Growth Factor 2 (FGF-2) is effected in vivo in a subject by administering the FGF-2 to the subject. In yet another embodiment, the contact with Fibroblast Growth Factor 2 (FGF-2) is effected in vitro.

The subject invention also provides a method of transplanting a lumbar motor neuron into a subject comprising: a) generating a motor neuron by culturing an embryonic stem cell in a composition essentially free of retinoids and comprising an isotonic salt solution, so as to generate the motor neuron; b) administering Growth differentiation factor 11 (Gdf11) to the generated motor neuron so as to generate the lumbar motor neuron; and c) transplanting the lumbar motor neuron into the subject.

In one embodiment, the lumbar motor neuron is a human lumbar motor neuron.

In one embodiment, the lumbar motor neuron is transplanted into a spinal cord of a subject.

In one embodiment, the subject is an adult. In another embodiment, the subject is a human.

In one embodiment, the subject has nervous tissue degeneration. In another embodiment, the nervous tissue degeneration is a peripheral neuropathy or a neurodegenerative disease. In another embodiment, the peripheral neuropathy is a symptom of amyotrophic lateral sclerosis (ALS), neural trauma, paraneoplastic syndrome, polio, postpolio syndrome, progressive bulbar palsy, or spinal muscular atrophy (SMA). In yet another embodiment, the neurodegenerative disease is Alzheimer's disease, amyotrophic lateral sclerosis (Lou Gehrig's Disease), Binswanger's disease, Huntington's chorea, multiple sclerosis, myasthenia gravis, Parkinson's disease, or Pick's disease.

The subject invention also provides a lumbar motor neuron produced by the above-described methods. In one embodiment, the lumbar motor neuron expresses enhanced green fluorescent protein (eGFP).

The subject invention also provides a population of cells comprising the lumbar motor neuron produced by the above-described methods. In one embodiment, some or all of the lumbar motor neurons express enhanced green fluorescent protein (eGFP).

In an embodiment of the methods, cells and populations of cells, the embryonic stem cells are mammalian. In a further embodiment, the embryonic stem cells are human.

The subject invention also provides a population of motor neuron cells enriched for motor neuron cells expressing Foxp1 and expressing a gene associated with Spinal Muscular Atrophy (SMA) or Amyotrophic Lateral Sclerosis (ALS).

In one embodiment, the gene associated with ALS is a mutated SOD1 gene. In another embodiment, the gene associated with SMA is a mutated SMN1 gene.

The specific embodiments and examples described herein are illustrative, and many variations can be introduced on these embodiments and examples without departing from the spirit of the disclosure or from the scope of the appended claims. Elements and/or features of different illustrative embodiments and/or examples may be combined with each other and/or substituted for each other within the scope of this disclosure and appended claims.

Further non-limiting details are described in the following Experimental Details section which is set forth to aid in an understanding of the subject matter but is not intended to, and should not be construed to, limit in any way the claims which follow thereafter.

EXPERIMENTAL DETAILS

Example 1

Relevant to this application, the current status of knowledge of MN subtypes and spinal AP patterning mechanisms is summarized as follows:

While generic MN identity is specified by DV patterning mechanisms, MN subtype diversity is manifested primarily along the anteroposterior axis of the spinal cord, as MNs at each spinal segment innervate distinct subsets of muscle targets. Little is currently understood about the mechanisms that underlie acquisition of AP spinal identity and about the genetic cascades that translate the progenitor AP identity to postmitotic MNs.

Columnar Identity

Traditionally MNs were classified based on two criteria: position within the spinal cord, which defines their columnar identity; and axon trajectory and pattern of muscle innervations, which defines their motor pool identity (Hollyday, 1980; Hollyday and Jacobson, 1990; Landmesser, 1978). Spinal MNs are arranged in longitudinal columns, each innervating a distinct subset of peripheral targets. One motor column, the medial subdivision of median motor column (MMCm) containing MNs innervating axial muscles, is found at all segmental levels of the spinal cord. All the other columns occupy distinct spinal cord segments along the AP axis. Lhx3, a LIM homeodomain transcription factor transiently expressed by all MNs, is selectively maintained in MMCm MNs (Sharma et al., 1998). At limb levels of the spinal cord, MNs innervating limb muscles are organized within the lateral motor column (LMC). LMC MNs, characterized by the expression of retinaldehyde dehydrogenase 2 (RALDH2) enzyme (Sockanathan and Jessell, 1998) are further subdivided into lateral LMC (LMCl) MNs expressing Lhx1 and Hb9 transcription factors that innervate dorsal muscles of the limb and medial LMC (LMCm) MNs expressing Lsl1 LIM domain transcription factor that innervate the ventral muscles (Tsuchida et al., 1994).

In addition to limb-innervating motor neurons found in cervical and lumbar spinal cord, thoracic spinal cord contains preganglionic autonomic motor columns that harbors nNOS positive MNs innervating sympathetic ganglia (Doone et al., 1999) and a lateral subdivision of MMC column that contain motor neuron innervating intercostals and body wall muscles.

Motor Pool Identity

In addition to their columnar identity, MNs within LMC acquire discrete motor pool identity. Each muscle group in the limb is innervated by a specific pool of MNs, and each motor pool occupies a characteristic RC and mediolateral position within the LMC (Hollyday, 1980; Landmesser, 1978). Motor neuron pools can be defined by the expression of transcription factors of the ETS family, notably Pea3, Er81 and Pou transcription factor Scip/Oct6/Pou3f1. The onset of expression of Pea3 by LMC neurons occurs well after cell cycle exit, coincides with axonal invasion of the limb mesenchyme, and depends on limb-derived signals that include GDNF and HGF (Haase et al., 2002; Helmbacher et al., 2003). These observations indicate that these pool specific transcription factors mark the late phase of motor pool specification. Accordingly, in Pea3 mutant mice the axons of specific motor neuron pools undergo normal initial outgrowth toward their specific muscle but fail to branch normally within their target muscles, and the cell bodies of these motor neurons are mis-positioned within the spinal cord (Livet et al., 2002). These studies have provided an initial insight into the late phase of motor neuron pool specification, however they did not elucidate developmental processes leading to the specification of individual motor pool identities that occurs soon after LMC neurons exit the cell cycle, long before their axon \reach specific muscle targets (landmsser, 1980).

Motor Neuron Hox Code and Specification of Columnar Pool Identity

Classical embryological experiments performed in the developing chick established that both columnar and pool MN subtype identities are specified independently of their muscle targets. Anteroposterior differences in the columnar identity of spinal MNs are established in response to the sequential actions of two extrinsic signals: an early gradient of FGF signaling activity derived from the node region, and a later influence of retinoid signaling provided by cervical paraxial mesoderm (Dasen et al., 2003; Liu et al., 2001). In response to these signals, neural progenitor cells acquire specific anteroposterior identities that are translated into a distinct pattern of Hox gene expression in postmitotic spinal MNs. The LMC columnar identity is specified by selective expression of Hoxc6 and Hoxa6 (Hox6) genes at the forelimb and Hoxc10 and Hoxd10 (Hox10) homeodomain transcription factors at hindlimb LMC MNs (Dasen et al., 2003; de la Cruz et al., 1999; Lin and Carpenter, 2003; Wahba et al., 2001). The preganglionic motor column at thoracic spinal cord is similarly specified through the activity of Hoxc9 and Hoxd9 (Hox9) transcription factors (Dasen et al., 2003). The divergence of LMC and preganglionic identities along the RC axis of the spinal cord is reinforced by mutual transcriptional cross-repressive interactions between the Hox6 and Hox9 proteins (Dasen et al., 2003)

A recent study established that Hoxa, Hoxc, and Hoxd paralogous genes and their cofactors (Meis %) might be involved not only in specification of AP segmental and columnar identity but also in the establishment of ultimate motor pool identities. Such involvement of Hox genes was demonstrated in the establishment of several motor pool identities at the forelimb level of the spinal cord (including Pea3 and Scip expressing motor pools). Cross repressive transcriptional regulatory interactions among initially co-expressed sets of Hox genes lead to the establishment of MNs expressing unique complements of Hox genes that in turn define resulting motor pool identities (Dasen et al., 2005) While this view emphasizes the cell autonomous mechanisms involved in specification of MN subtype identity (after the initial non autonomous specification of MN progenitor AP identity), late paracrine signaling might be involved in refinement of final MN subtype identity. Indeed, it has been shown that paracrine retinoid signaling plays a critical role in acquisition of LMC columnar character by postmitotic MNs (Sockanathan and Jessell, 1998; Sockanathan et al., 2003) In addition experimental transplantations and ablations of individual MNs in developing zebrafish spinal cord lead to re-specification of postmitotic MN subtype identity, thus emphasizing the role of late cell interactions in this process (Eisen, 1992). Together these results argue for involvement of both cell autonomous and non-autonomous mechanisms in specification of ultimate MN subtype identity. Because this ambiguity and the general lack of information on specification of mammalian MN subtype identity, contribution of each of these processes to specification of mammalian MNs needs to be carefully examined.

A second challenge lies in the fact that current ES cell to MN differentiation methods rely on the combinatorial effect of two exogenous signaling molecules—retinoic acid (RA) and hedgehog (Hh). Retinoic acid is used to promote neutralization of differentiating ES cells and specification of RC spinal identity while Hh signaling is necessary for ventralization of spinal cells to specify MN progenitors (Jessell, 2000; Wichterle et al., 2002).

The problem is that retinoic acid stimulation can only selectively regenerate cervical motor neurons, and prevent generation of more caudal motor neurons. More specifically, besides promoting generation of motor neurons, retinoic acid is the principal patterning signal specifying hindbrain and rostral spinal cord territories. Thus, application or retinoic acid to differentiation ES cells leads to selective generation of cervical motor neurons that normally innervate axial muscles, characterized by Hoxc5 transcription factor (Wichterle et al., 2002), while it prevents generation of more caudal motor neuron subtypes of the brachial, thoracic or lumbar identity. Interestingly, the majority of ES cell-derived MNs maintain expression of Lhx3 (Soundrarajan et al., 2006; Wichterle et al., 2002) indicating their MMCm columnar identity.

In contrast to relatively poorly characterized subtype diversity and connectivity of cervical spinal motor neurons, developmental molecular and anatomical attributes defining diverse motor neuron subtypes in caudal brachial spinal cord are understood in a great detail. Brachial spinal motor neurons (bMNs) are one of the best-characterized nerve cells in terms of their subtype diversity. Their cell body settling positions and muscle connectivity have been mapped in great detail, and the key signaling molecules and transcriptional programs controlling bMNs subtype diversification have been identified.

ES Cell Culture

Differentiation of cervical level motor neurons from mouse ES cells was performed as previously described (Wichterle et al., 2002). For differentiation of caudal brachial level MNs from ES cells, ES cells were grown in ES cell medium for two days, dissociated and plated into non-adherent tissue culture dishes using ADFNK medium at a density of 20,000 cells/ml. Medium is changed each day but not on Day 3 and Day 4 of differentiation (three and four days after dissociation of ES cells and plating into differentiation medium, respectively).

Addition of any factors to differentiating embryonic bodies (EBs) was performed on Day 3. These included: 1 µg/ml Dickopf-1 Dkk1 (R&D Systems), FGF Receptor Inhibitor (PD173074, 100 nM final concentration), FGFb (Recombinant Human, FTF-basic, 120-17, PeproTech), rhGdf11 (R&D Systems, Cat#1958-GD). GDNF (10 ng/ml, R&D Systems) was supplemented on Day 5 of differentiation in selected cultures.

ES Cell-Derived MN Culture

For immunocytochemical analysis, embryonic bodies (EBs) were dissociated using 0.05% Trypsin-EDTA on Day 6 and plated at low densities on laminin coated coverslips using ADFNB medium supplemented with 10 ng/ml Glial cell-derived neurotrophic factor (GDNF). For quantification of MN subtypes, EBs were collected on Day 6 and dissociated using 0.05 Trypsin-EDTA. Dissociated cells were plated on laminin coated coverslips using ADFNB medium (DMEM/F12, Neurobasal, 1 ml B27 50× supplement and optional 5 ng/ml of GDNF to enhance survival of MN cultures) and fixed with 4% PFA one day later.

Immunocytochemistry

Immunocytochemistry on ES cell-derived MNs and EBs was performed as previously described (Wichterle et al., 2002). Antibodies against the following proteins were used in the analysis during this study: Otx2, Hoxa5, Hoxc8, Hoxc6, Hoxc9, Hoxd9, Hoxd10, Foxp1, Lhx3, Pea3, Scip, NeuN, dsRed, NF.

Transplantation of ES Cell-Derived Spinal MNs into Chick Developing Neural Tube

Transplantation of ES cell-derived MNs into chick developing neural tube was performed as previously described (Wichterle et al., 2002). For the experiments using mixed hanging drops, cervical level MNs were differentiated using Hb9::dsRed; Olig2::GFP ES cell line, while brachial level MNs were generated using Hb9::GFP ES cell line. EBs were dissociated on Day 6 using Trypsin and hanging drops were generated by mixing cervical and brachial level ES cell-derived MNs together and generating 50 µl drops containing 5,000-10,000 cells that are placed on the lid of a 10 cm² cell culture dish which is then inverted. Hanging drops or brachial level EBs only were transplanted into H&H stage 14-17 chick developing embryo at the brachial level of the developing spinal cord (somite level 15-20). Embryos were then fixed and processed for immunohistochemistry 16-20 µm cryostat sections were generated for analysis.

Retrograde Labeling of ES Cell-Derived MNs from the Limb and Axial Musculature

Retrograde labeling was performed as previously described (Dasen et al., 2005). Three day post-transplantation, GFP+ brachial level MNs were identified in the spinal cord and axial or limb nerves were first cut and RhD (lysolecithin) was injected into the GFP labeled nerve. The embryos were incubated in the oxygenation bath for several hours, then fixed and processed for immunohistochemistry.

Cell Culture Quantifications

For each experiment, 10 distinct randomized image fields were taken using a confocal microscope LSM Zeiss Meta 510. Expression of all markers used for quantifications was gated to GFP positive cells, ES cell-derived spinal MNs. Images were analyzed for the expression of the above stated markers in the context of the ES cell-derived caudal brachial MNs. Each quantification is the result of at least three independent experiments (three independent differentiation experiments).

Mixed Transplant Quantifications

Three days after transplantation of mixed hanging drops, embryos were processed for immunohistochemistry (Wichterle et al., 2002). For all analysis, dsRed and NF antibodies were used. GFP positive axons are visible without immunohistochemistry in the Hb9::GFP transgenic ES cell line. Cross sections of the spinal cord and the musculature were used to perform immunohistocytochemistry (IHC) and images were acquired to quantify the extent to which each (dsRed+ cervical ES-MNs) or (GFP+ brachial ES-MNs) were able to project to the limb or axial musculature at the first axonal projection decision point after the motor axons exit through the ventral root. Image J™ was used to quantify the area of the dsRed axial and limb projecting axons and GFP axial and limb projecting axons for each of the six embryos.

Retrograde Labeling Quantifications

Using Metamorph Offline Software, individual GFP+ only, RhD+ only, or RhD+ GFP+ double positive cell bodies were selected and the absolute intensities of Foxp1 and Lhx3 transcription factor were obtained from confocal images of these transplants with IHC performed for Foxp1 and Lhx3 transcription factors. According to these measurements, the fraction of each population of cited cells expressing Lhx3 or Foxp1 transcription factors were deduced.

Results

Figure 7:
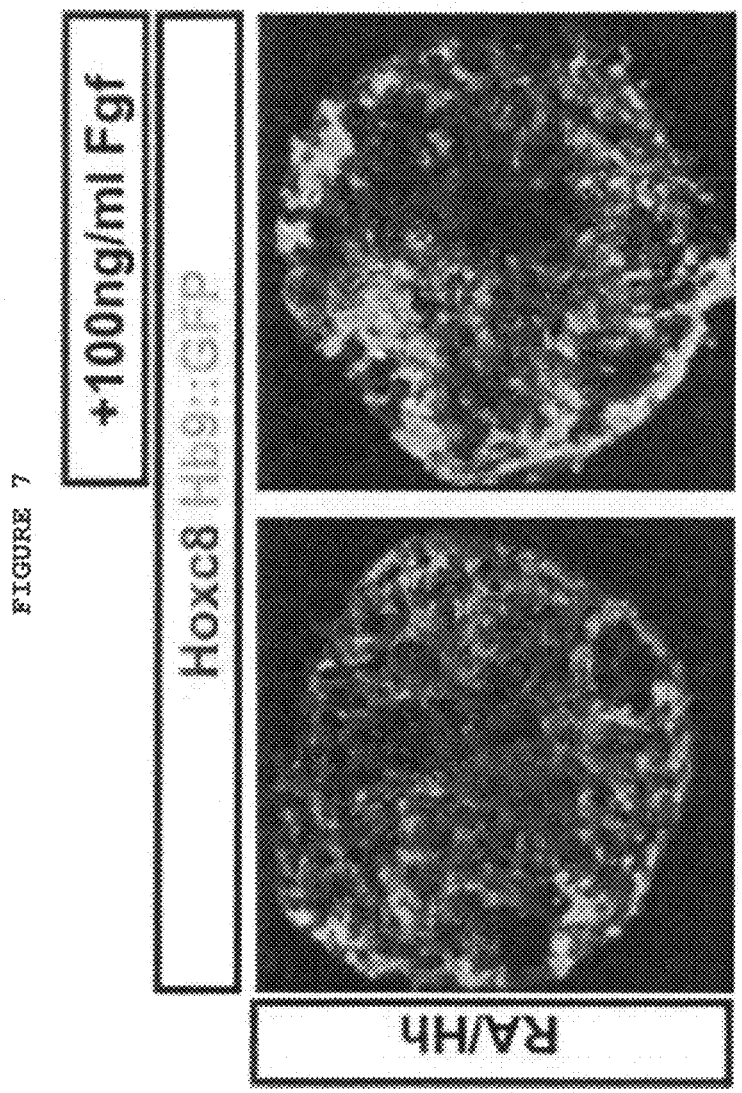
FIG. 7: shows that while brachio-cervical boundary in the developing chick neural tube can be shifted rostrally by activation of FGF signaling, addition of FGF-2 to differentiating ES cells was not sufficient to induce expression of brachial or thoracic markers in the presence of RA.

Rostro-caudal Patterning of Differentiated ES Cells in Response to Developmentally Relevant Signals Spinal segmental identity is specified in chick embryo by a set of caudalizing signals that include retinoic acid (RA), fibroblast growth factor (FGF) and growth/differentiation factor 11 (GDf11), (FIG. 1A) (Dasen et al., 2003; Liu et al., 2001; Nordstrom et al., 2006). Mouse ES cells cultured in the absence of serum differentiate readily into nerve cells (Watanabe et al., 2005), providing basal condition for testing responsiveness of mammalian cells to caudalizing signals. ES cells differentiated as embryoid bodies (EBs) were supplemented with RA, FGF or Gdf11 on Day 3 of differentiation at the onset of expression of primitive ectoderm or early neural plate markers (FGF-5, Sax1 and Sox1 (Stpyridis et al., 2007). Expression pattern of a series of RC positional markers was examined two to four days later. Retinoid treatment of differentiating ES cells induced rostral cervical identity characterized by Hoxa5 expression (FIG. 1B). While brachio-cervical boundary in the developing chick neural tube can be shifted rostrally by activation of FGF signaling, addition of FGF-2 to differentiating ES cells was not sufficient to induce expression of brachial or thoracic markers in the presence of RA (FIG. 7).

In contrast, FGF-2 treatment in absence of RA induced predominantly thoracic identity marked by Hoxd9 expression. Differentiation of ES cells either in Gdf11 factor alone or in combination with FGF 2 resulted in the emergence of even more caudal Hoxd10 positive lumbar nerve cells (FIG. 1B). Interestingly, robust induction of caudal brachial nerve cells expressing Hoxc8 has been obtained when differentiating ES cells were cultured in medium composed of a mixture of Advanced DMEM/F12 and Neurobasal medium that has been supplemented with 10% Knockout-SR but did not contain any other extrinsic signaling factors (ADFNK medium).

Specification of Caudal Brachial Spinal Identity is Dependent on Wnt and FGF Signals ADFNK differentiation medium is not supplemented with caudalizing factors (the only proteins in the medium are Insulin, Transferrin and lipid-rich bovine serum Albumin), yet EBs cultured in this condition acquire predominantly spinal identity. This result suggests that the necessary caudalizing signals are expressed and secreted by differentiating stem cells. Since specification of brachio-thoracic spinal cord depends on Wnt and FGF signals in the developing chick (Nordstrom et al., 2006), whether these factors are required for patterning of neural cells in vitro was examined. Blocking Wnt signaling with Wnt antagonist Dickkopf1 (Dkk1, 1 µg/ml) on Day 3 of differentiation did not interfere with neural specification as numerous cells expressing generic neuronal marker NeuN were detected (FIG. 1B). However, nerve cells generated in the absence of Wnt signaling lost their spinal identity as indicated by the absence of Hoxa5, Hoxc8, Hoxd9 or Hoxd10 expression and instead acquired rostral (prosencephalic or mesencephalic) neural identity manifested by the induction of Otx2 expression (Nordstrom et al., 2002; Nordstrom et al., 2006). This result indicates that Wnt signals are necessary for caudalization of the rostral identity acquired by default during neutralization of ES cells.

In addition to Wnt signaling, FGF is necessary for specification of caudal spinal character in chick neural tube in vitro and in vivo (Dasen et al., 2003; Liu et al., 2001). ES cells express high levels of FGF-4 (Wilder et al., 1997) and EBs on Day 2 of differentiation express high levels of FGF-5 (Stpyridis et al., 2007). To test whether endogenous FGFs might cooperate with Wnt signals to specify brachial spinal identity, a specific FGF receptor tyrosine kinase inhibitor, PD173074, was used (Mohammadi et al., 1998; Skaper et al., 2000)). As FGF signaling is required for specification of neural identity (Stpyridis et al., 2007; Wilson et al., 2000), EBs were treated with 100 nM PD173074 on Day 3 of differentiation, at a point when generic neural identity has been already established. Clocking FGF signaling resulted in a complete loss of Hoxc8+ cells (FIG. 1B), but in contrast to Wnt signaling, FGF was dispensable for specification of cervical Hoxa5 positive cells (FIG. 1B). Together, these results suggest that endogenous sources of Wnt signaling are required to establish generic spinal identity and FGF signaling is essential for specification of Hoxc8 positive caudal brachial cells.

Endogenous Hedgehog Signaling Patterns EBs to Specify Motor Neuron Identity

Figure 2:
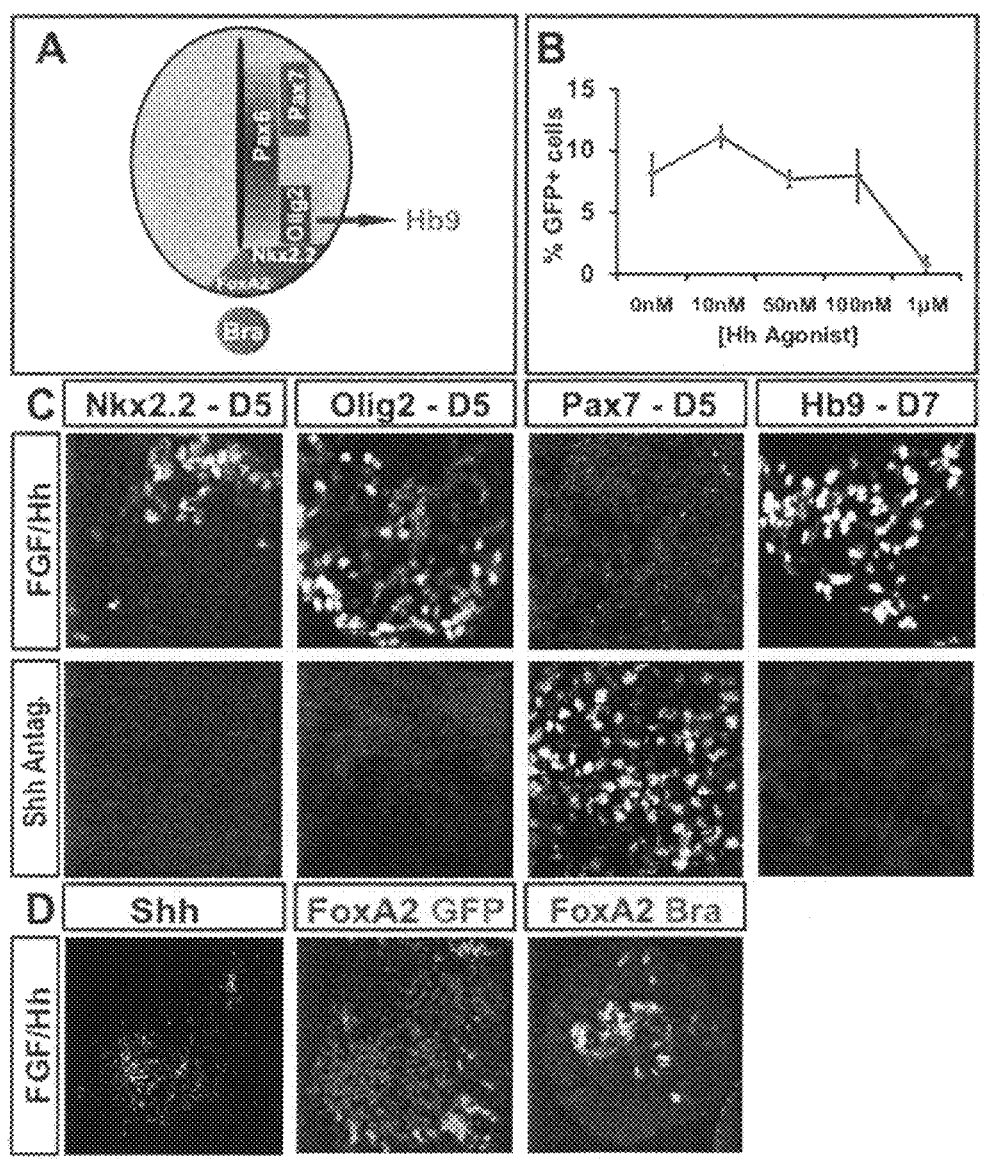
FIG. 2: shows that endogenous hedgehog signaling patterns Embryonic Bodies (EBs) to specify motor neuron identity.

Generation of spinal motor neurons is dependent on Sonic Hedgehog (SHh) signaling that patterns the ventral neural tube and specifies Olig2+ motor neuron progenitor domain (pMN) (FIG. 2A). To determine optimal concentration of Shh for specification of caudal brachial MNs, cultures of differentiating Hb90GFP ES cells were supplemented with increasing concentrations of Hh agonist (HhAg1.3) on Day 2 of differentiation. The efficiency of motor neuron specification was monitored by quantifying GFP positive MNs on Day 6 of differentiation. In contrast to cervical MNs generated in the presence of RA that are efficiently induced with 0.5-2 µM HhAg1.3 (Wichterle et al., 2002), caudal brachia MNs generated in ADFNK medium were most efficiently induced (8-10% of all cells) in the absence or low concentrations of HhAg1.3 (<100 nM), (FIG. 2B).

Figure 8:
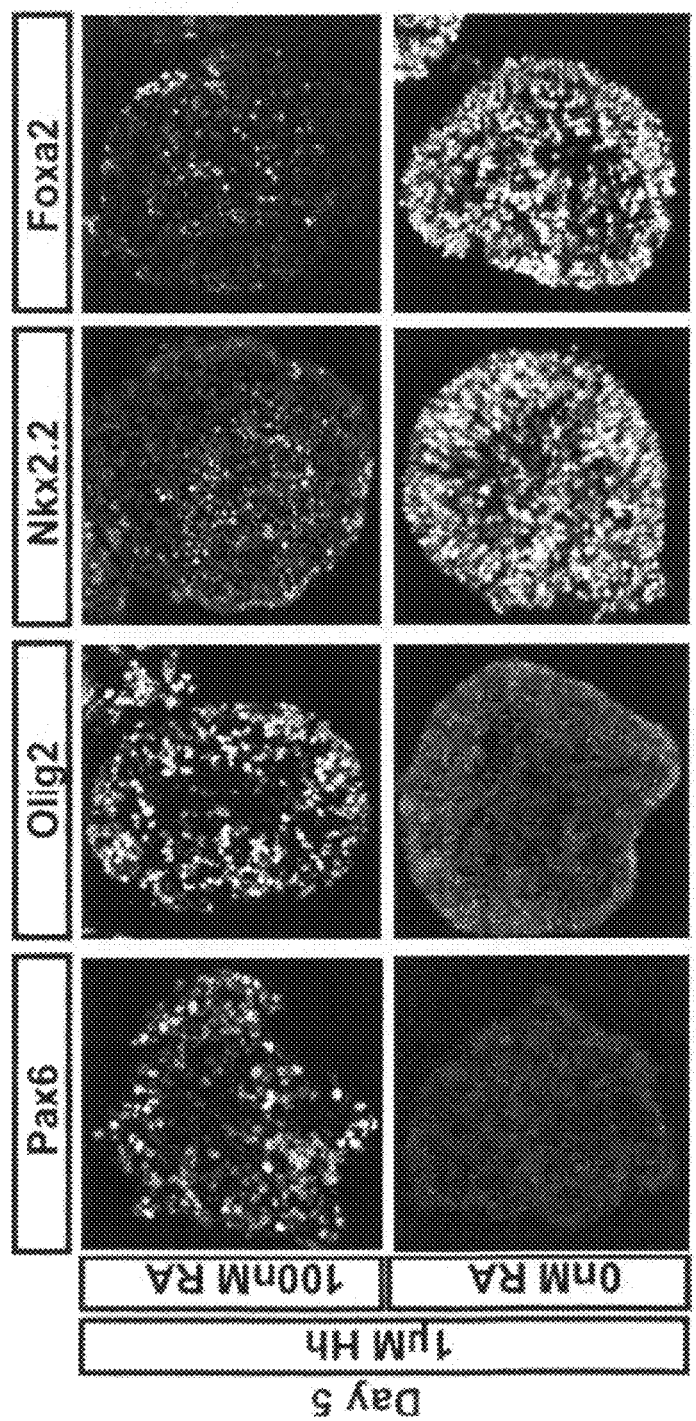
FIG. 8: shows that the expression of dorsal and intermediate spinal progenitor markers (Pax7 and Pax6) as well as MN progenitor marker Olig2 was not detected in 1 μM concentration of HhAg1., while most cells within embryoid bodies expressed the ventral-most markers Nkx2.2 and Foxa2 (Hnf3β).

The failure to generate motor neurons at high HhAg1.3 concentrations (>500 nM) could either result from incorrect DV patterning of neural progenitors or it could be caused by toxicity of HhAg1.3. To determine whether motor neuron progenitors are correctly specified at 1 µM concentrations of HhAg1.3 expression pattern of a series of DV progenitor markers were examined. The expression of dorsal and intermediate spinal progenitor markers (Pax7 and Pax6) as well as MN progenitor marker Olig2 was not detected under these conditions while most cells within embryoid bodies expressed the ventral-most markers NKx2.2 and Foxa2 (Hnf3β) (FIG. 8). This indicates that ES cells differentiating in the absence of RA are more sensitive to the activation of Hh signaling, and program of MN specification is likely interrupted by Nkx2.2 repressor activity.

Appearance of MN in EB cultured in the absence of HhAg1.3 on the other hand indicated that differentiating EBs might contain endogenous signaling centers secreting Shh. Treatment of differentiating EBs with specific Hh antagonist (Williams et al., 2003) on Day 2 resulted in the loss of expression of ventral progenitor markers (Nkx2.2, Olig2) and concomitant appearance of cells expressing dorsal spinal marker Pax7 (FIG. 2C). Failure to ventralize EBs resulted in a complete loss of MNs, demonstrating that endogenous Hh signaling is required for MN specification (FIG. 2C). The endogenous Shh signaling centers have been identified as clusters of Foxa2+ cells expressing Shh (FIG. 2D). MN progenitors marked by Olig2 expression and earliest born MNs marked by GFP expression were observed in the vicinity of these signaling centers. A subset of Foxa2 positive cells co-expressed Brachyury, (FIG. 2D) an axial mesodermal marker, suggesting that both notochord- and floor plate-like cells might organize EBs and control MN specification.

In summary, a new culture condition required for differentiation of mouse ES cells into caudal brachial MNs was identified. Embryonic stem cell-derived neural progenitors are caudalized by combined actions of Wnt and FGF signals to confer caudal brachial identity on a subset of differentiating ES cells. Endogenous Shh signal subsequently specifies motor neuron identity in a process that mimics normal development and patterning of neural tissue in vivo.

Expression Profile of Hox Proteins in ES Cell-Derived MNs

Rostrocaudal and subtype identity of spinal motor neuron is defined by a complex combinatorial code of Hox proteins. As individual Hox genes are expressed in a spatially co-linear pattern along the rostro-caudal aspect of the neural tube, many combinations of Hox protein co-expressions are not observed in vivo. Using a set of antibodies raised against individual Hox proteins, this study examined whether the pattern of Hox gene expression in MNs induced and specified in vitro corresponds to naturally occurring combinations and whether specific rostrocaudal positional identity can be assigned to ES cell-derived MNs.

Figure 3A:
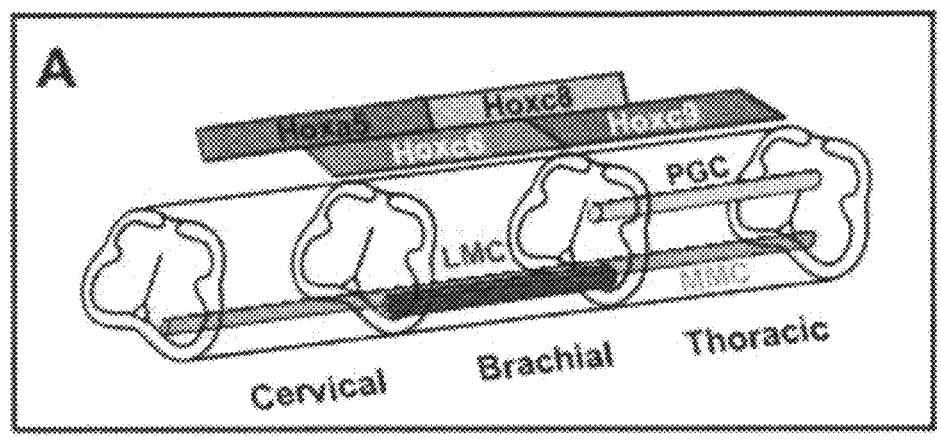
Figure 3B:
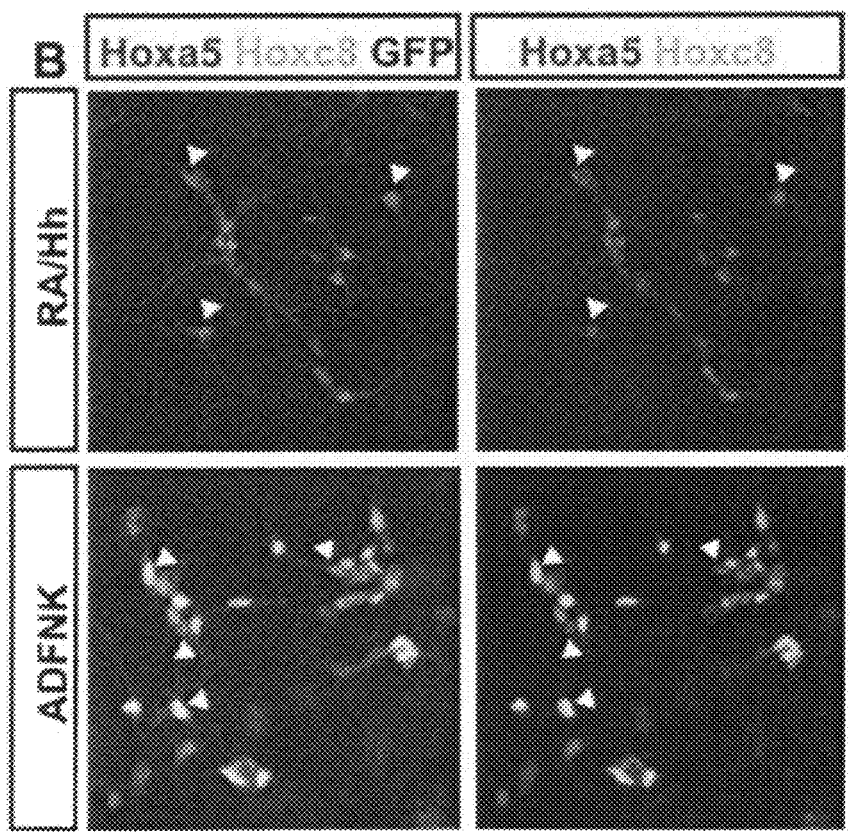

The brachial spinal cord is subdivided into the rostral and caudal sub-segments. MNs within the rostral sub-segment co-express Hox5 and Hox6 paralogous genes, while caudal brachial MNs co-express Hox6 paralogs with Hoxc8, (FIG. 3A). To determine segmental and sub-segmental identities of MNs generated under the ADFNK condition, EBs were dissociated into single cells and plated at a density at which co-expression of individual Hox genes can be unambiguously determined. When ES cells were differentiated in the presence of RA and Hh, ~89% of MNs became Hoxa5+ and no Hoxc8+ MNs were detected (FIG. 3B, D). In contrast, only ~17% of MNs generated in ADFNK expressed Hoxa5 while 64% MNs acquired expression of Hoxc8 protein, (FIG. 3B, D).

An important mechanism ensuring correct RC patterning of the developing spinal cord is mutually exclusive expression of pairs of Hox genes (Hoxa5/Hoxc8; and Hoxc6/Hoxc9) that defines segmental and intrasegmental boundaries. Similar exclusive pattern of Hox gene expression has been observed in ES cell-derived MNs (FIG. 3D). While majority of Hoxc8 positive MNs are found within the caudal brachial spinal cord, Hoxc8 extends to the first thoracic segment where it is co-expressed with Hoxc9 transcription factor (FIG. 3A). Among all in vitro generated Hoxc8 positive MNs approximately ~28% co-expressed thoracic marker Hoxc9 and ~30% co-expressed Hoxc6. As Hoxc6 is selectively down-regulated in a subset of brachial Hoxc8+ MNs, up to 70% of Hoxc8 positive MNs acquired caudal brachial identity (Hoxc8+/Hoxc9−) (FIG. 3C-D). Thus, in contrast to RA driven generation of Hoxa5+ cervical MNs, ES cells differentiation in ADFNK conditions results in generation of a significant fraction of MNs acquiring caudal brachial identity. Importantly, in vitro generated MNs exhibit mutually exclusive expression of Hox genes defining principal spinal boundaries, arguing that the program of rostrocaudal patterning of in vitro generated motor neuron is executed correctly.

ES Cell-Derived Brachial MNs Acquire MC and LMC Columnar Identities

Figures 3E, 3F, 3G, 3H:
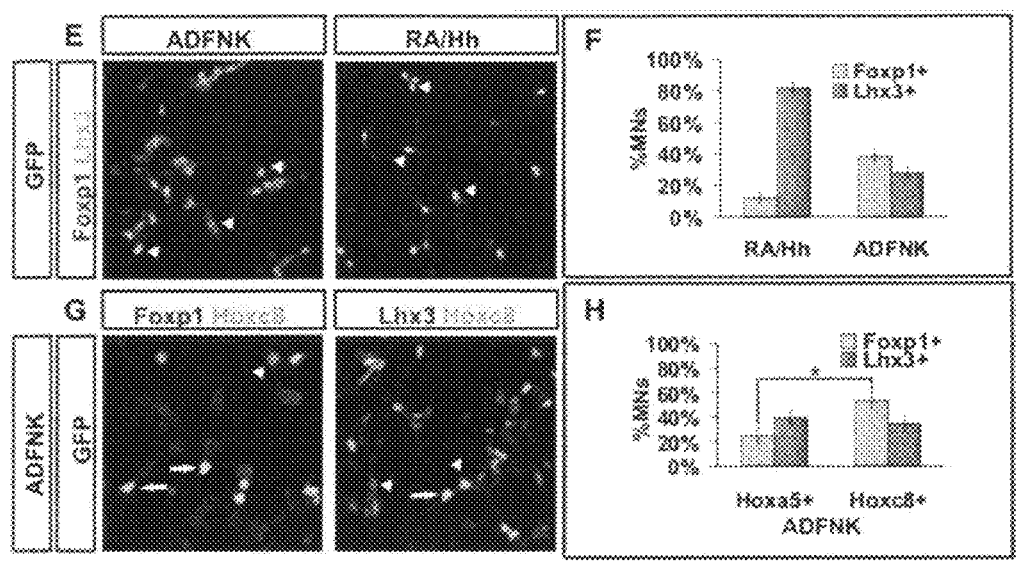
FIGS. 3E-H show that ES cell-derived brachial MNs acquire MMC and LMC columnar identities.

The emergence of the LMC motor column that harbors limb-innervating MNs is a specific feature of the brachial and lumbar spinal segments. To determine whether acquisition of brachial segmental identity is accompanied by specification of LMC MNs this study examined the expression patter of LMC specific marker Foxp1 (Tamura et al., 2003) and MMC marker Lhx3, (Sharma et al., 1998). In accordance with their cervical identity ~83% of MNs generated in the presence of RA and Hh retained expression of MMC marker Lhx, (FIG. 3E-F). In contrast, only 28% of ADFNK MNs expressed Lhx3 while 38% of MNs were Foxp1 positive and downregulated expression of Lhx3, suggesting that a significant fraction of ADFNK MNs acquire LMC identity (FIG. 3E-F). In addition, number of ADFNK MNs expressed RALDH2, a gene transiently expressed by LMC motor neurons in chick and mouse (Sockanathan and Jessell, 1998) (data not shown). Interestingly, ~54% of Hoxc8+ MNs expressed Foxp1, while only ~35% of Hoxc8 MNs expressed Lhx3, (FIG. 3G-H), supporting the notion that the majority of Hoxc8 MNs acquired caudal brachial rather than rostral thoracic identity. These results suggest that specification of brachial segmental identity during in vitro differentiation of ES cells is accompanied with corresponding acquisition of LMC columnar identity. In addition, non-overlapping expression of Foxp1 and Lhx3 markers in brachial MNs suggests that appropriate segregation of columnar identities occurs in ES cell-derived spinal MNs.

Transplanted Brachial LMC MNs Settle Correctly in the Lateral Aspect of the Ventral Horn While both LMC and MMC MNs are generated in the brachial spinal cord, MMC MNs settle ventral-medially while LMC MNs migrate to the lateral aspect of the ventral horn and form separate motor column. As neuronal migration depends on environmental cues and cytoarchitecture of neural tissue, the most informative way to assess migratory properties of in vitro generated neurons is by transplantation into the developing neural tube. To circumvent the inaccessibility of mammalian embryo for such manipulation, mouse ES cell-derived brachial MN progenitors were transplanted in the developing chick neural tube (Soundararajan et al., 2006; Wichterle et al., 2002).

ES cells differentiated in ADFNK condition to motor neuron progenitors were implanted into the developing chick brachial neural tube at a time when endogenous motor neuron progenitors are fully specified (Hamburger-Hamilton (HH) stage 15-16). Transplanted chick embryos were harvested and analyzed two days later, when differentiation and migration of endogenous motor neuron is completed. Examination of columnar subtype identity of transplanted MNs marked by GFP expression revealed that while most MMC MNs remained in the proximity of the spinal canal, a significant fraction of Foxp1+LMC MNs migrated to the lateral margin of the developing ventral horn to a position occupied by endogenous LMC MNs. These results indicate that in vitro generated MNs acquire not only molecular properties of MMC and LMC spinal MNs but they are able to correctly interpret environmental cues to settle in correct spinal columns upon implantation into the developing brachial spinal cord.

Brachial LMC MNs Exhibit Correct Axonal Pathfinding Behavior to Innervate Limb Musculature Upon Transplantation into Chick Spinal Cord LMC and MMC motor axons exit the spinal cord together via the ventral root. However, their trajectories soon diverge as MMC axons make a sharp dorsal turn to circumnavigate the dorsal root ganglion and innervate axial muscles while LMC axons continue to grow distally to innervate the developing limb bud. To determine whether in vitro generated cervical and brachial MNs exhibit distinct axon pathfinding preference, An ES cell line was generated that expressed the red fluorescent protein (RFP) mCherry (Shaner et al., 2004) under the control of MN specific promoter Hb9 (Arber et al., 1999). Hb9-RFP ES cells differentiated to cervical MNs in the presence of RA and Hh were mixed with Hb9-GFP brachial MNs differentiated in ADFNK medium and transplanted into the chick brachial neural tube (FIG. 4A-B). Two days after transplantation the columnar identity and axonal projections of the two cell populations were examined.

Transplanted cells maintained their columnar identity in vivo, with a majority of RFP+ cervical MNs expressing MMC marker Lhx3 and a significant fraction of FGP+ brachial MNs expressing LMC marker Foxp1, (FIG. 4C, D). Axon pathfinding preference of RFP+ and FGP+ MNs was quantified by measuring red and green fluorescence intensities in axial and limb branches of motor nerves (FIG. 4E). Consistently it was observed across all examined embryo the cervical (RFP+) and brachial (GFP+) motor axons exhibit distinct pathfinding preference at the axial nerve branch point, (FIG. 4F). Preferential innervations of the limb nerve branch by GFP positive brachial MNs indicates that ES cell-derived LMC MNs might selectively innervate the limb mesenchyme. The interpretation of the result is complicated by the fact that brachial MNs constitute a mixture of MMC and LMC MNs and the above experiment did not examine columnar identity of axially and limb innervating MNs.

Correlation of MN columnar identity and axon pathfinding preference as determined by retrograde tracing of motor axon would unequivocally resolve whether in vitro generated LMC MNs acquired receptors and intracellular signaling properties that enable them to follow proper axonal trajectory towards the limb mesenchyme. Hb9-GFP ES cells differentiated into brachial MNs and transplanted into the brachial spinal cord were retrogradely labeled with rhodamine-dextran (RhD) either from the axial or limb motor nerve branch, (FIG. 5). Columnar identity of backfilled transplanted MNs was examined and compared to the identity of backfilled endogenous MNs and to the identity of transplanted MNs that failed to be backfilled.

Figure 5A:
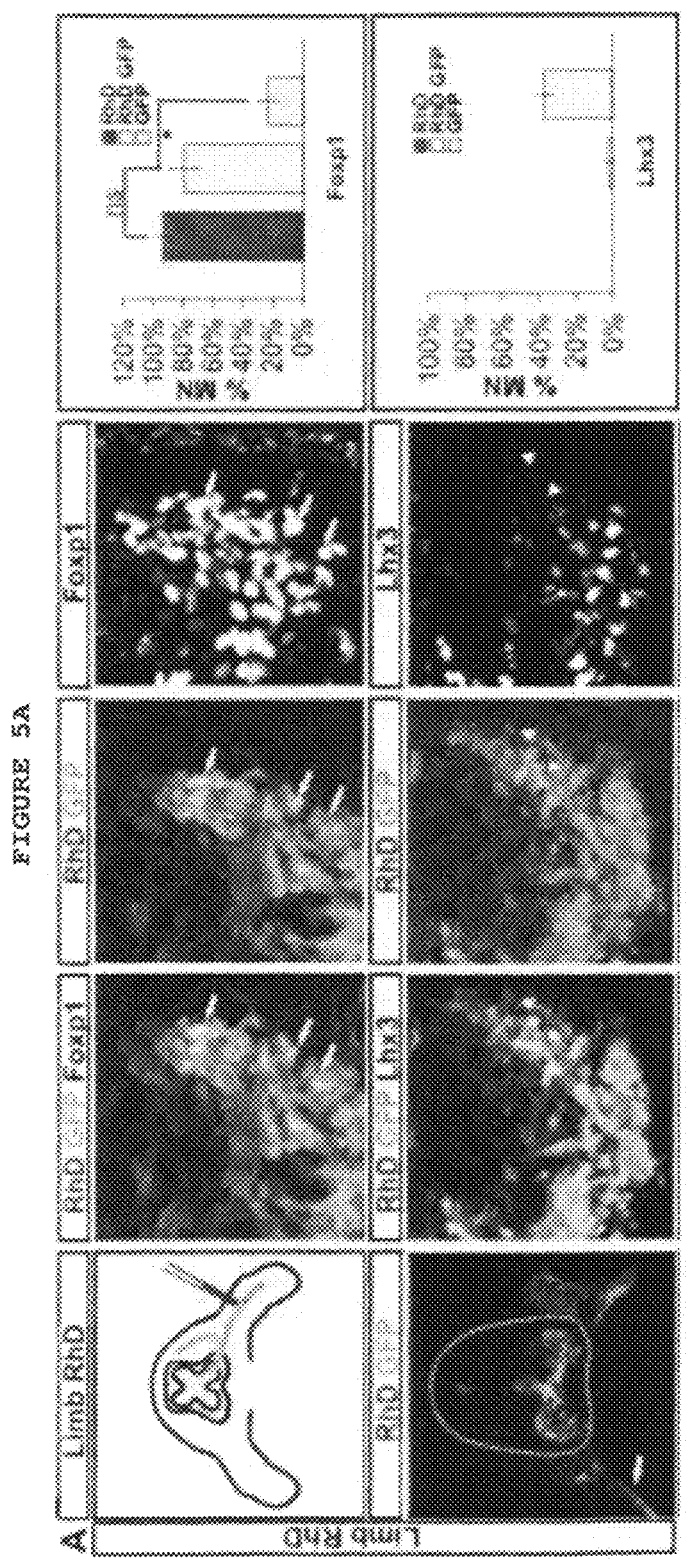
FIG. 5A shows endogenous as well as transplanted MNs retrogradely labeled from the limb nerve branch were preferentially of LMC identity as revealed by their expression of Foxp1.
Figure 5B:
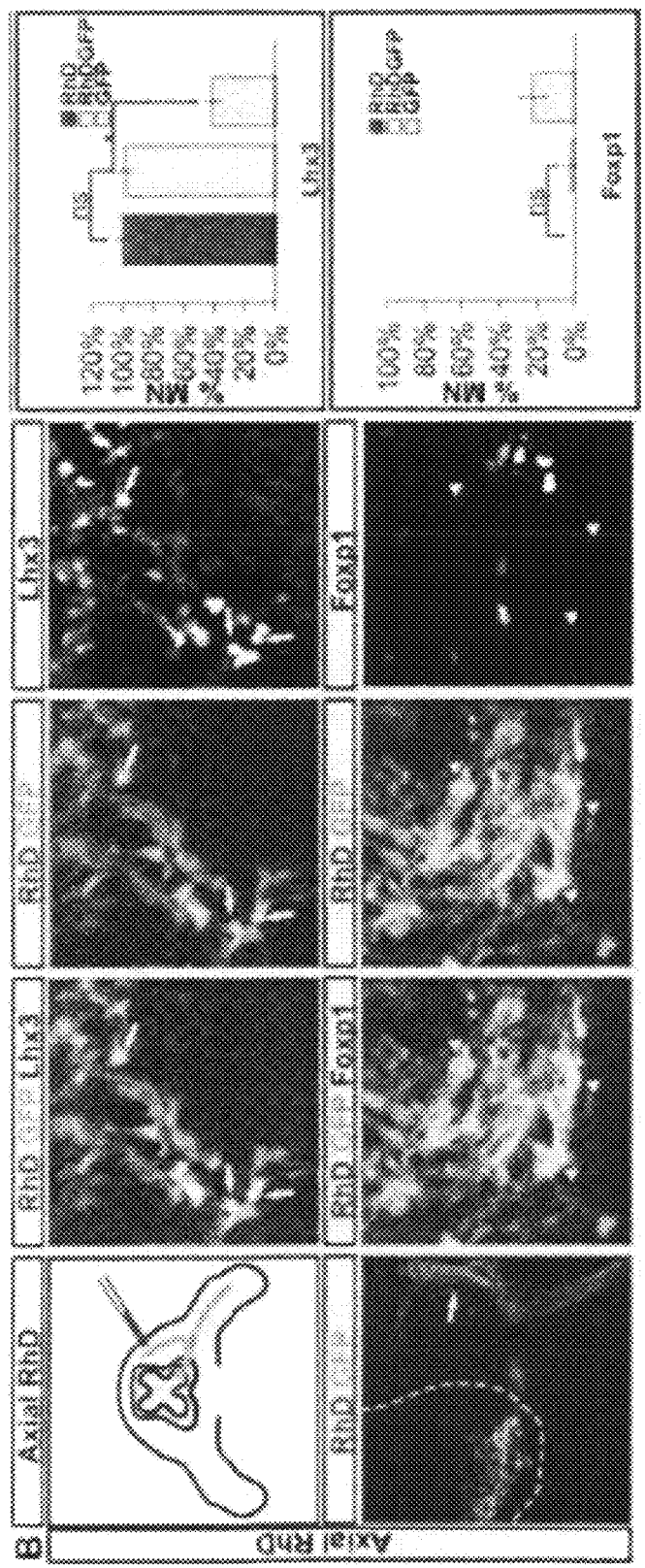
FIG. 5B shows nearly all endogenous and transplanted MNs projecting into the chick axial nerve branch were Lhx3+.

First, nearly all endogenous and transplanted MNs projecting to the chick axial nerve branch were Lhx3+, (FIG. 5B). Second, transplanted LMC MNs exhibit the correct pathfinding preference to avoid axial nerve branch that is not statistically different (p>0.05) from the pathfinding preference of endogenous LMC MNs. Third, the distribution of columnar markers in backfilled and non-backfilled transplanted MNs was significantly different. Conversely, endogenous as well as transplanted MNs retrogradely labeled from the limb nerve branch were preferentially of LMC identity as revealed by their expression of Foxp1, (FIG. 5A). Only a small number of transplanted Lhx3+ MNs projected towards the limb muscle. Together these results indicate that both brachial LMC and MMC MNs generated in vitro acquire the ultimate columnar subtype characteristics including receptor expression profiles necessary for correct interpretation of relevant axon guidance cues.

Caudal Brachial LMC MNs Acquire Properties of CM and FCU Motor Pools

Figures 6A, 6B, 6C:
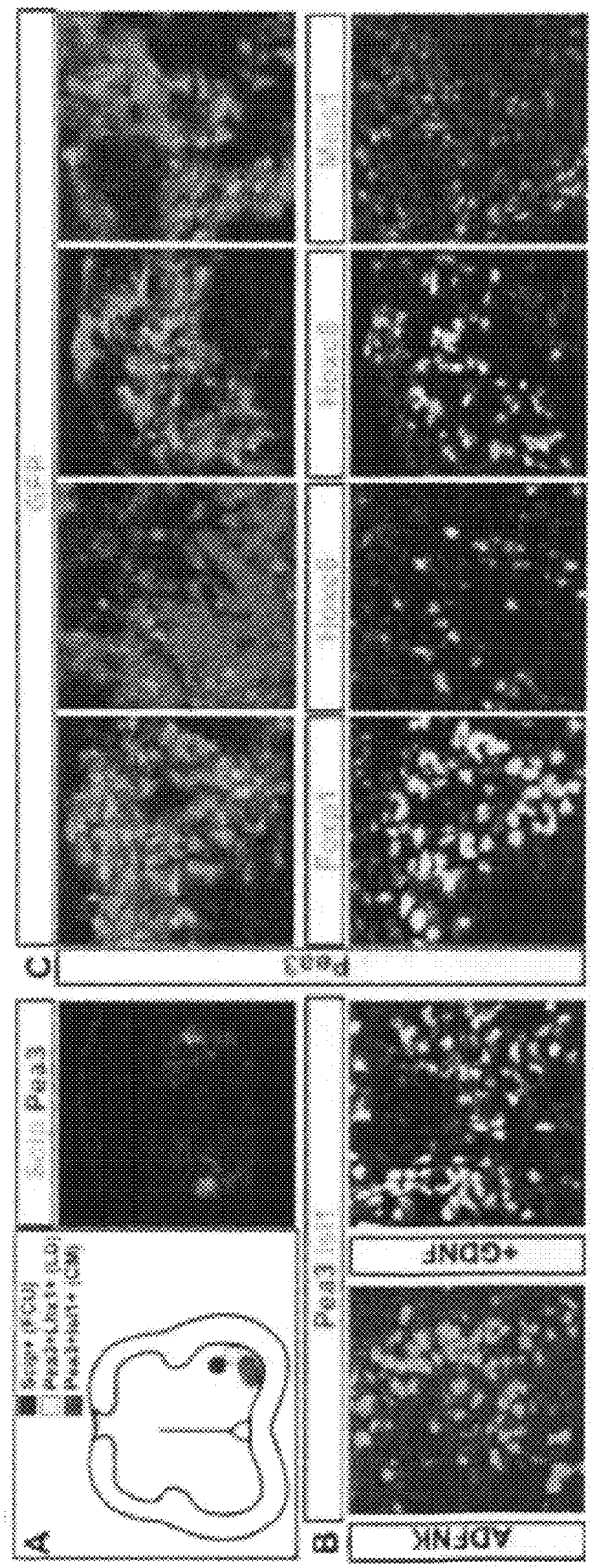
FIG. 6B shows that no Pea3+MNs were detected among caudal brachial MNs differentiated in the absence of exogenous GDNF.
Figure 9:
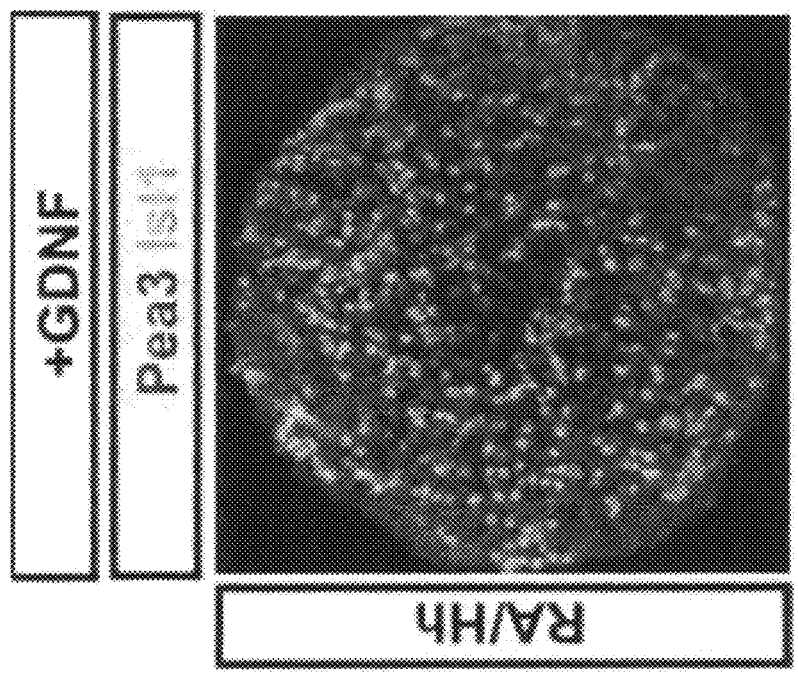
FIG. 9: shows that the induction of Pea3 expression was dependent on subtype specification of MNs, as no Pea3 expression MNs were detected among cervical MNs treated with GDNF.
Figure 10:
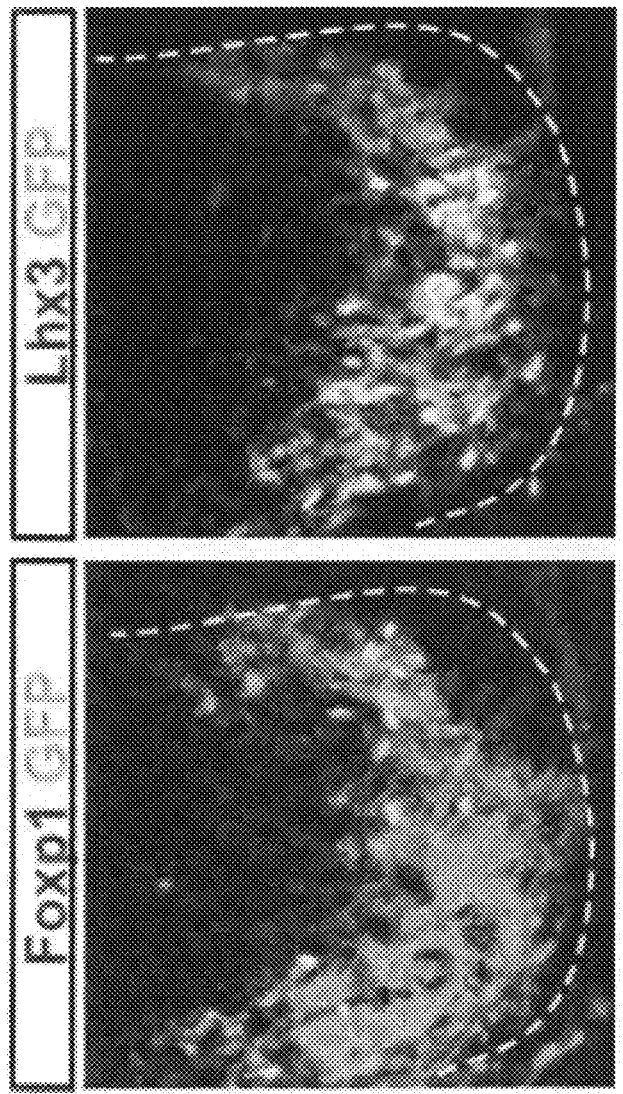
FIG. 10: compares side-by side cervical (GFP+) motor neurons' expression of MMC marker Lhx3 and LMC marker Foxp1.
Figure 11:
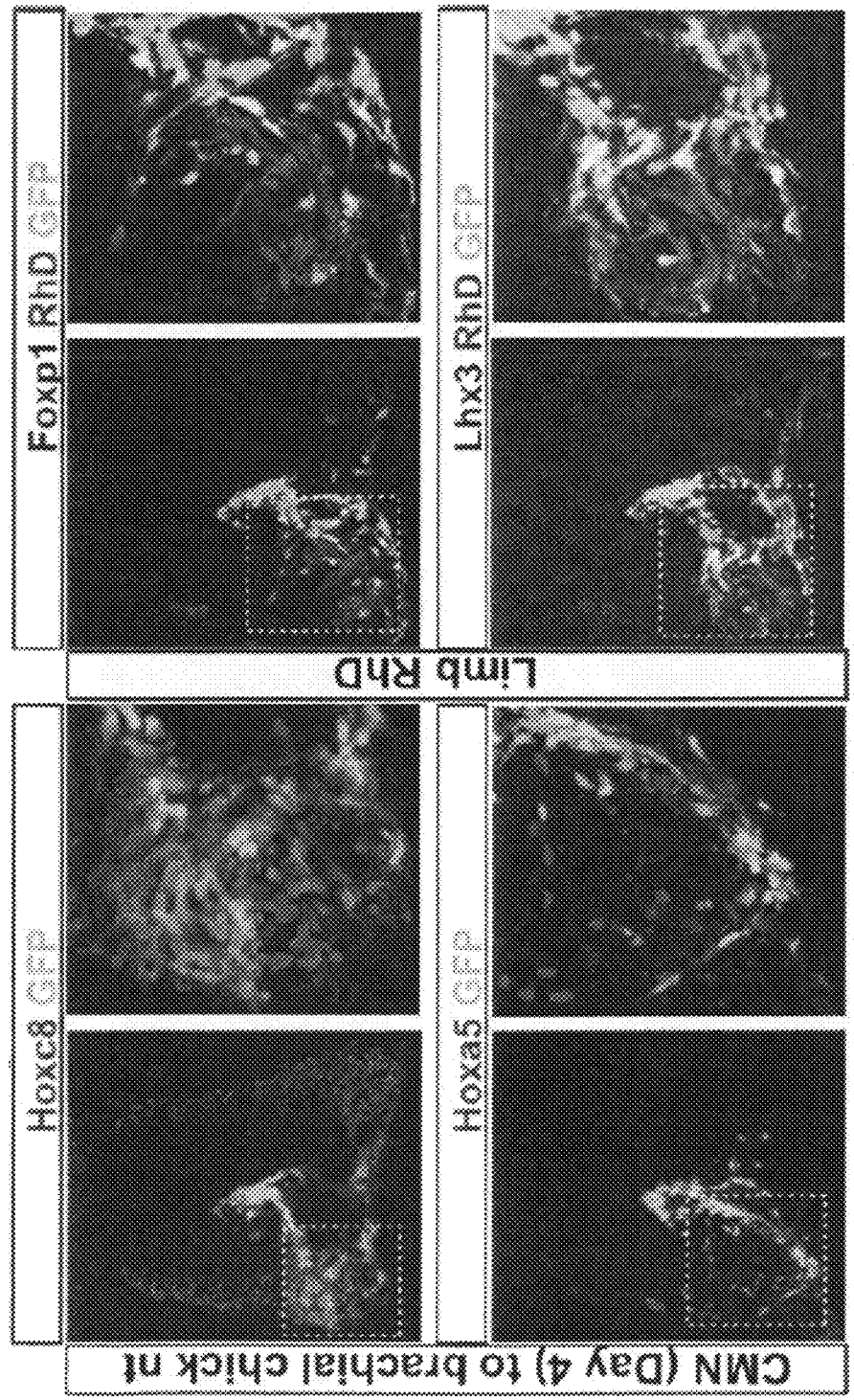
FIG. 11: shows the expression of Hxc8, Hoxa5, Foxp1 and Lhx3 of transplanted motor neurons.

Emergence of LMC motor neurons prompts examination of whether in vitro generated MNs can acquire motor pool identities specifically found in the brachial spinal cord. Three prominent motor pools innervating CM, LD and FCU muscles are found in Hoxc8+ caudal brachial spinal cord that can be distinguished by their expression of Pea3, Pea3/Lhx1 and Scip transcription factors, respectively. Pea3 expression in CM and LD motor pools depend on glial cell line-derived neurotrophic factor (GDNF), a peripheral signal received by motor axons as they extend towards the limb mesenchyme (Haase et al., 2002) In vitro generated brachial motor neurons demonstrate similar responsiveness to GDNF signal. No Pea3 positive MNs were detected among caudal brachial MNs differentiated in the absence of exogenous GDNF, (FIG. 6B). Consistent with in vivo observation, supplementing ES cell-derived caudal brachial MNs on Day 5 of differentiation with 10 ng/ml of GDNF resulted in a robust induction of Pea3 expression in a subset (~20%) of LMC MNs (FIG. 6B, D). Importantly, induction of Pea3 expression was dependent on subtype specification of MNs, as no Pea3 expressing MNs were detected among cervical MNs treated with GDNF (FIG. 9).

Figures 6E, 6F, 6G:
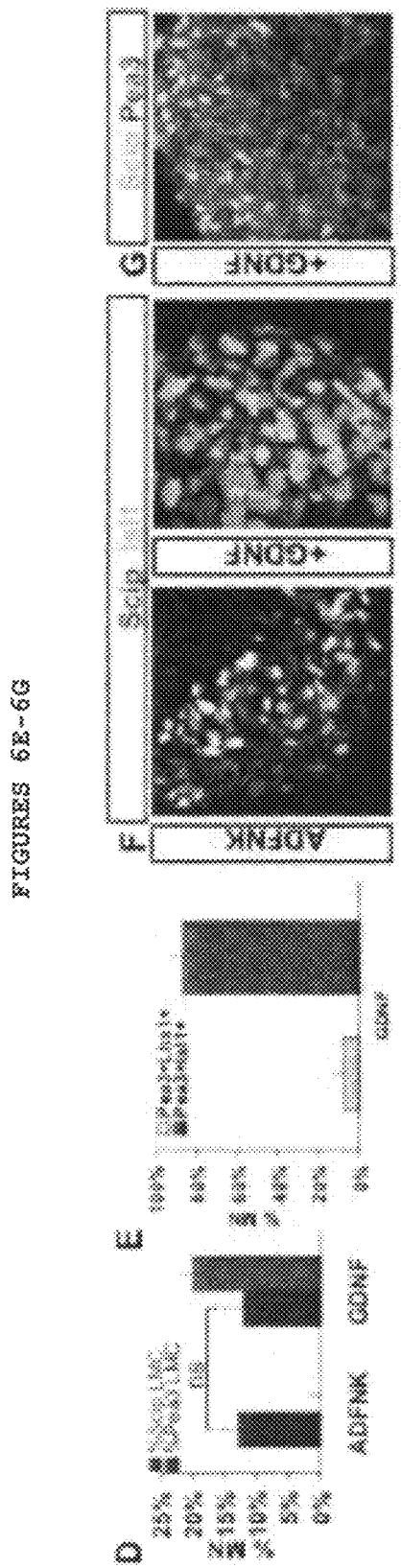

Correct specification of brachial motor pool identity depends on a combinatorial pattern of Hox and LIM transcription factor expression. As observed in vivo, all Pea3+ MNs co-express Hoxc8 and Hoxc6 while they are negative for Hox cofactor Meis1. Moreover, Pea3+ MNs belonging to CM motor pool and LD motor pool can be distinguished from each other by mutually exclusive expression of Isl1 and Lhx1, respectively (Dasen et al., 2050). Nearly 90% of Pea3+ MNs expressed Isl1+ while less than 10% express Lhx1, (FIG. 6E), indicating that majority of Pea3 expressing MNs likely belong to the CM motor pool.

Besides Pea3, ~13% of brachial MNs expresses FCU marker Scip. While Scip expression is not dependent on GDNF signaling it is expressed in a mutually exclusive manner with Pea3, (FIG. 6D, F-G), suggesting that proper segregation of motor-pool identities occurs in vitro. Interestingly, in the absence of exogenous GDNF, brachial MNs that would normally express Pea3 are not re-specified into Scip+ MNs as the percentage of Scip+ MNs in the presence or absence of GDNF is not significantly different, (FIG. 6D). Taken together, these findings indicate that generation of LMC motor neurons in vitro is accompanied with acquisition of segmentally appropriate motor pool subtype identities.

Discussion

Specification of defined neuronal subtypes in vitro remains one of the greatest challenges for efficient and sensible use of embryonic stem cells to study mammalian development, neuronal connectivity and to pioneer cell based therapies for neurodegenerative diseases. Here it is demonstrated that in vitro generated MNs can be directed to acquire cervical, brachial, thoracic or lumbar segmental identities. Comparison of ES cell-derived cervical and brachial MNs demonstrate that rostro-caudal patterning is accompanied with acquisition of MN subtype identities found at corresponding spinal segments. Finally, transplantation studies confirm that in vitro generated MNs not only acquire correct transcription profiles but they also exhibit appropriate cell body migration and axonal pathfinding preferences, indicating that stem cell-derived nerve cells are capable of terminal maturation into functionally relevant neuronal subtypes.

By employing differentiation conditions that do not rely on retinoid signaling for neural induction, the effect of exogenous and endogenous patterning signals on differentiating ES cells can be examined. It was demonstrated that ES cells cultured in ADFNK medium acquire predominantly caudal brachial identity, characterized by the expression of Hoxc8 transcription factor. Caudalization of embryoid bodies is dependent on a combined action of Wnt and FGF signals. Since media used for differentiation of ES cells are not supplemented with these factors, endogenous signals expressed by differentiation cells are deemed to be the principal caudalizing agents. Indeed, transcripts of FGF-4, FGF-5, Wnt3 and Wnt8A are detected on day 2 of differentiation, at the time of rostro-caudal patterning of EBs ((Lako et al., 2001; Stpyridis et al., 2007); data not shown).

ES cells differentiating in absence of exogenous factors provide a convenient platform to test the role of signaling molecules implicated in the patterning of chick neural tube into discreet spinal segments. Using expression of Hox genes as a molecular readout of rostro-caudal positional identity, it was demonstrated that application of RA, FGF-2, or Gdf11 can shift the rostrocaudal segmental identity of ES cell-derived MNs and specify cervical, thoracic or lumbar spinal territories, respectively. Thus, it is established that key aspects of mammalian spinal cord patterning and development can be effectively modeled in differentiating ES cells in vitro. It was demonstrated that factors controlling spinal patterning in the developing avian embryos are evolutionarily conserved and can fulfill similar patterning function during mammalian spinal cord development.

Specification of motor neuron subtype identity is controlled by a complex transcriptional network that defines connectivity and functionality of individual motor neuron subtypes. Importantly, only a relatively small subset of all possible combinations of transcription factor expression is observed in postmitotic MNs in vivo. Indeed, number of transcription factors exhibit mutually repressive interactions that ensure their segregation into distinct sets of neurons. Combinatorial transcription code defining motor neuron subtype identity has been well characterized for several groups of brachial motor neurons. For example, CM motor neurons are defined by their expression of Isl1, Foxp1, Hoxc6, Hoxc8 and Pea3 in absence of Hoxc5, Lhx3, Hb9, Meis1, and Scip. The molecular identity of in vitro generated CM motor neurons (defined by co-expression of Pea3 and Isl1) is apparently indistinguishable from the identity of endogenous CM motor pool. Correct specification of CM MN was further demonstrated by their unique response to muscle-derived GDNF signal that elicits induction of Pea3 expression only in the context of specified CM MNs. Thus, based on a combinatorial expression of ~10 transcription factors and a unique responsiveness to GDNF signal the inventors conclude that ES cells differentiated into brachial motor neurons in vitro acquire correct identity of principal MN subtypes found in the brachial spinal cord in vivo.

These data support establishment of RC identity of neural progenitors as initiating largely cell autonomous programs that yield a diverse, segmentally appropriate set of motor neurons. Thus far, the segmental identity of motor neurons as defined by Hox gene expression from their columnar and motor pool subtype identity is still not dissociated, thus strengthening the proposed central role of Hox factors in the establishment of MN subtype diversity. This observation is the first to suggest that distinct and defined subtypes of nerve cells can be effectively derived in vitro from ES cells.

Correct transcriptional identity of in vitro differentiated cells does not necessarily mean that the cells acquire other critical biochemical properties necessary for their subtype-specific migration and axon pathfinding properties. The fact that cells were generated expressing molecular properties of LMC motor neurons allows for direct comparison of migratory and axon outgrowth behavior of in vitro differentiated MMC and LMC MNs. MNs belonging to the same motor pool are initially specified in a salt and pepper manner in the developing spinal cord. However, concomitant with motor axon outgrowth motor neural belonging to the same motor pool coalesce into discreet clusters in vivo. While in vitro specified MNs exhibit correct expression of all motor pool specific markers, their cell bodies do not cluster. Such failure to cluster could be caused either by incorrect expression of cell surface molecules (such as Type II cadherins (Price et al., 2002)) or by aberrant geometry or microenvironment within embryoid bodies.

To examine behavior of MNs in a more natural environment in vitro generated murine MNs were implanted into the developing chick neural tube at the time of endogenous motor neuron generation. LMC MNs exhibited correct migratory tendency to settle in the lateral horn and motor pool clustering. Importantly, axonal retrograde tracing experiments demonstrated that even in the context of xenografts LMC and MMC MNs exhibited correct axon pathfinding preferences to innervate the limb and axial muscles. The striking specificity of axonal projections suggests that molecular specification of MN subtype identity is accompanied with expression of correct biochemical machinery to recognize and navigate relevant axon guidance cues.

Example 2

The generation of diverse neuronal subtypes relies on a precisely orchestrated interplay between extrinsic signaling factors and intrinsic transcriptional programs. This experiment shows 1) that mouse embryonic stem (ES) cells can be induced to differentiate into distinct spinal motor neuron (MN) subtypes by extrinsic signals that pattern the rostro-caudal and dorsoventral axis in vivo; 2) Wnt, FGF, and Hh signals induce brachial and thoracic spinal MN identities, as determined by expression of Hox proteins; 3) Many brachial ES cell-derived motor neurons (ES-MNs) expressed FoxP1, a marker of lateral motor column (LMC) neurons that innervate limb muscles; 4) When introduced by transplantation into the chick developing neural tube, ES-MNs settled in motor columnar territories and projected their axons along nerve branches in a pattern that conformed to their molecular columnar identity; 5) ES-MNs of LMC character acquired molecular properties of flexor carpi ulnaris and cutaneous maximus motor pools, and exhibited differential sensitivity to limb-derived inductive factors; and 6) Specification of motor pool identity proceeds in a cell autonomous manner; providing evidence that functional diversification of spinal MNs is determined during the initial rostro-caudal patterning of neural progenitors. These findings establish that ES-MNs can be programmed to acquire molecular and functional properties characteristic of the highly specialized MN subtypes found in vivo.

Introduction

The emergence of highly diverse and specialized cells during embryonic development relies on a series of signaling events that progressively restrict the potential fates of progenitor cells. Most organs contain only a limited repertoire of cell types, but their generation from pluripotent stem cells in vitro has nevertheless remained challenging, largely because of an incomplete understanding of patterning signals and intrinsic factors that control normal development and organogenesis. The problem of specifying cell identities is particularly daunting in the central nervous system (CNS), where several hundred major neuronal classes are generated, many of which are further diversified into even more specialized neuronal subtypes. There are at least a dozen classes of dopaminergic neurons, two dozen retinal ganglion and amacrine neuronal cell groups, several dozen spinal MN subtypes, and a thousand distinct olfactory receptor neurons (Buck and Axel, 1991; MacNeil and Masland, 1998; Rockhill et al., 2002; Liss and Roeper, 2008; Dasen, 2009). Neuronal diversity is not only essential for CNS function but often correlates with, and perhaps confers, selective vulnerability to neurodegenerative disease (Dauer and Przedborski, 2003; Boillée et al., 2006; Rosas et al., 2008).

Figure 12:
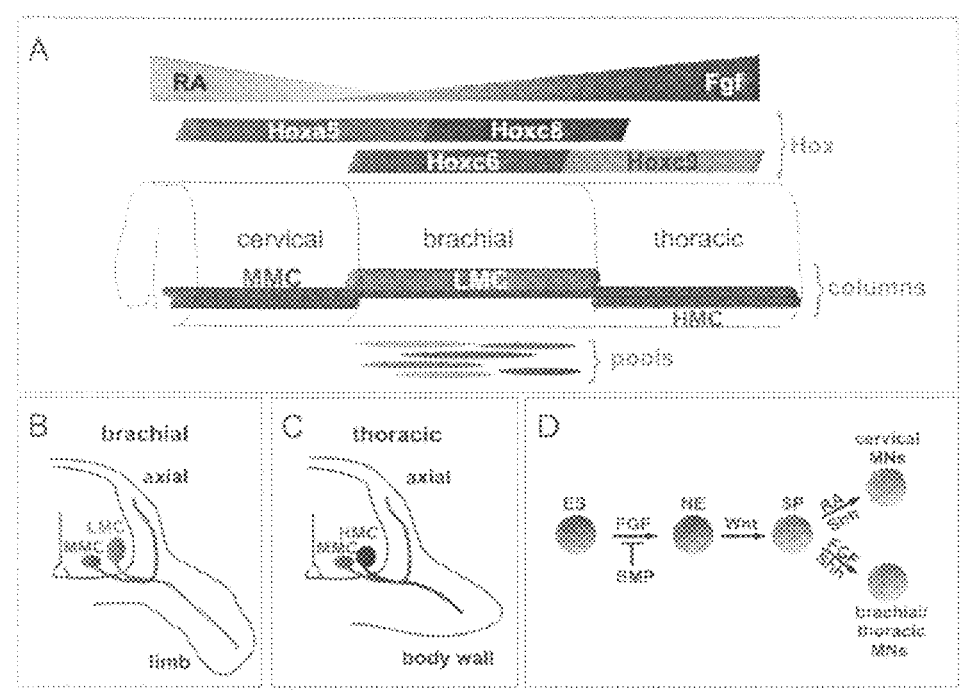
FIG. 12: Rostro-caudal Organization of Spinal MNs: A) Rostro-caudal patterning of the spinal cord is controlled by opposing RA and FGF gradients. MNs generated at defined rostro-caudal positions express unique combinations of Hox genes and are organized into discrete motor columns. MMC: median motor column; HMC: hypaxial motor column; LMC: lateral motor column. LMC neurons are organized into distinct motor pools. B) At brachial level of the spinal cord, LMC neurons innervate limb muscles and MMC neurons innervate axial muscles. C) At cervical and thoracic levels of the spinal cord, MMC neurons innervate axial muscles and HMC neurons innervate hypaxial (body wall) muscles. D) Strategy for specification of brachial and thoracic MN identities. ES cells grown in the presence of FGF and absence of BMP signals differentiate to neural ectoderm (NE). Neuralized embryoid bodies can be caudalized with canonical Wnt signals to specify generic spinal progenitors (SP). Specification of cervical and brachio-thoracic MNs is controlled by RA and FGF, in combination with ventralizing Shh signal.

Within the CNS, spinal MNs exhibit a high degree of subtype diversity (Landmesser, 2001; di Sanguinetto et al., 2008; Dasen, 2009). Molecular and histological studies of neuromuscular connectivity have revealed that distinct MN subtypes innervate individual skeletal muscle groups (Hollyday and Jacobson, 1990). The presence of well over a hundred muscle groups in the limbs and the trunk implies the existence of an equivalent number of MN subtypes. MN diversification can be deconstructed into a series of developmental events, in which 'generic' MNs progressively acquire subtype identities that match the diversity of their muscle targets (Jessell, 2000; Kania et al., 2000; Dasen et al., 2003; Sockanathan et al., 2003; Dasen et al., 2005). Spinal MNs first acquire median (MMC), hypaxial (HMC), or lateral (LMC) motor columnar characteristics that dictate MN cell body settling position and the pattern of axial, body wall and limb muscle innervation (FIG. 12A-C). LMC neurons subsequently acquire medial and lateral divisional identities that underlie their ability to innervate ventral and dorsal limb muscles, respectively (Kania et al., 2000). Subsequently, within each LMC division, neurons acquire diverse pool identities that define their connections to specific muscles in the limb.

Figure 20:
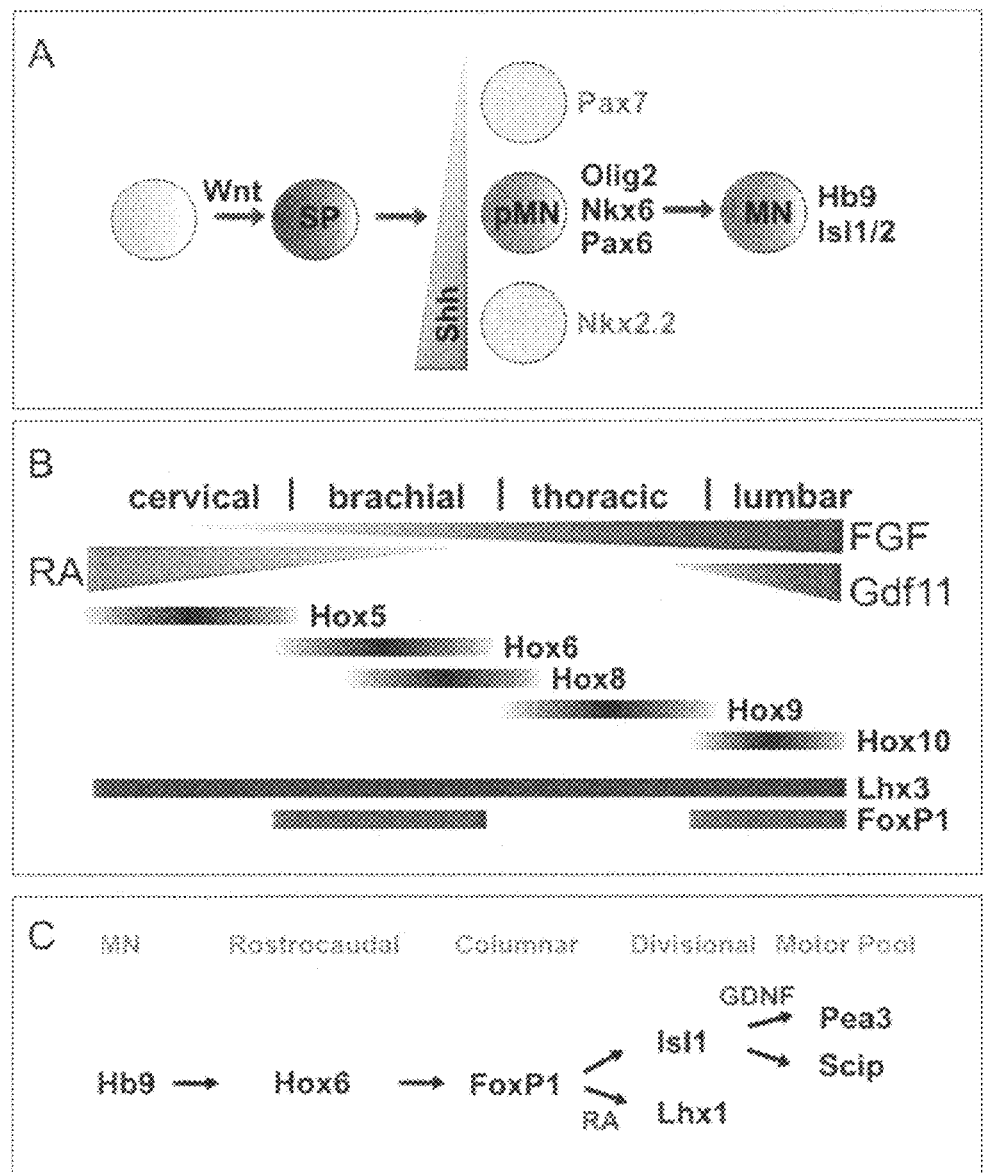
FIG. 20: Extrinsic Signals and Intrinsic Programs Controlling Generic, Rostro-caudal, and Intra-Segmental MN Subtype Identities: A) Schematic for specification of generic MN identity. Wnt signaling promotes spinal progenitor (SP) identity, while Shh directs the specification of ventral Olig2$^+$ MN progenitors (pMN) that differentiate into postmitotic Isl$^+$/Hb9$^+$ MNs. B) Rostro-caudal patterning, as determined by differential expression of Hox genes, is controlled by opposing gradients of RA and FGF that promote rostral cervical and brachial/thoracic spinal identities, respectively. FGF in combination with Gdf11 directs lumbar spinal identities (modified from Liu et al., 2001). C) Schematic of diversification of MN subtype identity. Subset of forelimb level MNs expressing Hox6 (Hoxc6 or Hoxa6) acquires the identity of limb innervating LMC neurons that express FoxP1. LMC neurons are subdivided into lateral Lhx1$^+$ and medial Isl1$^+$ divisions. Distinct motor pools within LMC can be identified by differential expression of motor pool markers (e.g. Scip and Pea3).

The question of how MNs acquire the diverse phenotypes necessary for the formation of functional motor circuits has received considerable attention. Studies in vertebrate embryos suggest that the specification of MN identity is controlled by a series of graded patterning signals. At early neural plate stages caudal canonical Wnt signals specify spinal cord character (Kiecker and Niehrs, 2001; Nordstrom et al., 2006). Spinal cells then acquire generic MN and MMC columnar identities in response to the ventral Sonic hedgehog (Shh) and non-canonical Wnt signals (Jessell, 2000; Dessaud et al., 2008; Agalliu et al., 2009) (FIG. 20A). The diversity of MN columnar, divisional and motor pool identities is controlled by rostro-caudal gradients of retinoic acid (RA) and fibroblast growth factors (FGFs) (Liu et al., 2001; Dasen et al., 2003; Sockanathan et al., 2003) (FIGS. 12A, 20B). At each stage of development, the response of progenitor cells to these extrinsic patterning signals is accompanied by the expression of cell-specific transcription factors (Jessell, 2000). Thus, inductive signals establish combinatorial profiles of transcription factor expression that determine the identity and connectivity of spinal MNs.

Molecular insight into the specification of MN subtypes poses two issues for stem cell biology: 1) whether our understanding of the developmental signals involved in the specification of MN subtype identity sufficiently advanced to direct the generation of distinct MN subtypes from pluripotent mouse embryonic stem (ES) cells; and 2) whether ES cell-derived MNs (ES-MNs) acquire highly specialized functional characters that resemble those of the diverse MN subtypes generated in vivo. Resolving these issues may help to determine how stem cell-derived neurons can contribute effectively to the study of neuronal vulnerability in neurodegenerative diseases, and whether they can serve as sources of highly-specialized neuronal subtypes for tissue repair.

Mouse and human ES cells can be efficiently converted into spinal MNs, in a process that recapitulates key aspects of embryonic MN differentiation (Wichterle et al., 2002; Li et al., 2005; Lee et al., 2007). However, the ES-MNs derived under existing conditions exhibit primarily a cervical, MMC-like identity (Wichterle et al., 2002; Soundararajan et al., 2006), and it remains unclear whether ES-MNs are able to acquire more complex subtype characters. Also, question remains whether ES cells be directed to defined MN subtypes solely by exposure to secreted signals, or is genetic manipulation and intrinsic transcriptional re-programming needed. Also still yet to be determined is the extent endogenously expressed patterning factors and cell autonomous programs involved in the differentiation process? To address these questions, this experiment aims to determine whether ES-MNs can acquire key MN subtype specific features and functions—expression of meaningful combinations of subtype specific markers, the segregation into corresponding motor columns, the projection of motor axons along appropriate peripheral paths, and the competence of MNs to respond to specific target-derived signals.

EXPERIMENTAL PROCEDURES

Differentiation of ES Cells

All experiments were performed with HBG3 ES cell line harboring Hb9-GFP transgene (Wichterle et al., 2002) and key experiments were confirmed using a control MM13 ES cell line. Differentiation of HBG3 ES cell line under RA/Hh conditions into rostral cervical MNs was performed as previously described (Wichterle et al., 2002; Wichterle and Peljto, 2008). For production of cervical MNs, ES cells were plated at 50,000 cells/ml in ADFNK differentiation medium [Advanced D-MEM/F-12 (Invitrogen): Neurobasal medium (Invitrogen) (1:1), 10% Knockout Serum Replacement (Invitrogen), 200 mM L-Glutamine (Invitrogen), 0.1 mM β-mercaptoethanol (Sigma), and Pen/Strep (Invitrogen)]. Medium was completely changed on days 1, 2 and of differentiation. EBs were split 1:4 on day 2 of differentiation and the medium was supplemented with 1 μM all-trans retinoic acid (RA, Sigma) and Hh agonist (0.5 μM SAG, Calbiochem or 1 μM HhAg1.3, (Frank-Kamenetsky et al., 2002)). To generate caudal brachial level MNs from ES cells under FGF/Hh conditions, ES cells were plated into non-adherent tissue culture dishes in ADFNK medium (~20,000 cells/ml). Embryoid bodies (EBs) were split 1:4 on day 2 of differentiation and the medium was changed on days 1, 2 and 5. Selected cultures were supplemented with the following reagents: 10 nM-1 μM RA, 10 nM-1 μM Hh Agonist, 1 μg/ml recombinant mouse Dickkopf-1 (R&D Systems), 50-100 nM FGF/VEGF Receptor Tyrosine Kinase Inhibitor (PD173074, Calbiochem) (Mohammadi et al., 1998), 100-625 ng/ml recombinant human bFGF (PeproTech), 20 ng/ml recombinant human Gdf11/Bmp11 (R&D Systems), 10 ng/ml recombinant rat GDNF (R&D Systems).

Dissociated Cultures of ES-MNs

For immunocytochemical analysis, EBs were dissociated using 0.05% Trypsin-EDTA (Invitrogen) on day 6 and plated at low density on coverslips (Carolina Biological) first coated with 0.001% solution of poly-1-ornithine (Sigma; diluted in water) and then with mouse laminin (5 ng/ml final concentration in PBS; Invitrogen). Cultures were plated and maintained using ADFNB culture medium [Advanced D-MEM/F12:Neurobasal (1:1), 1× B27 supplement (Invitrogen), 200 mM L-Glutamine, and 1× Pen/Strep]. Selected cultures were supplemented with GDNF (10 ng/ml). ES-MN cultures were fixed with 4% paraformaldehyde (PFA) for ~15 minutes at room temperature one day after plating and processed for immunocytochemistry. For quantifications of MN cultures, ~10 random fields were imaged using confocal microscope LSM Zeiss Meta 510. Expression of transcription factors in individual cells was quantified and gated to GFP$^+$ ES-MNs in at least three independent differentiation experiments. For quantifications of MN differentiation efficiency, images were acquired using Zeiss Axiovert 200M microscope and quantifications performed using MetaMorph software (Meta Imaging Series Software 7.1, Molecular Devices).

Immunocytochemistry

Immunocytochemistry on dissociated ES-MNs and cryosectioned EBs was performed as previously described (Wichterle et al., 2002). In this study, the following antibodies were used: goat anti-Meis1 (Santa Cruz Biotechnology, SCB), mouse anti-Lhx3 (Developmental Studies Hybridoma Bank, DSHB), mouse anti-Lhx1/2 (DSHB), mouse anti-Nkx2.2 (DSHB), goat anti-Hoxc6 (SCB), rabbit anti-Hoxd9 (SCB), rabbit anti-Otx2 (kindly provided by G. Corte), mouse anti-Isl1 (DSHB), mouse anti-Hoxc 8 (DSHB), mouse anti-NeuN (Chemicon), rabbit anti-dsRed (Clontech), rabbit anti-Brachyury (SCB), mouse anti-Sonic Hedgehog (DSHB), mouse anti-FoxA2 (DSHB), mouse anti-Pax7 (DSHB), mouse anti-Hb9 (DSHB), guinea pig anti-Hb9 (kindly provided by the Project ALS laboratory). In addition to the commercially available antibodies, the following previously characterized polyclonal antibodies were used (Liu et al., 2001; Novitch et al., 2003; Dasen et al., 2005): guinea pig anti-Olig2, guinea pig anti-Isl1/2, guinea pig anti-Hoxc6, guinea pig anti-Hoxa5, rabbit anti-Hoxc9, guinea pig anti-Hoxd10, rabbit and guinea pig anti-FoxP1, rabbit anti-Lhx3, rabbit anti-Pea3, guinea pig anti-Scip.

Transplantation of ES-MNs into Chick Neural Tube

Transplantation of ES cell-derived MNs into chick developing neural tube was performed as previously described (Wichterle et al., 2002; Wichterle et al., 2009).

To compare cervical and brachio-thoracic MNs the inventors introduced Hb9-mCherry transgene (Hb9-RFP line) into Olig2-GFP ES cell line (generously provided by Dr. Bennett Novitch). Hb9-RFP ES cells were differentiated in the presence of RA/Hh while Hb9-GFP (HBG3) ES cells were differentiated using FGF/Hh condition. Embryoid bodies were harvested on day 5 or day 6 of differentiation and transplanted into lesioned chick neural tube. On day 6 of differentiation, Hb9-RFP and Hb9-GFP EBs were dissociated (using Trypsin), mixed and 5000-10000 cells were reaggregated in 50 μl hanging drops (modified from Renoncourt et al., 1998). Cell aggregates were transplanted into HH stage 15-17 chick developing embryo at the brachial (somite level 13-17) or thoracic level (somite levels 17-23) of the developing spinal cord. Three days after transplantation, embryos were fixed with 4% PFA at 4° C. for ~1 hour and processed for immunohistochemistry. Quantification of axonal projections was performed by measuring the areas of GFP and RFP fluorescence in limb and axial nerve branches using Image J software (NIH, http://rsbweb.nih.gov/ij/).

Retrograde Labeling of ES-MNs

Retrograde labeling was modified from previously described methods (Dasen et al., 2005). Briefly, embryos were dissected three days post-transplantation, axial or limb GFP nerve branches were cut under a fluorescence dissection microscope and retrogradely labeled with 3000 MW lysine-fixable tetramethylrhodamine-dextran (RhD, Molecular Probes). Embryos were incubated in an oxygenated bath containing DMEM (Chemicon): F12 (Invitrogen) (1:1) and 1× Pen/Strep medium at 37° C. for 3-5 hours, then fixed and processed for immunohistochemistry. FoxP1 and Lhx3 expression levels in individual retrogradely labeled transplanted (RhD$^+$ GFP$^+$ double positive) and endogenous (RhD$^+$) MNs were analyzed using MetaMorph software.

Cell Migration Quantifications

Cryosections of chick brachial spinal cords harboring transplanted ES-MNs were immunostained for Lhx3 and FoxP1. Z-stack images of immunostained cryostat 16 μm thick sections of chick spinal cords containing GFP$^+$ transplanted MNs were acquired using LSM Zeiss Meta 510 confocal microscope. Relative medio-lateral position of endogenous and grafted MNs was measured (0 corresponds to the medial-most and 1 corresponds to the lateral-most endogenous MN) using Image J software. Grafted MNs that failed to migrate from the transplantation site near the spinal canal were not included in the analysis.

Statistical Analysis

Two-tail Student's t-test was used for statistical analysis. Relevant p-values are indicated below. *p=0.01-0.05, p=0.001-0.01, *p<0.001.

Figure 13:
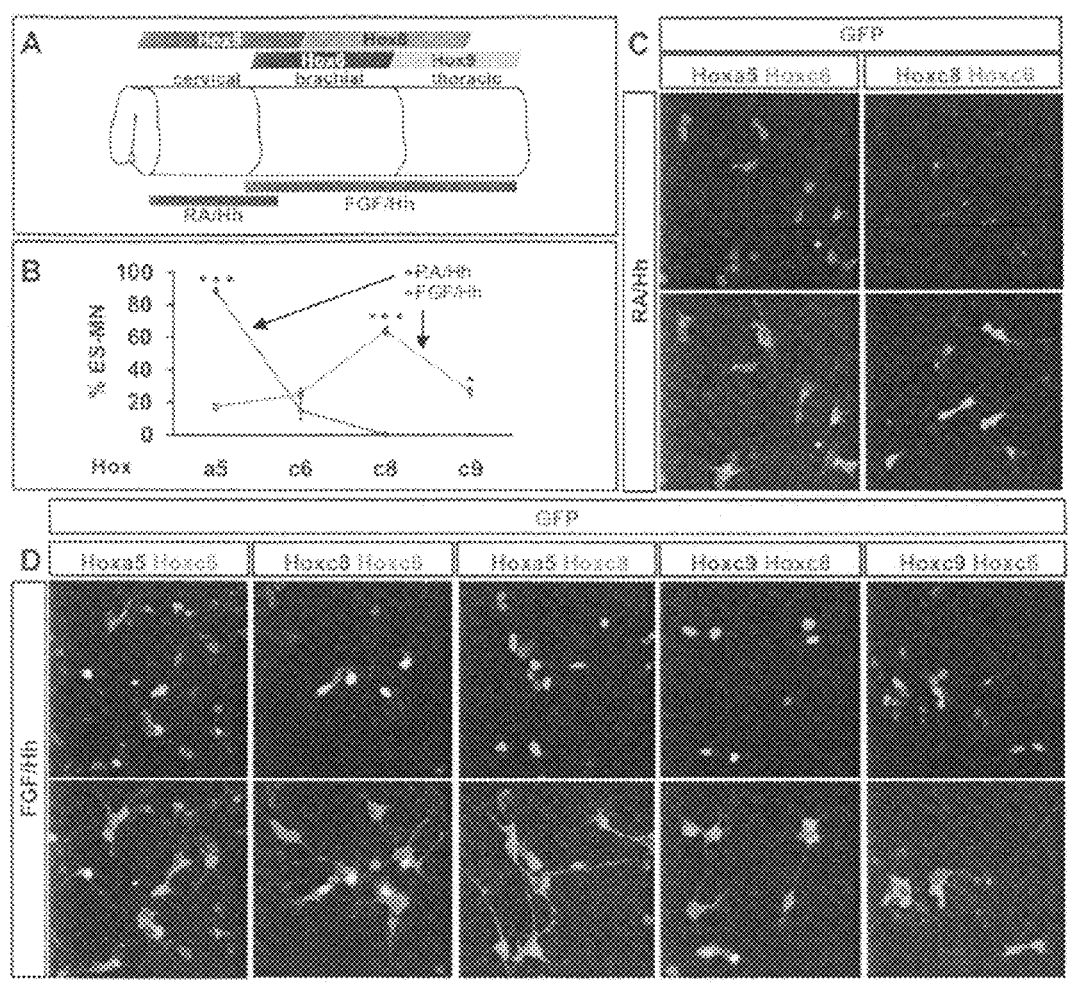
FIG. 13: Profile of Hox Gene Expression in ES-MNs: A) Summary of Hox expression in the developing spinal cord. Dark Grey and grey lines under the spinal cord represent the populations of ES-MNs derived by RA/Hh and "basal" exposure, respectively. B) Expression of individual Hox genes in ES-MNs dissociated and plated on day 6 was quantified on day 7. RA/Hh and "basal" ES-MNs (indicated by arrows) exhibit significantly different pattern of Hoxa5 ($p<0.01$), Hoxc8 ($p<0.001$) and Hoxc9 ($p=0.001$) expression. Graph represents data from three independent experiments (mean±SEM). C) RA/Hh-derived MNs express Hoxa5, low levels of Hoxc6, but no Hoxc8. D) Majority of "basal"-derived MNs express Hoxc8, while smaller subsets express Hoxa5, Hoxc6 and Hoxc9. Note mutually exclusive expression of Hoxa5/Hoxc8 and Hoxc6/Hoxc9.

| FIG. 13B (RA/Hh versus FGF/Hh), n = 3 independent experiments, ~1000 ES-MNs | | | |
|---|---|---|---|
| Hoxa5$^+$ ESMNs | Hoxc6$^+$ ESMNs | Hoxc8$^+$ ESMNs | Hoxc9$^+$ ESMNs |
| <0.0001 | 0.098 | <0.0001 | 0.010 |

Figure 14:
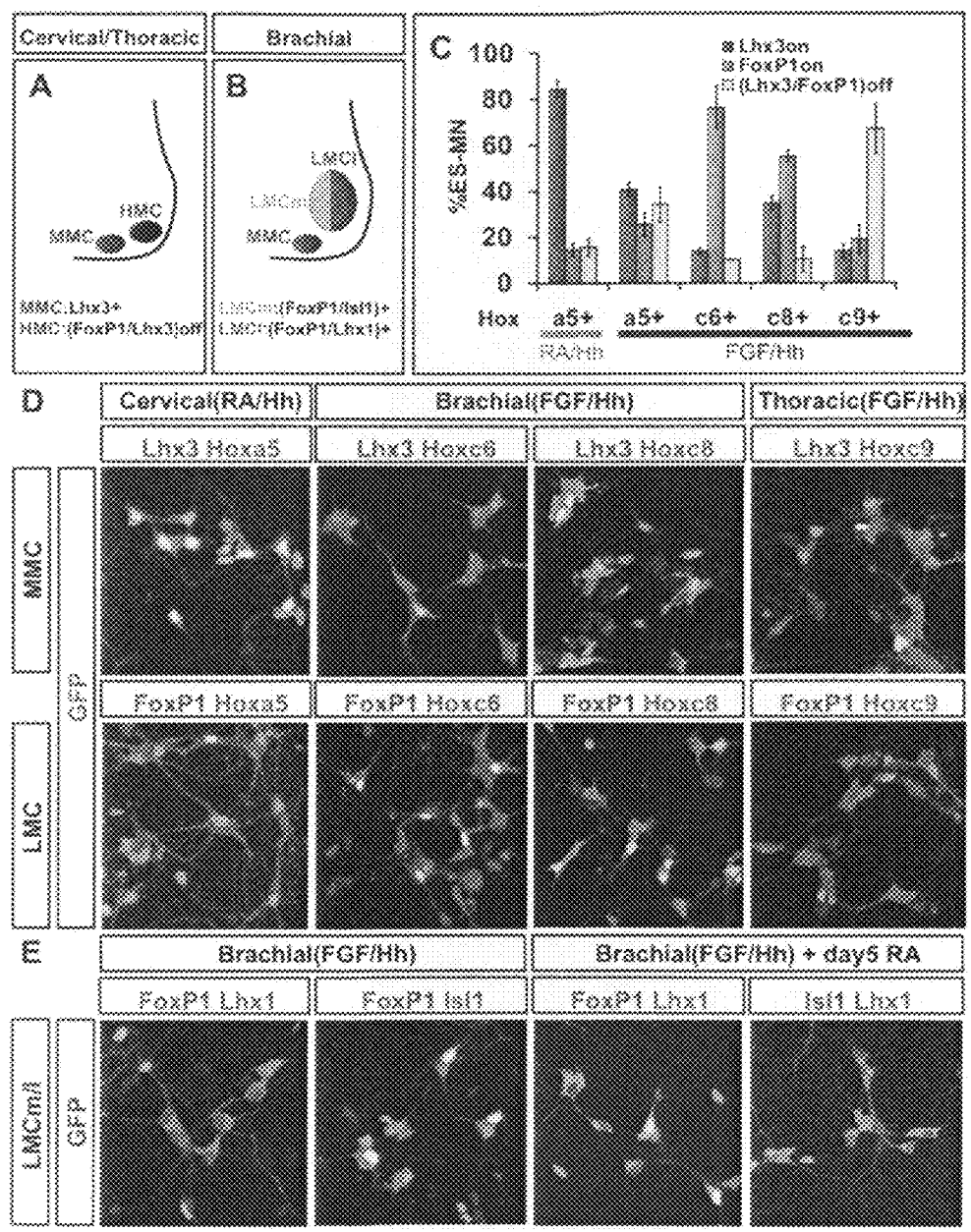
FIG. 14: Correlation between Rostro-caudal and Columnar Identities of ES-MNs: A) At cervical and thoracic levels of the spinal cord, MNs that innervate skeletal muscles are organized into MMC and HMC neurons. While MMC neurons maintain the expression of Lhx3, HMC neurons do not express FoxP1 or Lhx3. B) FoxP1$^+$ LMC neurons at brachial level are sub-divided into Lhx1$^+$ lateral LMC (LMCl) and Isl1$^+$ medial LMC (LMCm) neurons. C) To determine whether ES-MNs acquired different columnar identities depending on their rostro-caudal position, ES-MNs were dissociated on day 6 of differentiation, plated and analyzed on day 7. Co-expression of FoxP1 or Lhx3 with individual Hox proteins was quantified in individual ES-MNs on day 7 of differentiation (n=3, mean±SEM). (Table 1) D) Expression of FoxP1 or Lhx3 in Hoxa5, Hoxc6, Hoxc8, or Hoxc9 expressing ES-MNs derived using RA/Hh or "basal" conditions. E) Majority of FoxP1$^+$ ES-MNs express LMCm marker Isl1. Treatment of ES-MNs on day 5 of differentiation with 1 µM RA results in the emergence of lateral LMC neurons expressing Lhx1 on day 7 of differentiation.

| FIG. 14C (FoxP1$^+$ ESMNs), n = 3 independent experiments, ~200 Hox$^+$ ES-MNs | | | | |
|---|---|---|---|---|
| | RA/Hh Hoxa5$^+$ | FGF/Hh Hoxa5$^+$ | FGF/Hh Hoxc6$^+$ | FGF/Hh Hoxc8$^+$ |
| FGF/Hh Hoxa5$^+$ | 0.12 | | | |
| FGF/Hh Hoxc6$^+$ | 0.0058 | 0.0079 | | |
| FGF/Hh Hoxc8$^+$ | 0.0004 | 0.0040 | 0.0069 | |
| FGF/Hh Hoxc9$^+$ | 0.48 | 0.46 | 0.011 | 0.0066 |

| FIG. 14C, Lhx3$^+$ ESMNs, n = 3 independent experiments, ~200 Hox$^+$ ES-MNs | | | | |
|---|---|---|---|---|
| | RA/Hh Hoxa5+ | FGF/Hh Hoxa5$^+$ | FGF/Hh Hoxc6$^+$ | FGF/Hh Hoxc8$^+$ |
| FGF/Hh Hoxa5$^+$ | <0.001 | | | |
| FGF/Hh Hoxc6$^+$ | <0.001 | 0.0037 | | |
| FGF/Hh Hoxc8$^+$ | <0.001 | 0.24 | 0.018 | |
| FGF/Hh Hoxc9$^+$ | <0.001 | 0.0015 | 0.95 | 0.010 |

Figure 15:
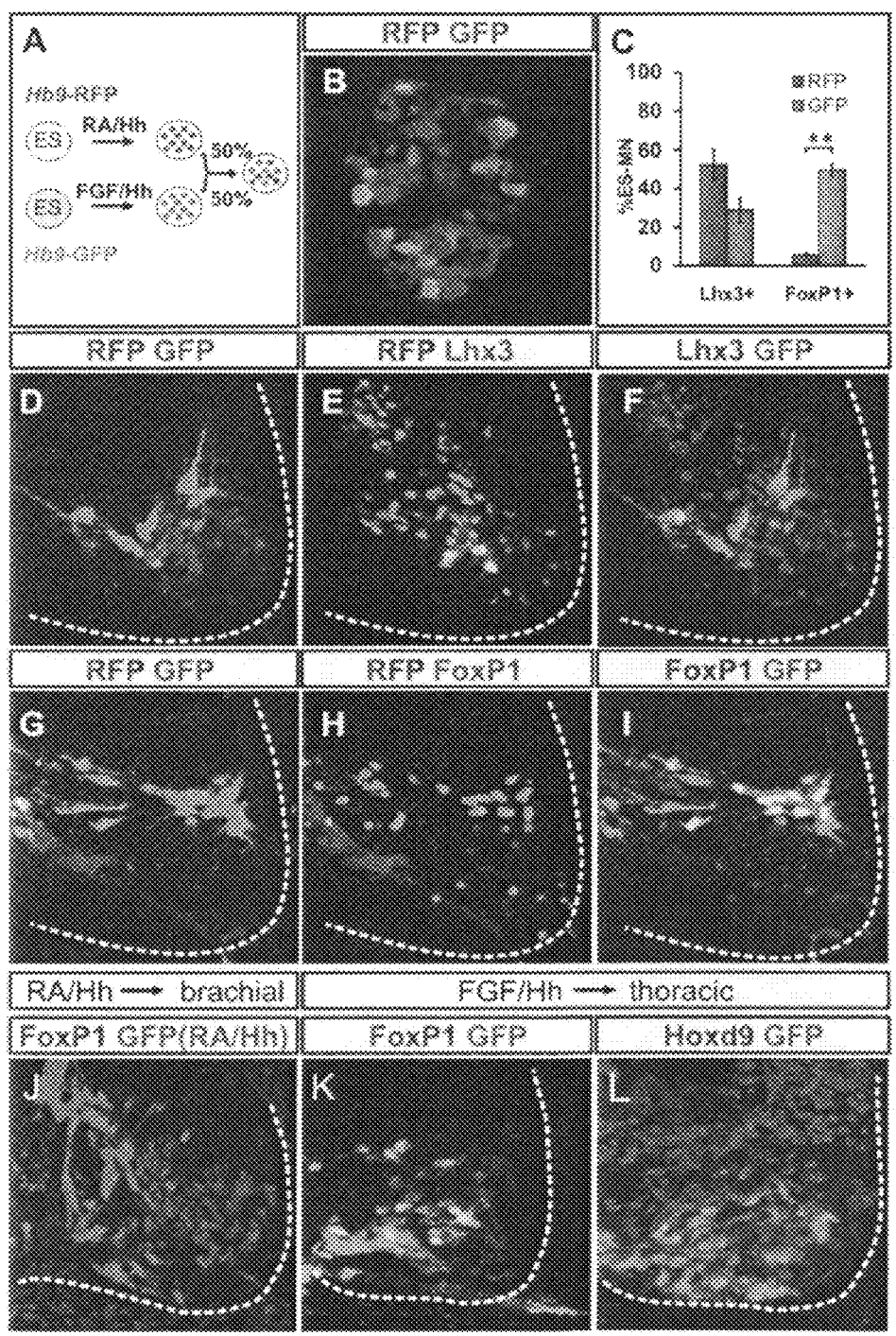
FIG. 15: ES-MNs Maintain Their Columnar Identities upon Transplantation into the Developing Chick Spinal Cord: A) To determine axonal projection preferences of ES-MNs, Hb9-RFP and Hb9-GFP ES cell lines were differentiated using RA/Hh and "basal" conditions, respectively. MNs were dissociated and reaggregated in a 1:1 ratio (Hb9-RFP$^+$:Hb9-GFP$^+$) prior to transplantation. B) Representative image of an ES-MN aggregate containing a mixture of RFP$^+$ (cervical) and GFP$^+$ (brachio-thoracic) ES-MNs. C) Three days after transplantation, expression of FoxP1 and Lhx3 in RFP$^+$ and GFP$^+$ ES-MNs was analyzed. FoxP1$^+$ fraction of GFP$^+$ and RFP$^+$ ES-MNs are significantly different ($p=0.0037$). Graph represents results from three different embryos (n=3, mean±SEM). D-I) Grafted RFP$^+$ (RA/Hh-derived) and GFP$^+$ ("basal"-derived) ES-MNs maintain expression of MMC (Lhx3$^+$) and LMC (FoxP1$^+$) markers in vivo. (D, E, F) and (G, H, I) are the same sections. J) To determine whether columnar identity of ES-MNs could be affected by the grafting procedure, RA/Hh differentiated ES-MNs were grafted ectopically into the brachial level of the chick spinal cord. RA/Hh differentiated ES-MNs did not acquire LMC identity suggesting that segment specific likely do not contribute to specification of columnar identities in grafted ES-MNs. K, L) To determine whether selective cell death could be the underlying reason for our observation on ES-MN migration after grafting, "basal" differentiated ES-MNs were grafted into thoracic chick spinal cord lacking endogenous LMC neurons. "basal" differentiated ES-MNs maintain FoxP1 expression when transplanted ectopically into the Hoxd9$^+$ thoracic spinal cord that lacks endogenous LMC neurons. These results suggest that FoxP1$^+$ cells are capable of surviving at an ectopic location, such as thoracic spinal cord and that the survival of ES-MNs is not the underlying cause for the observed migration of ES-MNs after grafting.

| FIG. 15C (RFP v. GFP grafted ES-MNs), n = 3 embryos, >50 RFP and GFP ESMNs | |
|---|---|
| FoxP1$^+$ | Lhx3$^+$ |
| 0.0037 | 0.084 |

Figure 16:
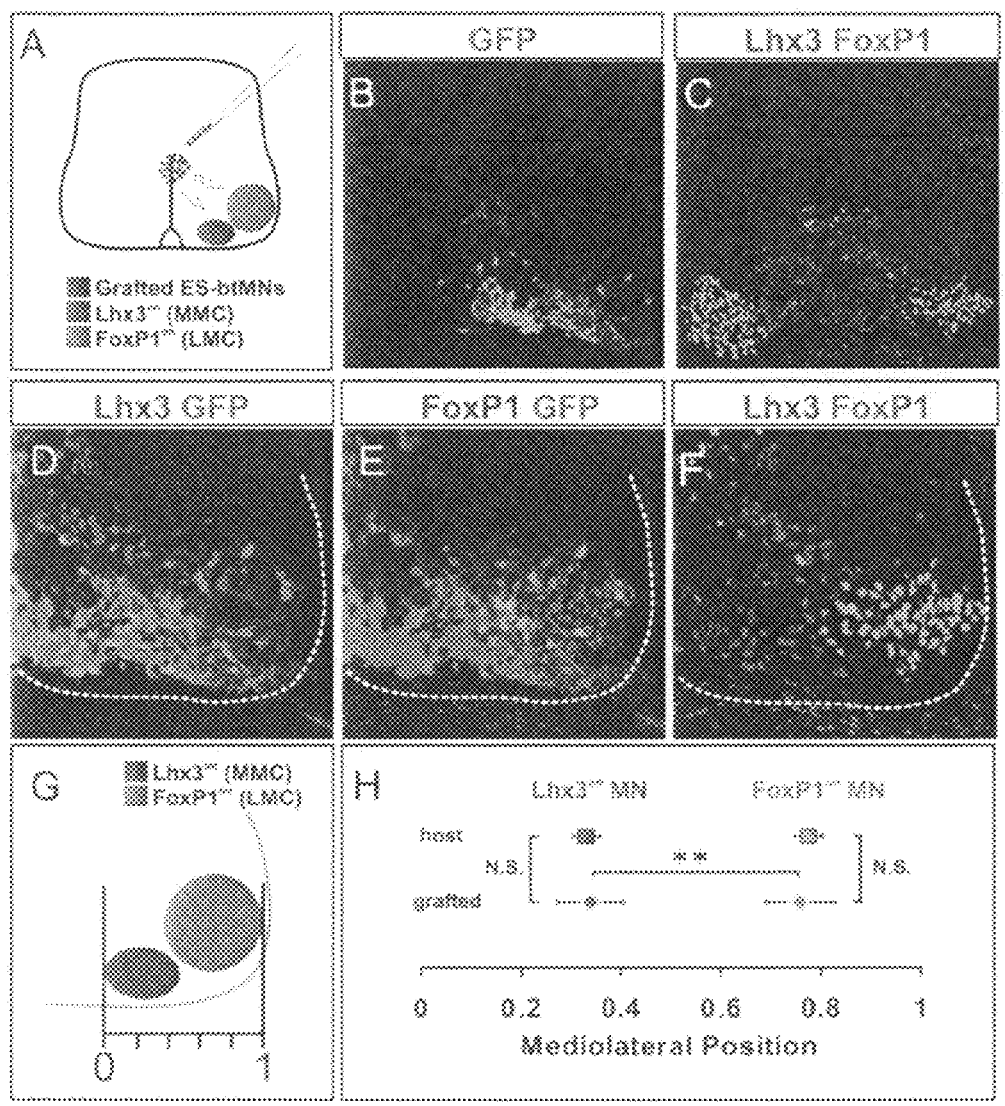
FIG. 16: Column-Specific Migration of ES-MNs upon Transplantation into the Brachial Spinal Cord: A) To determine the settling position of grafted ES-MNs, ES-MNs on day 5 of differentiation were grafted into the HH stage 15-17 chick brachial spinal cord. B) Distribution of GFP$^+$ grafted MNs in the chick developing spinal cord three days after transplantation. C-F) Spinal cord triple labeled for Lhx3, FoxP1 and GFP. Transplanted Lhx3$^+$ and FoxP1 ES-MNs settle in the proximity of endogenous chick MMC and LMC neurons, respectively. G) Schematic of the ventral horn of the spinal cord. Position of each transplanted cell is scored on 0-1 scale with 0 value corresponding to the medial most Lhx3$^+$ endogenous MN and value of 1 corresponding to lateral most FoxP1$^+$ endogenous MN. H) Quantitative analysis of the mediolateral settling position of transplanted and endogenous MNs expressing Lhx3 or FoxP1. The settling position of host FoxP1$^+$ MNs is not significantly different from the settling position of FoxP1$^+$ grafted ES-MNs ($p=0.85$). The settling position of host Lhx3$^+$ MNs is not significantly different from settling position of Lhx3$^+$ grafted ES-MNs ($p=0.92$). However the settling position of transplanted Lhx3$^+$ and FoxP1$^+$ ES-MNs is significantly different ($p=0.0086$). Represented are data from four different chick embryos containing GFP$^+$ grafts three days after transplantation. Over thirty transplanted and endogenous MNs were quantified per embryo. Graphed is mean±SEM.

| FIG. 16H (host v. grafted MNs), n = 4 embryos, ~50 host or grafted MNs per embryo | |
|---|---|
| Lhx3$^+$ | FoxP1$^+$ |
| 0.92 | 0.85 |

| FIG. 16H (Lhx3$^+$ v. FoxP1 MNs), n = 4 embryos, ~50 host or grafted MNs per embryo | |
|---|---|
| host | grafted |
| <0.0001 | 0.0086 |

Figure 17:
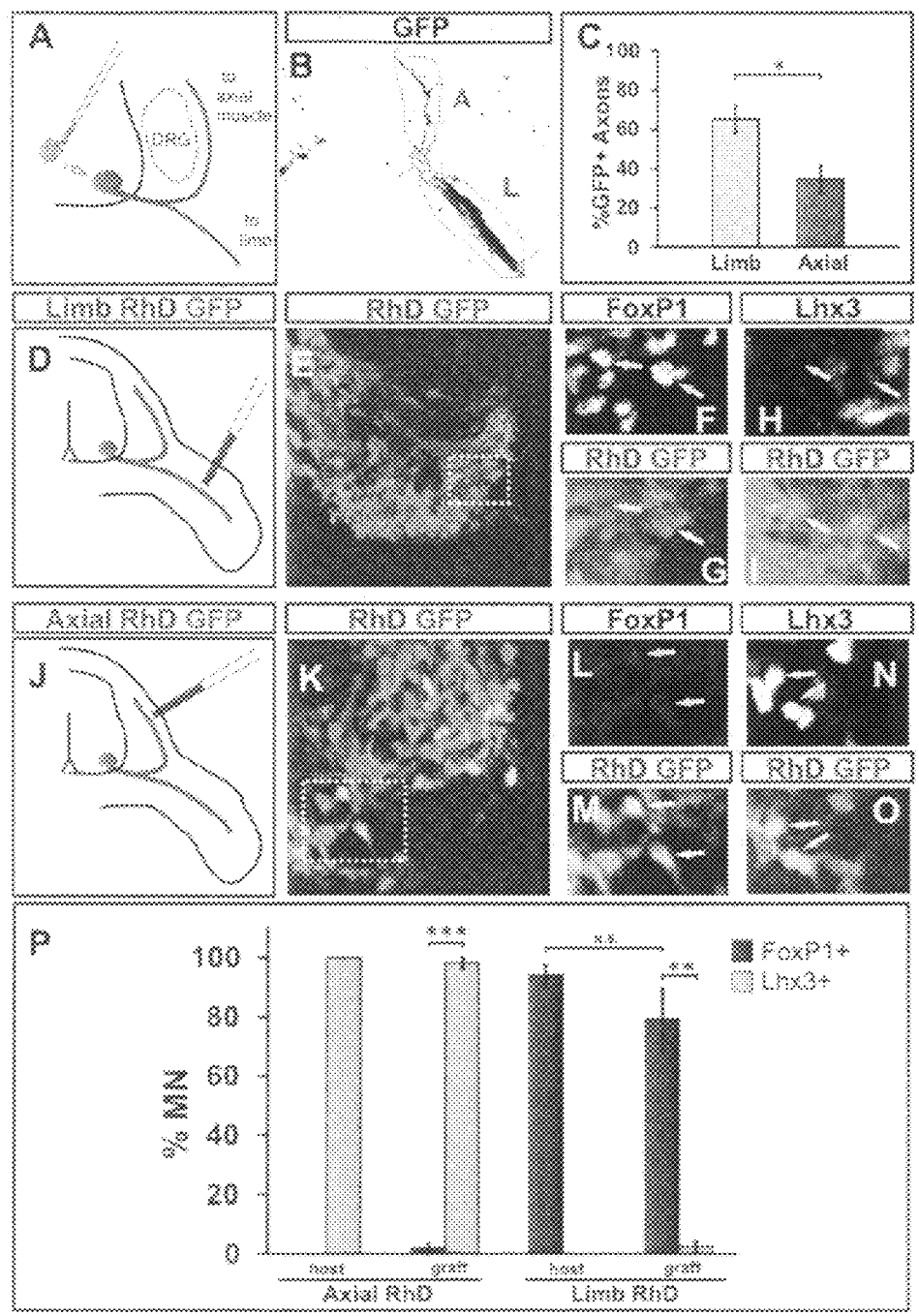
FIG. 17: LMC and MMC ES-MN Axons Navigate Correctly to Limb and Axial Muscles: A) Axon pathfinding preference was examined by grafting GFP$^+$ ES-MNs derived under "basal" condition into chick brachial spinal cord (HH stage 15-17). B) ES-MN axons visualized by GFP intensity in axial (A) and limb (L) nerve branches three days after grafting. C) Quantification of relative contribution of ES-MN axons to limb and axial nerves based on GFP quantification. Significantly higher fraction of GFP$^+$ axons projects to the limb ($p=0.011$). Graph represents results from six different embryos (mean±SEM). D, E) Transplanted "basal" differentiated MNs were backfilled with tetramethylrhodamine-dextran (RhD) from the limb nerve branch to determine the columnar identity of limb projecting ES-MNs. F-I) Transplanted MNs retrogradely labeled from the limb (RhD$^+$/GFP$^+$) express FoxP1 (arrows, F, G) but do not express Lhx3 (arrows, H, I). J, K) Transplanted ES-MNs were backfilled with RhD from the axial nerve branch to determine the columnar identity of axially projecting ES-MNs. L-O) ES-MNs retrogradely labeled from the axial musculature (RhD$^+$/GFP$^+$) express Lhx3 (arrows, N, O) but do not express FoxP1 (arrows, L, M). P) Quantification of Lhx3 and FoxP1 expression by transplanted and endogenous MNs retrogradely labeled with RhD from limb or axial nerve branches. The fraction of Lhx3$^+$ and FoxP1$^+$ ES-MNs projecting axially are significantly different (p<0.0001). Similarly, the fraction of Lhx3$^+$ and FoxP1$^+$ ES-MNs projecting to the limb are significantly different (p=0.002). In contrast, the fraction of endogenous and grafted FoxP1$^+$ MNs labeled from the limb is not significantly different (p=0.26). Graphed are results for three embryos per backfill (axial or limb) experiment (n=3, mean±SEM).

| FIG. 17C, 26C (limb v. axial ES-MN axon projections), n = 6 embryos | |
|---|---|
| (GFP$^+$ axons) | (RFP$^+$ axons) |
| 0.011 | 0.036 |

| FIG. 17C, 26C (RFP v. GFP ES-MN axon projections), n = 6 embryos | |
|---|---|
| limb | axial |
| 0.14 | 0.019 |

| FIG. 17P (grafted v. host MNs), n = 3 embryos, >35 grafted and host RhD$^+$ MNs/embryo | | | |
|---|---|---|---|
| FoxP1$^+$ limb | Lhx3$^+$ limb | FoxP1$^+$ axial | Lhx3$^+$ axial |
| 0.26 | 0.24 | 0.37 | 0.37 |

| FIG. 17P (Lhx3$^+$ v. FoxP1$^+$ MNs), n = 3 embryos, >35 grafted and host RhD$^+$ MNs/embryo | | | |
|---|---|---|---|
| grafted (RhD limb) | host (RhD limb) | grafted (RhD axial) | host (RhD axial) |
| 0.0019 | <0.0001 | <0.0001 | <0.0001 |

Figure 18:
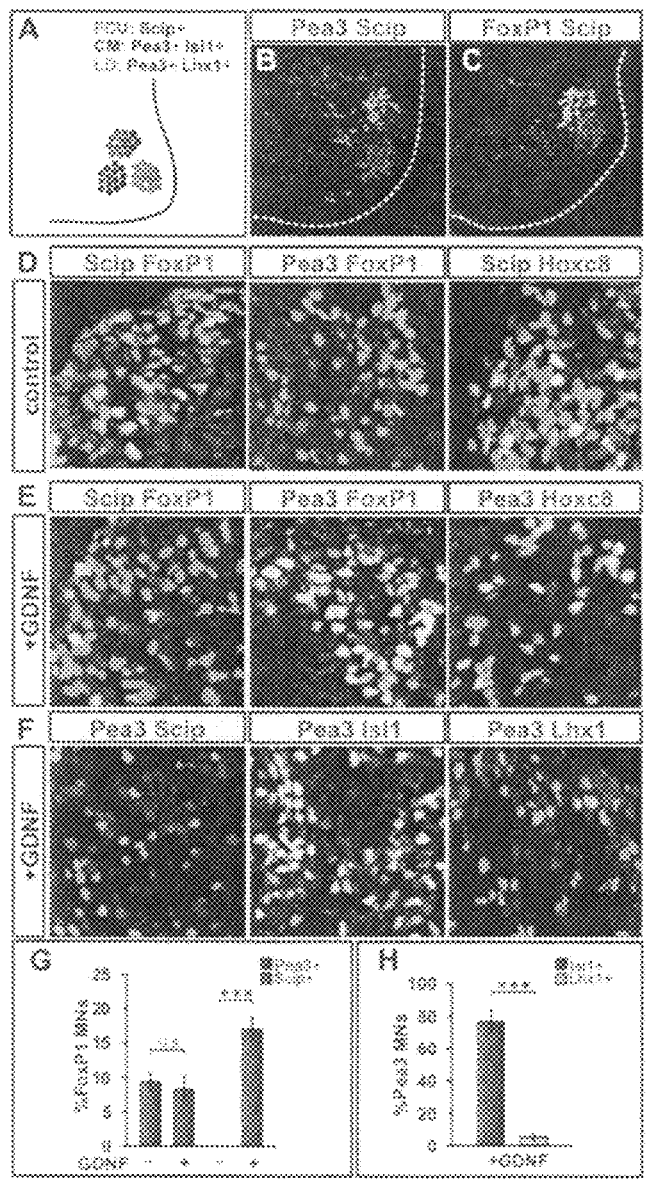
FIG. 18: ES-MNs Acquire Defined Caudal Brachial Motor Pool Identities: A) Three motor pools can be molecularly identified at the caudal brachial LMC: Scip$^+$ motor pool innervating flexor carpi ulnaris (FCU), Pea3$^+$/Isl1$^+$ motor pool innervating cutaneous maximus (CM), and Pea3$^+$/Lhx1$^+$ motor pool innervating latissimus dorsi (LD). B) Mutually exclusive expression of Scip and Pea3 in the E13.5 developing mouse spinal cord. C) Scip is expressed by FoxP1$^+$ LMC neurons at the caudal brachial E13.5 mouse embryonic spinal cord. D) A subset of FoxP1$^+$ ES-MNs express FCU marker Scip but all ES-MNs are Pea3$^-$. Many of Scip$^+$ MNs also express Hoxc8 on day 7 of differentiation. E) A subset of ES-MNs acquires expression of Pea3 in response to GDNF treatment on day 5 of differentiation. Pear MNs express FoxP1 and Hoxc8. F) Expression of Pea3 and Scip in ES-MNs is mutually exclusive. Majority of Pea3$^+$ ES-MNs express CM marker Isl1 but not LD marker Lhx1. Note the intermixing of Pea3 and Scip expressing ES-MNs in the embryoid body that contrasts the clustered organization of motor pools in vivo (B). G) Quantification of Pea3 and Scip expressing FoxP1$^+$ ES-MNs in the presence and absence of GDNF. Upon GDNF treatment, the fraction of Pea3$^+$ LMC ES-MNs is increased significantly (p<0.001) but the fraction of Scip$^+$ LMC ES-MNs remains largely unchanged (p=0.70). Graphed are results from three independent experiments (n=3, mean±SEM). H) To determine whether Pea3$^+$ ES-MNs could be assigned to CM or LD motor pools, the expression of Lhx1 and Isl1 in Pea3 expressing ES-MNs were quantified. Significantly higher fraction (~90%) of Pea3$^+$ ES-MNs express Isl1 while only a small subset (~10%) express Lhx1 (p<0.001). Graphed are results from three independent experiments (n=3, mean±SEM).

| FIG. 18G (GDNF presence v. GDNF absence), n = 3 experiments, >180 FoxP1$^+$ ES-MNs | |
|---|---|
| Pea3$^+$ FoxP1$^+$ | Scip$^+$ FoxP1$^+$ |
| <0.001 | 0.70 |

| FIG. 18H (Isl1$^+$ v. Lhx1$^+$), n = 3 experiments, ~200 Pea3$^+$ ES-MNs |
|---|
| Pea3$^+$ ES-MNs |
| <0.001 |

FIG. 21B (Hb9-GFP+ cells/total), n = 2 experiments, ~500 cells

| (control v. 1 nM RA) | (control v. 1 μM Hh) | (control v. 1 nM RA/ 1 μM Hh) |
|---|---|---|
| 0.10 | 0.075 | 0.030 |

FIG. 21C (Hoxc8+/total ES-MNs), n = 2 experiments, ~250 ES-MNs

| control v. 1 nM RA | (control v. 1 μM Hh) | (control v. 1 nM RA/ 1 μM Hh) |
|---|---|---|
| 0.11 | 0.30 | 0.074 |

Figure 22A:
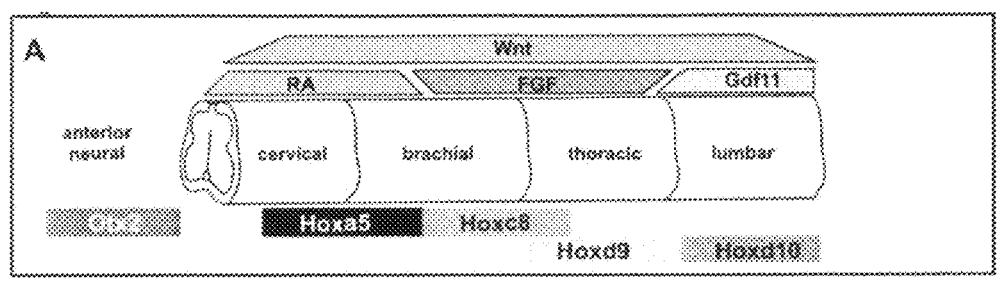
FIG. 22: Rostro-caudal Patterning of Differentiating ES Cells in Response to Endogenous and Exogenous Signals: A) Schematic of the developing spinal cord with principal signals that control the rostro-caudal patterning and Hox expression profile in spinal cord MNs. B-H) To determine if FGF/Hh (control) differentiation condition could be used for patterning ES-MNs along the rostro-caudal axis EBs were grown under low-density FGF/Hh conditions (control) and treated with RA, FGF, RA/FGF/Hh, Gdf11, and PD173074 on day 3 of differentiation and Dkk-1 on day 2 of differentiation. Sections of EBs were immunostained on day 7 of differentiation, except Otx2 on day 5 of differentiation. All differentiation conditions resulted in the specification of NeuN$^+$ neural cells and Hb9-GFP expressing MNs. C) Addition of 10 nM-1 µM RA on day 3 of differentiation resulted in the generation of Hoxa5$^+$ cervical MNs lacking expression of more posterior Hox genes. D) Addition of FGF2 (100 ng/ml) resulted in an increase in the number of Hoxd9$^+$ MNs. E) Treatment of cells with 100 nM RA, 100 ng/ml FGF2, and 100 nM Hh agonist resulted in the specification of Hoxc8$^+$ MNs. F) Treatment of differentiating cells with 20 ng/ml Gdf11 resulted in specification of MNs expressing Hoxd10. G) Blocking Wnt signaling by addition of 1 µg/ml Dkk1 on day 2 of differentiation prevented specification of spinal cells (absence of Hoxa5 and Hoxc8 expression) and resulted in the appearance of Otx2$^+$ forebrain/midbrain neural cells. H) Blocking endogenous FGF signaling by the addition of 50 nM PD173074 on day 3 of differentiation selectively prevented specification of caudal brachial Hoxc8$^+$ ES-MNs. I) Addition of 100 ng/ml of FGF to control condition results in the significant increase in Hoxd9 expressing cells (p=0.007). Graphed are results from three independent experiments (mean±SEM). J) Addition of 20 ng/ml of Gdf11 leads to significant increase in Hoxd10 expressing ES-MNs (p<0.001). Graphed are results from three independent experiments (mean±SEM).
Figures 22B, 22C, 22D, 22E, 22F, 22G, 22H:
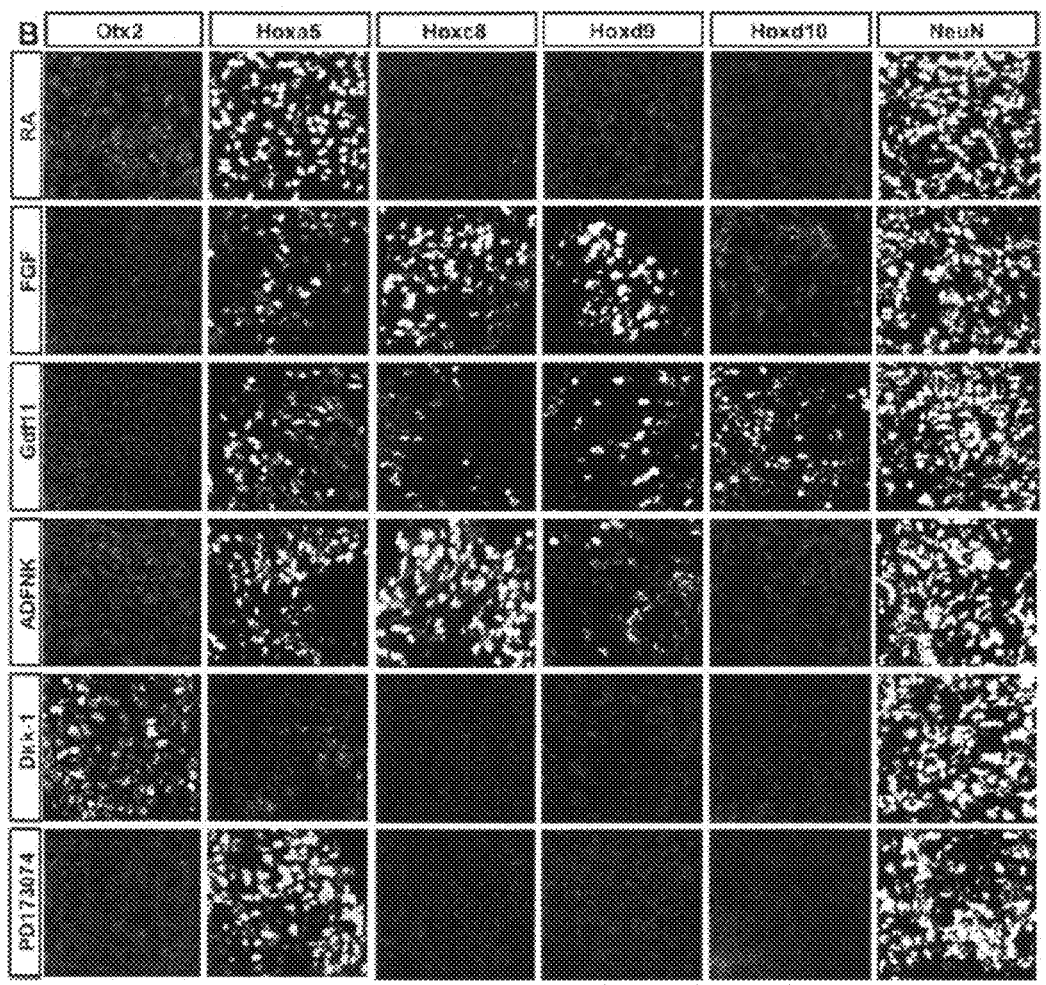
Figures 22I, 22J:
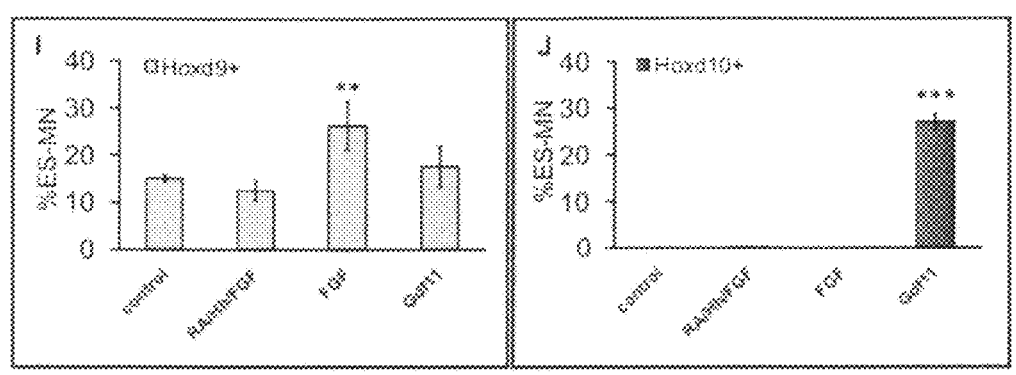

FIG. 22I (Hoxd9+ES-MNs), n = 3 experiments, >1200 Hb9+ ESMNs

| (basal v. FGF) | (basal v. RA/Hh/FGF) | (basal v. Gdf11) |
|---|---|---|
| 0.0066 | 0.15 | 0.60 |

FIG. 22J (Hoxd10+ES-MNs), n = 3 experiments, >600 Hb9+ ESMNs

| (basal v. FGF) | (basal v. RA/Hh/FGF) | (basal v. Gdf11) |
|---|---|---|
| 0.96 | 0.50 | <0.0001 |

FIG. 23B (% Hb9-GFP+ cells), n = 3 experiments, ~250 cells

| control v. 10 nM HhAg | control v. 50 nM HhAg | control v. 100 nM HhAg | control v. 1 μM HhAg |
|---|---|---|---|
| 0.18 | 0.84 | 0.96 | 0.015 |

FIG. 25B (RA/Hh v. FGF/Hh), n = 3 experiments, ~750 ES-MNs

| Foxp1+ | Lhx3+ |
|---|---|
| <0.001 | <0.0001 |

FIG. 25D (% Hoxc8+ ES-MNs), n = 2 experiments, ~100 ES-MNs

| control v. day 3 RA | control v. day 4 RA | control v. day 5 RA |
|---|---|---|
| <0.001 | 0.18 | 0.76 |

FIG. 25F (control v. day 5 RA), n = 3 experiments, >300 FoxP1+ ES-MNs

| Lhx1+ FoxP1+ ES-MNs |
|---|
| 0.044 |

FIG. 25H (BrdU: control v. day 5 RA), n = 3 experiments, ~500 ES-MNs

| Lhx1+ BrdU− ESMNs |
|---|
| 0.028 |

FIG. 26L (diss. v. agg.), n = 3 experiments, ~250 GFP+ MNs

| FoxP1+ | Lhx3+ |
|---|---|
| 0.29 | 0.81 |

FIG. 26M (diss. v. agg.), n = 3 experiments, ~50 FoxP1+ GFP+ MNs

| Pea3+ | Scip+ |
|---|---|
| 0.40 | 0.44 |

Results

Caudalization of ES Cell-Derived Neural Progenitors

Previously the inventors showed that the exposure of ES cells to retinoic acid (RA) and Hedgehog (Hh) generates MNs, defined by expression of an HB9-GFP reporter transgene (Wichterle et al., 2002). These MNs exhibit a rostral cervical identity, as assessed by expression of Hoxa5 (and Hoxc5) (FIG. 13B-C) (Wichterle et al., 2002). To characterize subtype diversity of ES-MNs the inventors asked whether ES cells can be differentiated into brachial MNs, whose molecular and functional properties are well defined (Hollyday and Jacobson, 1990; Lin et al., 1998; Arber et al., 2000; Dasen et al., 2005). Based on the rostralizing influence of RA (Liu et al., 2001), the inventors considered whether omission of exogenous RA from the differentiation medium might permit the generation of MNs of more caudal segmental character. To test this, ES cells were grown at low density in retinoid-deficient, serum free culture conditions that promote neural induction, presumably by minimizing the exposure of cells to BMPs (Watanabe et al., 2005) (FIG. 12D). By screening different medium components (Table 1), an exogenous RA and Hh-free ES cell differentiation medium (Advanced D-MEM/F12/Neuro "basal" medium supplemented with 10% Knockout-SR) was identified that promotes the differentiation of MNs expressing a caudal brachial marker Hoxc8 (Table 1, FIG. 21).

TABLE 1

Comparison of different basal media compositions on formation of embryoid bodies from ES cells, differentiation of Hb9+ ES-MNs, and expression of Hoxc8 in the absence of exogenous factors.

| Medium composition | EBs | % GFP+ MNs | Hoxc8+ |
|---|---|---|---|
| aDMEM/F12/Neurobasal/KSR | + | 8.2 | + |
| GMEM/KSR | + | 0.7 | − |
| DMEM/F12/KSR | + | 0.0 | − |
| Neurobasal/KSR | +/− | 0.2 | + |
| F12/Neurobasal/KSR | +/− | 0.0 | − |
| F12/KSR | − | n/a | n/a |
| DMEM/KSR | +/− | 2.8 | + |
| F12 | − | n/a | n/a |

TABLE 1-continued

Comparison of different basal media compositions on formation of embryoid bodies from ES cells, differentiation of Hb9+ ES-MNs, and expression of Hoxc8 in the absence of exogenous factors.

| Medium composition | EBs | % GFP+ MNs | Hoxc8+ |
|---|---|---|---|
| DMEM/F12 | − | n/a | n/a |
| aDMEM/F12/Neurobasal | +/− | 3.5 | − |

Reported are findings from two independent experiments.

Whether the differentiation of ES cells into Hoxc8+ MNs depends on endogenously expressed caudalizing Wnt and FGF signals was examined (Liu et al., 2001; Nordstrom et al., 2006). To determine whether endogenous Wnt signals (Lako et al., 2001) are involved in the specification of caudal neural identity, ES cells were exposed to the Wnt antagonist Dickkopf-1 (Dkk1) on day 2 of differentiation. ES cells grown in the presence of Dkk1 lacked spinal character, as determined by the absence of Hox and MN markers and by the acquisition of a forebrain/midbrain neural marker Otx2 (FIG. 22G). To determine the involvement of endogenous FGF signals, ES cell differentiation after exposure of cells to the FGF receptor antagonist PD173074 was examined (Mohammadi et al., 1998) on day 3 of differentiation. PD173074 treatment resulted in the generation of ES-MNs that expressed Hoxa5 but lacked Hoxc8 expression (FIG. 22H).

The involvement of endogenous Hh signaling in the generation of ES-MNs was also examined (Briscoe et al., 2000). Clusters of Hh expressing notochord (FoxA2+/Brachyury+) and floor plate (FoxA2+/Brachyury−) cells within the embryoid bodies grown in RA-free conditions was observed (FIG. 23D). Moreover, exposure of ES cells to Hh antagonist 61414 (Williams et al., 2003) blocked the differentiation of ventral spinal progenitors and the formation of MNs (FIG. 23C). Thus, in contrast to previously described RA-free differentiation condition yielding rostralized neural cells ES cells grown as embryoid bodies in the absence of added patterning factors can self-organize and express endogenous signals that caudalize and ventralize induced neural cells. In subsequent experiments whether brachial ES-MNs generated under this basal differentiation condition (further referred to as "basal" condition) can acquire defined molecular and functional subtype specific properties was examined.

Rostro-Caudal Diversity of ES-MNs

To compare the positional identities of MNs generated under RA/Hh and "basal" conditions in a more comprehensive manner, the combinatorial expression of Hoxa5, Hoxc6, Hoxc8, and Hoxc9 proteins in dissociated ES-MN cultures was analyzed. In vivo, these markers delineate cervical and rostral-brachial (Hoxa5+), brachial (Hoxc6+), caudal-brachial and rostral-thoracic (Hoxc8+), and thoracic (Hoxc9+) spinal positional identities (FIG. 13A).

In contrast to the RA/Hh differentiation condition that yields mostly (~90%) Hoxa5+ rostral cervical MNs (Wichterle et al., 2002) (FIG. 13B-C), "basal" exposure resulted in the production of MNs of more caudal character (FIG. 13B, 13D). It was found that ~65% of ES-MNs express Hoxc8 (vs. 0% in RA/Hh differentiation, p<0.0001), indicating caudal brachial or anterior thoracic identity. Effective caudalization of "basal" generated ES-MNs is further demonstrated by the emergence of ~25% of ES-MNs that acquired thoracic identity, marked by expression of Hoxc9 (FIG. 13B, D) (vs. 0% Hoxc9+ ES-MNs generated using RA/Hh, p=0.011). As in vivo, ES-MNs exhibited a mutually exclusive profile of Hoxa5 and Hoxc8 proteins, as well as of Hoxc6 and Hoxc9 proteins (FIG. 13D). Together, these results indicate that ES cells differentiated under "basal" condition give rise to spinal MNs with caudal brachial and thoracic positional identities.

Figure 21:
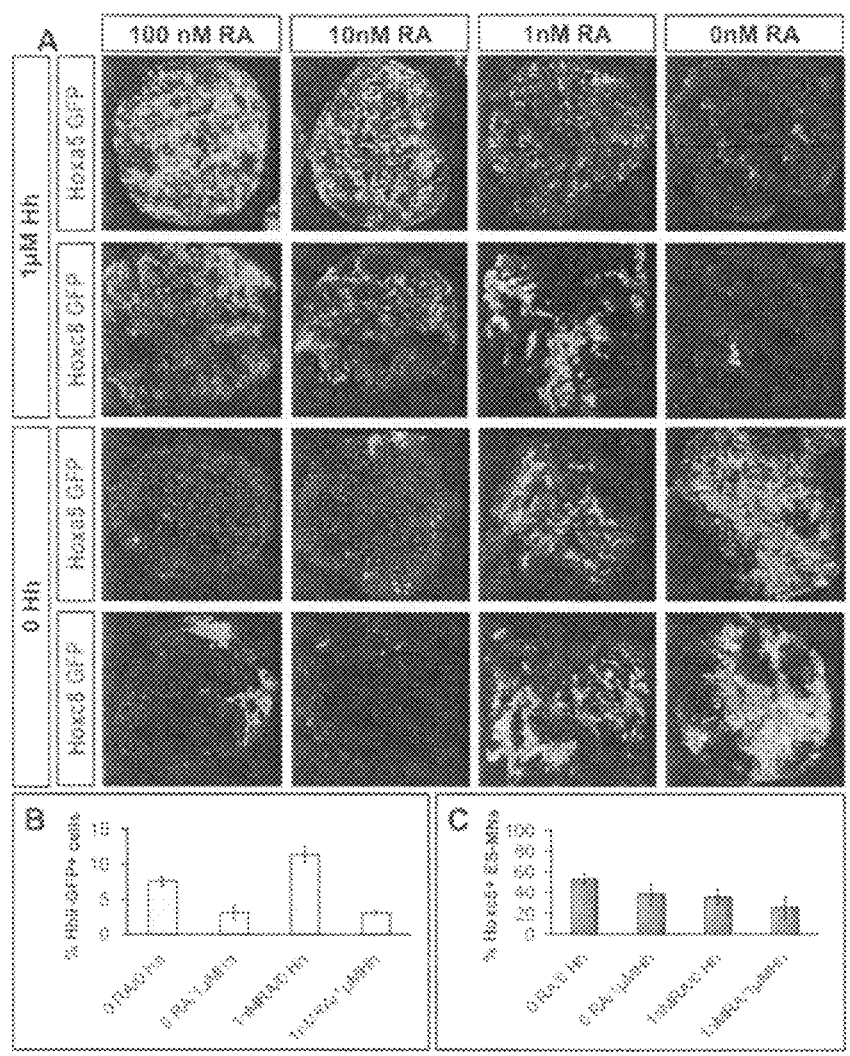
FIG. 21: Titration of Retinoic Acid in the Presence and Absence of Hh Agonist: A) To determine whether decreasing concentrations of RA may result in the specification of caudal brachial ES-MNs EBs were treated with different RA concentrations (100 nM-0 nM) in the presence and absence of 1 µM Hh agonist and expression of Hoxa5, Hoxc8, and Hb9-GFP was examined in the resulting day 7 EBs. While Hoxa5$^+$ MNs are detected in all conditions, Hoxc8$^+$ MNs are efficiently specified only in the absence or low concentrations of exogenous RA and Hh. B) To quantify ES-MN induction efficiency in conditions resulting in the specification of Hoxc8$^+$ ES-MNs (0 RA/Hh, 1 nM RA, 1 µM Hh, and, 1 nMRA/1 µM Hh), EBs were dissociated into single cells on day 7 of dissociation and the number of Hb9-GFP$^+$ and total cells were determined. In general all four conditions resulted in the similar levels of MN induction suggesting that these pharmacological treatments did not significantly affect the fraction of ES-MNs generated during differentiation. Graph represents three independent differentiation experiments (mean±SEM). C) To quantify the fraction of MNs that express Hoxc8 EBs grown in Hoxc8$^+$ ES-MN generating conditions (0 RA/Hh, 1 nM RA, 1 µM Hh, and 1 nMRA/1 µM Hh) were fixed and immunostainings were performed for Hoxc8 and Hb9. 0 RA/0 Hh condition resulted in the highest number of Hoxc8$^+$ ES-MNs. Graph represents two independent experiments (mean±SEM).

The specification of cervical, brachial, thoracic, and lumbar MNs is controlled by opponent gradients of RA and FGF/Gdf11 signals in vivo (Liu et al., 2001; Liu, 2006). Therefore the inventors examined whether the rostro-caudal identity of ES cells differentiated under the "basal" conditions can be programmed by these extrinsic signals. Treatment of differentiating ES cells with RA (10 nM-1 µM) resulted in the specification of Hoxa5+ rostral cervical MNs, whereas treatment with a combination of RA (100 nM) and FGF2 (100 ng/ml), FGF2 alone (100 ng/ml), and Gdf11 (20 ng/ml) resulted in the specification of progressively more caudal, Hoxc8+ brachial, Hoxd9+ thoracic, and Hoxd10+ lumbar MNs, respectively (FIG. 21, 22C, 22D, 22F, 24). Thus, the rostro-caudal identity of MNs generated from ES cells under the low density serum-free culture conditions can be manipulated in a predictive manner by known rostro-caudal patterning signals.

ES-MNs Acquire Discrete Columnar Identities

MNs normally acquire distinct columnar identities as a function of Hox status and rostro-caudal position. MMC neurons are specified at all segmental levels and can be identified by maintained expression of Lhx3 (Sharma et al., 1998). LMC neurons are generated at brachial and lumbar levels in register with their limb targets, and can be identified by high level expression of FoxP1 (Jessell, 2000; Landmesser, 2001; Dasen et al., 2008). HMC neurons are generated at rostral cervical and thoracic segmental levels, innervate body wall muscles, and can be identified by expression of Isl1/2 and Hb9 proteins in the absence of Lhx3 and FoxP1 expression (Dasen et al., 2008). To determine whether brachio-thoracic "basal" and rostral cervical RA/Hh induced ES-MNs acquire columnar identities appropriate for their Hox status, the expression of the MMC marker Lhx3, the LMC marker FoxP1, and Hox proteins was examined.

When ES cells were differentiated in the presence of RA/Hh, ~85% of Hoxa5+ ES-MNs expressed Lhx3 and only ~15% expressed FoxP1 (FIG. 14C-D). In contrast, "basal" induced differentiation of ES cells led to the expression of FoxP1 in a significantly larger number of MNs (FIG. 25B). The percentage of FoxP1+ MNs varied with the rostro-caudal identity of ES-MNs. The greatest number of FoxP1+ cells was observed among the brachial ES-MNs: ~75% of Hoxc6+ and ~55% of the Hoxc8+ ES-MNs expressed FoxP1 (FIG. 14C-D), while the lowest fraction of FoxP1+ MNs was observed in the cervical Hoxa5 and thoracic Hoxc9 ES-MNs (for statistical analysis see Table 1). This distribution matches the location of endogenous LMC neurons in the brachial spinal cord. Conversely, the greatest fraction of HMC-like neurons negative for both Lhx3 and FoxP1 was observed among cervical Hoxa5+ and thoracic Hoxc9+ ES-MNs, consistent with the cervical and thoracic position of HMC (FIG. 14C, D, Table 1). Approximately 20% of Hoxc9+ ES-MNs expressed FoxP1, a molecular signature of preganglionic motor column (Dasen et al., 2008) (FIG. 14C, D). These results indicate that as in vivo, acquisition of columnar identity is tightly coordinated with the rostro-caudal positional identity and Hox gene expression of ES-MNs.

LMC neurons can be further subdivided into Isl1+ medial (LMCm) and Lhx1+ lateral (LMCl) divisions that innervate ventrally and dorsally derived limb muscles, respectively (Kania et al., 2000). The specification of LMCl identity is controlled in part by RA signal secreted from early-born LMC MNs that express the retinoid synthesizing enzyme retinaldehyde dehydrogenase (RALDH2) (Sockanathan and Jessell, 1998). The generation of LMC neurons from ES cells in the absence of exogenous retinoids permitted the inventors to examine whether the LMC divisional identity of ES-MNs can be programmed by RA exposure. Despite the presence of RALDH2 expressing cells within embryoid bodies (FIG. 25E), fewer than 5% of FoxP1$^+$ ES-MNs expressed the lateral LMC marker Lhx1 in the absence of added retinoids. In contrast, exposure to RA on day 5 of differentiation resulted in a significant increase in FoxP1$^+$/Lhx1$^+$ ES-MNs (15% vs. 5% in the control, p=0.044) (FIG. 14E, 25F). The late RA treatment did not change the rostro-caudal positional identity of ES-MNs (FIG. 25C, D). The specification of divisional identity occurs in postmitotic MNs as determined by cumulative labeling of cells with a thymidine analogue BrdU from day 5 onwards (<2% of Lhx1$^+$ BrdU-ES-MNs in the control vs. ~10% of Lhx1$^+$ BrdU− ES-MNs in RA treated, p=0.028) (FIG. 25G, H). Together, these findings indicate that similar to in vivo, postmitotic LMC-like ES-MNs can be directed to acquire LMC1 divisional subtype identity by late RA signaling.

Transplanted ES-MNs Maintain their Columnar Subtype Identity

The ability to generate ES-MNs that express LMC or MMC columnar markers permitted the inventors to examine whether these neurons settle within appropriate columnar territories in the ventral spinal cord and whether they send axons along correct nerve branches in the periphery. Because neuronal migration and axon pathfinding rely on extrinsic guidance cues, extracellular substrates, and the cytoarchitecture of the developing embryo, the inventors elected to analyze the behavior of ES-MNs after transplantation into the spinal cord of host chick embryos (Wichterle et al., 2002; Wichterle et al., 2009).

It was first determined whether ES-MNs maintain their subtype identities when transplanted to homotopic and heterotopic locations within the chick neural tube. To compare whether the columnar subtype identities of co-transplanted RA/Hh induced cervical, and "basal" brachio-thoracic ES-MNs are stable a transgenic ES cell line was developed that carries Hb9-RFP transgene. Expression of RFP in this line coincided with the expression of MN specific markers Hb9 and Isl1/2 (data not shown). Embryoid bodies containing RFP$^+$ rostral cervical ES-MNs generated in the presence of RA/Hh were dissociated and mixed in 1:1 ratio with GFP$^+$ brachio-thoracic ES-MNs grown under the "basal" condition (FIGS. 15A, 15B, 26A). The resulting aggregates were transplanted into the brachial neural tube of chick embryos at Hamburger-Hamilton (HH) stage 15-17 (Hamburger and Hamilton, 1992), the time of endogenous MN generation. Transplanted chick embryos were harvested three days later (HH stage 28) and expression of MN columnar markers FoxP1 and Lhx3 in GFP$^+$ and RFP$^+$ ES-MNs was examined.

The percentage of transplanted brachio-thoracic GFP$^+$ ES-MNs that expressed FoxP1 and Lhx3 in vivo was nearly identical to the percentages of "basal" induced ES-MNs expressing these markers in vitro (~50% FoxP1$^+$ in vivo vs. ~40% FoxP1$^+$ in vitro, p=0.024; ~30% Lhx3$^+$ in vivo vs. ~30% Lhx3$^+$ in vitro, p=0.92) (FIGS. 15C, 15F, 15I, 25A, 25B), indicating that their columnar identity is largely unaffected by the grafting procedure. Heterotopic transplantation of RFP$^+$ cervical ES-MNs into the brachial spinal cord did not result in respecification to FoxP1$^+$ LMC identity (~5% in vivo vs. ~10% in vitro, p=0.023) (FIG. 15H, 15J), but a decrease in the fraction of Lhx3$^+$ ES-MNs (~60% in vivo vs. ~80% in vitro, p=0.022) was detected (FIGS. 15C, 15E, 15H, 25). Approximately 30% of cervical ES-MNs exhibited a transcriptional profile characteristic of HMC neurons (Lhx3$^-$/FoxP1$^-$) after transplantation (FIG. 15C, 15E, 15H). The temporal loss of Lhx3 expression is likely to reflect the normal process of Lhx3 downregulation during the maturation of non-MMC MNs (Sharma et al., 1998; Agalliu et al., 2009).

From these findings, it was concluded that brachio-thoracic ES-MNs maintain expression of columnar markers and cervical ES-MNs are not reprogrammed to LMC identity after transplantation into the brachial neural tube. These observations provided a basis for analysis of the settling behavior and axonal trajectory of MMC-like and LMC-like ES-MNs in vivo.

FoxP1$^+$ ES-MNs Settle in the Ventrolateral Spinal Cord

LMC and MMC neurons settle in discrete positions within the ventral spinal cord. MMC neurons settle medially and LMC neurons laterally (FIG. 16A). The inventors tested whether ES-MNs are able to interpret migratory and settling cues within the host spinal cord and segregate according to columnar subtype identity. The settling positions of "basal" differentiated Lhx3$^+$ and FoxP1$^+$ ES-MNs three days after transplantation was monitored (HH stage 28) when endogenous MMC and LMC columns are anatomically well separated (Tsuchida et al., 1994) (FIGS. 16A-F). The position of transplanted and endogenous MNs was scored on a 0 to 1 relative scale, where 0 corresponds to the medial-most and 1 to the lateral-most endogenous MNs (FIG. 16G). Lhx3$^+$ ES-MNs settled ventro-medially (0.28±0.02, mean±SEM) in a region matching endogenous MMC (0.33±0.03, p=0.92) (FIG. 5H), whereas FoxP1$^+$ ES-MNs settled in the lateral domain of the ventral horn (0.68±0.03) in the proximity of endogenous LMC (0.77±0.02, p=0.85) (FIG. 5H). These findings provide evidence that ES-MNs assume settling positions appropriate for their columnar subtype identity (Lhx3$^+$ vs. FoxP1$^+$ ES-MNs, p<0.01).

The inventors considered whether selective survival of ES-MNs in response to column-specific trophic factors might underlie the apparent segregation of ES-MNs after transplantation. To address this issue, whether FoxP1$^+$ ES-MNs can survive when ectopically transplanted into the thoracic spinal cord, a region that lacks endogenous LMC neurons was examined. Grafted FoxP1$^+$ ES-MNs survived and maintained FoxP1 expression in this ectopic location (FIG. 15K). Moreover, their cell bodies settled in the lateral aspect of the thoracic spinal cord (FIG. 15K, L), forming what appeared to be an ectopic LMC. These results indicate that the survival and settling of LMC ES-MNs is not contingent on the presence of endogenous LMC neurons or on endogenous trophic and guidance support provided at brachial level of the spinal cord. Based on these observations, and on the finding that columnar identity of ES-MNs is not altered upon transplantation (FIG. 15J), it was concluded that the sorting of ES cell-derived MMC and LMC neurons reflects an active process of cell body migration to column-specific settling positions.

The Axons of ES Cell-Derived LMC Neurons Project into the Limb

All spinal motor axons exit the spinal cord via the ventral roots, but depending on columnar identity, their axonal trajectories diverge to innervate distinct peripheral targets (Landmesser, 2001). MMC axons make a sharp dorsal turn to innervate axial muscles, LMC axons continue to grow distally to innervate the developing limb bud, and HMC axons similarly project distally, although by virtue of their thoracic and rostral cervical location, they invade the body wall musculature rather than the limb. Moreover, genetic studies have shown that HMC neurons generated ectopically within the brachial spinal cord of FoxP1-deficient mice project axons along LMC-like trajectories towards limb muscles (Dasen et al., 2008). Therefore it was considered whether ES-MNs are able to interpret axon guidance cues and project their axons along appropriate peripheral trajectories when transplanted into the brachial spinal cord of HH stage 15-17 chick embryos.

If ES-MNs project axons along nerve branches appropriate for their columnar subtype identity, it is anticipated that ~70% of brachio-thoracic ("basal" induced) ES-MNs will project axons towards the limb (~50% LMC-like and ~20% HMC-like ES-MNs observed in vivo after transplantation) while the remaining ~30% of neurons will project axially (~30% of MMC-like neurons observed in vivo after transplantation). Based on the percentages of Lhx3$^+$ ES-MNs in vitro (~80%) and after transplantation (~60%) it is anticipated that 60-80% of cervical (RA/Hh induced) ES-MN axons will project towards axial muscles.

To compare the axonal projections of cervical and brachio-thoracic ES-MNs under similar grafting conditions, the inventors transplanted aggregates containing a mixture of RFP$^+$ cervical ES-MNs differentiated under RA/Hh, and GFP$^+$ brachio-thoracic ES-MNs differentiated under "basal" conditions, into the chick brachial level spinal cord. Three days after transplantation (HH stage 28), embryos were harvested and the contribution of RFP$^+$ and GFP$^+$ ES-MN axons to axial and limb nerve branches was examined (FIG. 17A, 17B, 26B). Approximately 35% of brachio-thoracic GFP$^+$ ES-MN axons within the axial nerve branch, and ~65% of GFP$^+$ ES-MN axons were detected within the limb nerve branch (p=0.011) (FIG. 17B, C). In contrast, ~60% of RFP$^+$ ES-MN axons projected axially and ~40% projected into the limb (p=0.036) (FIG. 26B, 26C). This distribution is similar to the fraction of MMC-like and LMC/HMC-like ES-MNs observed after transplantation (FIG. 15C). These results reveal consistent preferences in the axonal projections of cervical and brachio-thoracic ES-MNs.

To determine whether the axon pathfinding choice of individual transplanted ES-MNs conforms to their columnar subtype identity, retrograde tracing experiments were performed. Transplanted "basal"-derived GFP$^+$ MNs containing a mixture of MMC, LMC and HMC-like neurons were retrogradely labeled with tetramethylrhodamine-dextran (RhD) from axial or limb motor nerve branches, three days after transplantation (HH stage 28) (FIG. 17D, 17J). The fractions of Lhx3$^+$ and FoxP1$^+$ ES-MNs labeled with RhD were compared to the fractions of endogenous RhD labeled Lhx3$^+$ and FoxP1$^+$ MNs (FIG. 17P).

It was observed that >95% of the transplanted ES-MNs retrogradely labeled from the axial nerve branch expressed Lhx3 (FIGS. 17N, 17O, 17P). Conversely, ~80% of transplanted ES-MNs retrogradely labeled from the limb expressed FoxP1 (FIGS. 17E, 17F, 17G, 17P). Fewer than 5% of transplanted ES-MNs expressing FoxP1 misprojected to the axial nerve branch and fewer than 5% of Lhx3$^+$ ES-MNs misprojected to the limb nerve branch (FIGS. 17H, 17I, 17K, 17L, 17M, 17P). These findings indicate that LMC and MMC ES-MNs extend axons along appropriate nerve branches and avoid incorrect peripheral territories. It was found that ~20% of transplanted ES-MNs backfilled from the limb lacked expression of Lhx3 or FoxP1 (FIG. 17P). This finding suggests that axons of HMC-like neurons located at brachial levels of the spinal cord grow distally and invade the developing limb, as in vivo (Dasen et al., 2008). Together, these results indicate that MNs generated from ES cells in vitro acquire receptors and guidance systems needed to direct their axons along subtype appropriate peripheral axonal trajectories.

ES-MNs Acquire Defined Motor Pool Characters

The establishment of motor pool identity within LMC neurons is a refined step in MN subtype diversification. Early phases of motor pool specification are controlled by cell-intrinsic Hox transcriptional network (Dasen et al., 2005), but later phases depend on signals derived from the limb mesenchyme (Lin et al., 1998; Haase et al., 2002; Dasen et al., 2005). Therefore the inventors considered whether ES-MNs can acquire expression of motor pool-specific molecular markers, and if so, whether specification of motor pool identity in vitro depends on limb-derived inductive signals.

The inventors focused on three motor pools within the caudal brachial LMC that can be identified by differential expression of divisional (Isl1 and Lhx1) and motor pool (Scip and Pea3) markers: the Scip$^+$/Isl1$^+$ flexor carpi ulnaris (FCU) motor pool, Pea3$^+$/Lhx1$^+$ latissimus dorsi (LD) motor pool, and Pea3$^+$/Isl1$^+$ cutenous maximus (CM) motor pool (FIG. 18A-C). Expression of Pea3 by the CM and LD motor pools depends on glial cell line-derived neurotrophic factor (GDNF) signaling from the limb (Lin et al., 1998; Haase et al., 2002) (FIG. 27A-B), whereas it was found that expression of Scip by the FCU motor pool is programmed independently of limb-derived signals (FIG. 27A, 27C). Since many ES-MNs generated under the "basal" condition expressed Hoxc6, Hoxc8, and FoxP1 (FIG. 14D), transcription factors implicated in the establishment of FCU, CM and LD motor pool identities in vivo (Dasen et al., 2005; Dasen et al., 2008), the inventors examined whether ES-MNs generated in vitro expressed Pea3 or Scip.

The FCU pool marker Scip was expressed by ~10% of FoxP1$^+$ ES-MNs, most of which co-expressed Hoxc8 and Isl1, consistent with transcriptional profile of FCU MNs in vivo (FIG. 18D).

In contrast, brachial ES-MNs lacked the expression of CM/LD motor pool marker Pea3 (FIG. 18D). This observation prompted the inventors to examine whether, as in vivo, Pea3 expression depends on GDNF signaling. Treatment of ES-MNs differentiated under the "basal" condition with 10 ng/ml of GDNF on day 5 of differentiation resulted in the induction of Pea3 expression in ~20% of FoxP1$^+$ ES-MNs (vs. 0% in the absence of GDNF, p<0.001) (FIGS. 18E, 18G). Pea3$^+$ CM and LD motor pools can be distinguished by expression of Isl1 and Lhx1, respectively (Livet et al., 2002; Dasen et al., 2005). It was found that the majority of Pea3$^+$ ES-MNs expressed the medial LMC marker Isl1 (FIGS. 18F, 18H) (~90% of Pear ES-MNs express Isl1 vs. ~10% of Pea3$^+$ ES-MNs express Lhx1, p<0.001), indicating that Pea3$^+$ ES-MNs are of CM rather than LD motor pool subtype identity.

Exposure of spinal cord explants to GDNF elicits expression of Pea3 selectively in MNs of the CM and LD motor pools (Haase et al., 2002; Helmbacher et al., 2003), indicating that the GDNF receptive component of motor pool identity is specified prior to and independently of GDNF exposure. It was observed a similar specificity of Pea3 expression in ES-MNs. GDNF was not sufficient to induce Pea3 expression in Hoxc8$^-$ ES-MNs of rostral cervical identity (FIG. 27D) or in Scip$^+$ caudal brachial ES-MNs (FIG. 18F). Moreover, the fraction of Scip$^+$ ES-MNs generated in the presence or absence of GDNF was nearly identical indicating that the prospective CM MNs do not convert into FCU MNs in the absence of GDNF (~10% of Scip$^+$ FoxP1$^+$ ES-MNs in the presence or absence of GDNF, p=0.70) (FIG. 18D, 18E, 18G). Although CM and FCU MNs are both specified in the medial division of the Hoxc8$^+$ caudal brachial LMC, it was found that Pea3$^+$ (Hoxc6$^+$) and Scip$^+$ (Hoxc6$^-$) ES-MNs can also be distinguished by differential expression of Hoxc6 (FIG. 27D), as in vivo (Dasen et al., 2003). Together these results indicate that motor pool diversification of ES-MNs is programmed by intrinsic rostro-caudal transcriptional programs that determine the responsiveness of MNs to limb-derived signals.

To examine the extent the specification of motor pool identity dependent on extrinsic signals provided by neighboring brachial neural cells, Hb9-GFP motor neuron progenitors generated under the "basal" condition was dissociated on day 4 of ES cell differentiation when rostro-caudal identity is determined (FIG. 25C, D) and mixed them with a 5 fold excess of wt progenitors generated under RA/Hh conditions. Three days later the subtype identity of "basal" derived GFP+ ES-MNs scattered among unlabeled cervical MNs was examined. Individual "basal" derived ES-MNs were not respecified by surrounding cervical cells to more rostral identity as they expressed caudal brachial marker Hoxc8 (data not shown) and LMC marker (FIG. 19D-G, 19L). The cell autonomy of the differentiation program controlling motor pool diversification is supported by the observation that motor neurons expressing Pea3 or Scip pool specific markers are detected among GFP positive MNs at similar ratios as in the control embryoid bodies that were not disrupted and cocultured with ectopic cells (FIG. 19H-K, 19M). Together these observations are consistent with the idea that motor pool diversification is controlled by an intrinsic transcriptional program.

Discussion

Attempts to generate defined cell types from ES and iPS cells have typically resorted to two general approaches. In one approach, cell identity is programmed by forced expression of developmentally regulated transcription factors implicated in the control of cell type specification (Kyba et al., 2002; Andersson et al., 2006; Martinat et al., 2006; Takahashi and Yamanaka, 2006). An alternative approach is to expose stem cells to extrinsic patterning signals (Lee et al., 2000; Wichterle et al., 2002; Kubo et al., 2004; D'Amour et al., 2006; Lee et al., 2007; Dimos et al., 2008; Murry and Keller, 2008; Park et al., 2008; Ebert et al., 2009; Soldner et al., 2009). Here provide evidence is provided for a variant on this second strategy: the induction of self-organizing and endogenous patterning centers in embryoid bodies that recapitulate the intrinsic patterning processes of the developing embryo.

The inordinate degree of diversification of neuronal subtypes in the central nervous system poses a significant challenge for the generation of defined neuronal classes from ES cells. Many studies have reported culture conditions under which mouse and human ES cells can differentiate into distinct classes of nerve cells (Kawasaki et al., 2000; Lee et al., 2000; Wichterle et al., 2002; Ying et al., 2003; Ikeda et al., 2005; Li et al., 2005; Watanabe et al., 2005; Yan et al., 2005; Su et al., 2006; Lee et al., 2007; Gaspard et al., 2008). Despite this, it remains unclear whether these in vitro generated neurons represent highly differentiated subclasses of nerve cells found in vivo, and if so, whether they follow normal developmental programs that confer a degree of maturity and functionality that is comparable to their in vivo counterparts. A detailed characterization of the subtype specific properties of in vitro derived neurons is a key step in evaluating whether ES cell derivatives can serve as valid substitutes for primary nerve cells in basic and translational research applications.

Figure 19:
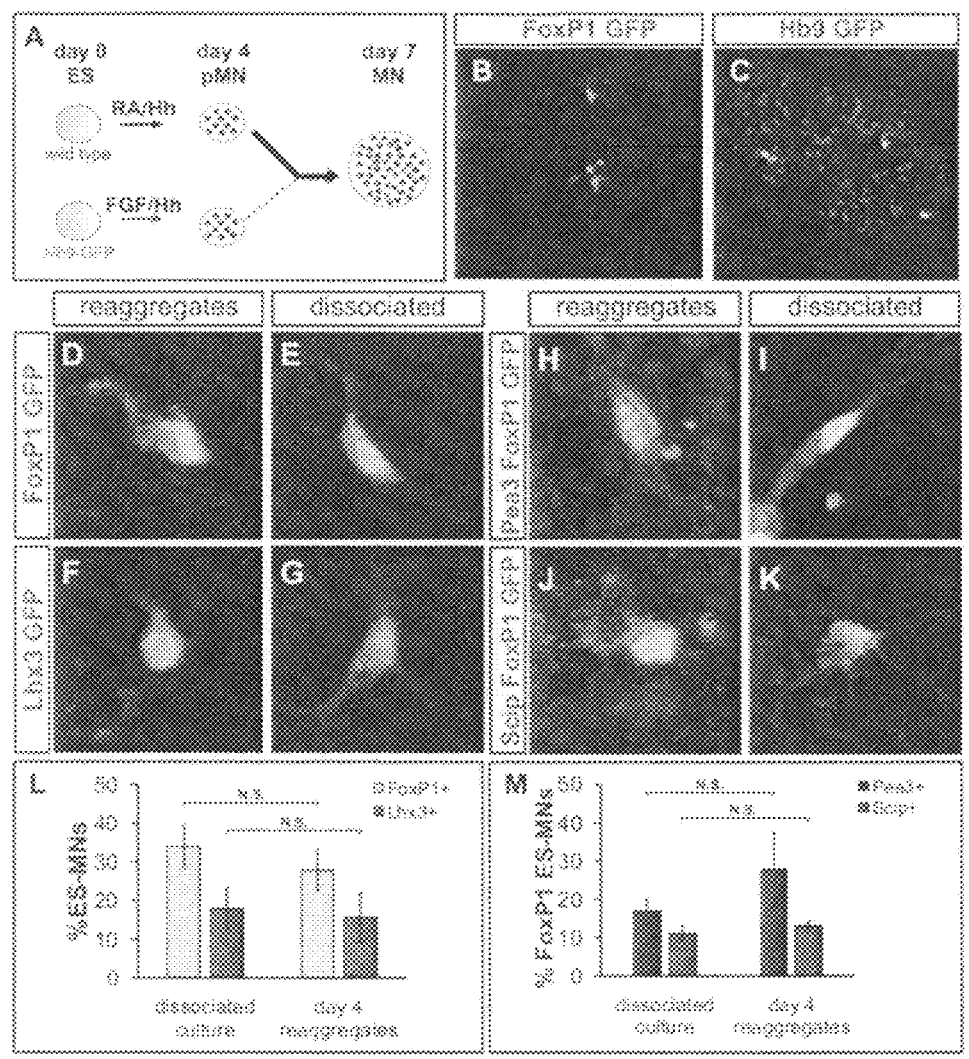
FIG. 19: Cell Autonomous Acquisition of Motor Pool Identities from Mouse ES Cells: A) To determine whether ES-MNs are capable of acquiring Scip$^+$ and Pea3$^+$ motor pool identities in a cell autonomous fashion from the progenitor state, day 4 EBs resulting from "basal" differentiation of Hb9-GFP ES cells were dissociated and mixed in a 1:5 ratio with RA/Hh derived day 4 wild type EBs. On day 7 reaggregates were examined for their expression of columnar and motor pool markers. B) 3 GFP$^+$ ES-MNs can be observed in a cross section of an embryoid body. ⅓ ES-MNs is marked by the expression of FoxP1. C) RA/Hh differentiated Hb9$^+$ GFP$^-$ ES-MNs comprise most of the reaggregated tissue with scattered "basal" derived ES-MNs marked by GFP expression. D, E, F, G) Whether dissociated on day 6 of differentiation or reaggregated with RA/Hh wild type cells on day 4 of dissociation ES-MNs acquire expression of FoxP1 and Lhx3, suggesting that the acquisition of columnar identity is not affected by the reaggregation procedure. H, I, J, K) Pea3$^+$ and Scip$^+$ LMC ES-MNs can be observed both in reaggregates and in dissociated cultures. L) The fractions of FoxP1$^+$ and Lhx3$^+$ ES-MNs are not significantly different in dissociated cultures when compared to reaggregates (~30% of dissociated and reaggregated ES-MNs express FoxP1, p=0.29; ~15 of dissociated and reaggregated ES-MNs express Lhx3, p=0.81). Graphed are results from three independent experiments (n=3, mean±SEM). M) The fractions of Pea3$^+$ FoxP1$^+$ ES-MNs and Scip$^+$ FoxP1$^+$ ES-MNs are not significantly different when ES-MNs are reaggregated on day 4 of differentiation compared to dissociation and plating on day 6 of culture (~15% of FoxP1$^+$ ES-MNs express Pea3 in dissociated cultures vs. ~25% of FoxP1$^+$ ES-MNs express Pea3 in reaggregates, p=0.40; ~10% of FoxP1$^+$ ES-MNs express Scip in dissociated cultures and reaggregates, p=0.44). Graphed are the results from three independent experiments (n=3, mean±SEM).

In this study it was shown that ES cells can self-organize and form endogenous signaling centers that are sufficient to control the specification of highly specialized spinal MN subtypes. MN specification under these conditions relies on known rostro-caudal and dorsoventral patterning signals. Transplantation of ES-MNs into the developing spinal cord confirms that ES-MNs not only acquire a correct molecular character but also exhibit appropriate migratory and axon pathfinding preferences, as well as appropriate sensitivity to limb-derived inductive signals (FIG. 19). Together, these findings demonstrate that ES cells can be induced to mature into MN subtypes that closely resemble those generated in vivo.

Generation of Distinct Rostro-Caudal MN Subtypes from ES Cells

Previous studies employing RA-independent conditions for the differentiation of ES cells yielded nerve cells of rostral identity (Watanabe et al., 2005; Eiraku et al., 2008; Gaspard et al., 2008). Here evidence is presented that low density ES, cell differentiation under modified culture conditions leads to the formation of self-organized embryoid bodies containing endogenous signaling centers secreting factors necessary for caudalization and ventralization of embryoid bodies and the emergence of caudal brachial MNs. The data here indicate that induction of endogenous Wnt, FGF and Shh expression is an important intermediary step. Indeed, the inventors and others have detected an increase in Wnt3, Wnt5b, Wnt8a, FGF4, FGF5, and FGF15 expression in ES cells at the time that differentiating ES cells start to acquire their rostro-caudal identity (Lako et al., 2001; Stpyridis et al., 2007; ten Berge et al., 2008; MP and HW, data not shown).

ES cell differentiation in the absence of exogenously supplied factors provides a responsive cellular system that can be manipulated with relevant rostro-caudal patterning signals. Using expression of Hox proteins as molecular indicators of rostro-caudal positional identity it was shown that MNs of cervical, brachial, thoracic or lumbar spinal identity can be generated from ES cells in a predictable fashion. Although this study focused on molecular and functional characterization of brachial MN subtypes, the strategies documented should facilitate derivation of any one of the dozens of somatic MN subtypes found in the mammalian spinal cord.

Extrinsic Signals and Intrinsic Programs Controlling MN Subtype Diversity

The specification of MN subtype identity, connectivity and function is controlled by a combination of extrinsic signals and intrinsic transcriptional programs. While the rostro-caudal positioning of LMC neurons is determined by Hox transcriptional programs (Dasen et al., 2003), paracrine retinoid signaling controls divisional diversification of LMC neurons (Sockanathan et al., 2003). Analysis of Hox gene function within the brachial spinal cord has led to proposals that motor pool diversification relies on intrasegmental cross-regulatory interactions among Hox genes and their co-factors in a largely cell-autonomous fashion (Dasen et al., 2005).

The view that cell-autonomous programs lead to the diversification of motor pools is supported by the observation that the acquisition of relevant motor pool identities can occur in embryoid bodies lacking organized motor columns and motor pools (FIG. 18B, 18F). In contrast, ES-MNs are not able to acquire lateral LMC divisional identity, a program that requires provision of RA in a proximity dependent paracrine fashion by RALDH2$^+$ LMC MNs, despite the expression of this enzyme in a subset of ES-MNs (FIG. 14E, 25C). The autonomy of the program leading to specification of diverse motor pool subtypes is further supported by experiments in which brachial MN progenitors were dissociated and mixed with excess number of cervical MN progenitors. Even under these ectopic conditions brachial MNs acquired both correct columnar and pool subtype identities closely matching those of undisturbed cultures.

Cellular Behaviors of ES-MNs In Vivo

The finding that ES-MNs acquire expression of LMC and MMC markers permitted the inventors to examine their subtype-specific functional properties. As nascent MNs exit the cell cycle they migrate and settle according to their columnar identity, in either the median or lateral motor column. In contrast, the cell bodies of ES-MNs expressing MMC and LMC markers do not cluster in a columnar arrangement within embryoid bodies (FIG. 25D), possibly due to the lack of appropriate migratory substrates and guidance cues. This view is supported by the finding that ES cell-derived MMC and LMC neurons segregate into appropriate columnar territories when implanted into the developing chick neural tube at the time of endogenous MN generation. The ability of transplanted cells to reach correct motor columns provides evidence that MNs can sense their position within the host neural tube and respond to column-specific migratory cues. Although FoxP1$^+$ ES-MNs settled in the proximity of the LMC column, they rarely invaded the host LMC territory. The clustering of MNs within the LMC appears to depend on complex combinatorial profile of surface adhesion molecules (Price et al., 2002). Mismatches in the surface properties of mouse and chick LMC neurons could therefore underlie their inefficient intermixing or clustering.

LMC and MMC ES-MNs can also make correct peripheral axon pathfinding choices—selecting axial and limb nerve branches with a fidelity that matches that of endogenous chick MNs in vivo. The fact that a subset of cervical ES-MNs projected axons along a limb nerve trajectory after grafting into brachial spinal cord is likely to reflect their HMC identity (FIG. 26D-I). In this context, findings here and conclusions differ from a previous report of the selectivity of axial projections of cervical ES-MNs (Soundararajan et al., 2006). The specificity of MN cell body migration and axonal projections suggests that the transcriptional program of ES-MNs regulates expression of essential guidance receptors needed for correct execution of complex cellular behaviors (Marquardt et al., 2005; Moret et al., 2007). The causal relationship between transcriptional identity of MNs and their axon guidance properties has been demonstrated for lateral and medial LMC neurons (Kania et al., 2000; Kania and Jessell, 2003), but it is less well characterized in the case of LMC and MMC divisions (Sharma et al., 1998; Sharma et al., 2000; Marquardt et al., 2005). It remains to be determined if individual ES-MN pools can target appropriate muscle groups in the developing limb. The xenotransplantation assay used in this study is unlikely to be optimal for this level of analysis, not least because of the profound divergence in anatomical and functional organization of the mouse forelimb and chick wing.

In conclusion, the findings here show that essential endogenous signals are recruited during the differentiation of ES cells to specify defined subsets of spinal MNs. The ability to generate MN subtypes characteristic of defined rostro-caudal levels of the spinal cord may prove beneficial for studies of mammalian neuronal diversity, and also for therapeutic approaches to disease modeling and regenerative medicine. Individual MN subtypes exhibit differential susceptibility to neurodegeneration in two MN diseases, Amyotrophic Lateral Sclerosis (ALS) and Spinal Muscular Atrophy (SMA). MNs in Onuf's nucleus and the oculomotor nucleus are selectively spared in ALS (Anneser et al., 1999; Vanselow and Keller, 2000). Similarly, MNs innervating distal limb muscles are comparatively resistant to degeneration in SMA (Murray et al., 2008).

REFERENCES

1. Agalliu, D., Takada, S., Agalliu, I., McMahon, A. P., and Jessell, T. M. (2009). Motor Neurons with Axial Muscle Projections Specified by Wnt4/5 Signaling. Neuron 61, 708-720.
2. Andersson, E., Tryggvason, U., Deng, Q., Friling, S., Alekseenko, Z., Robert, B., Perlmann, T., and Ericson, J. (2006). Identification of Intrinsic Determinants of Midbrain Dopamine Neurons. Cell 124, 393-405.
3. Anneser, J. M. H., Domenico Borasio, G., Berthele, A., Zieglgänsberger, W., and Tölle, T. R. (1999). Differential Expression of Group I Metabotropic Glutamate Receptors in Rat Spinal Cord Somatic and Autonomic Motoneurons: Possible Implications for the Pathogenesis of Amyotrophic Lateral Sclerosis. Neurobiology of Disease 6, 140-147.
4. Arber, S., Han, B., Mendelsohn, M., Smith, M., Jessell, T. M. and Sockanathan, S., (1999). Requirement for the homeobox gene Hb9 in the consolidation of motor neuron identity. Neuron 23, 659-674.
5. Arber, S., Ladle, D. R., Lin, J. H., Frank, E., and Jessell, T. M. (2000). ETS gene Er81 controls the formation of functional connections between group Ia sensory afferents and motor neurons. Cell 101, 485-498.
6. Bain, G., Kichens, D., Yao, M., Huettner, J. E., and Gottlieb, D. I. (1995). Embryonic stem cells express neuronal properties in vitro. Dev Biol. 168, 342-357.
7. Boillée, S., Vande Velde, C., and Cleveland, Don W. (2006). ALS: A Disease of Motor Neurons and Their Normeuronal Neighbors. Neuron 52, 39-59.
8. Briscoe, J. and Ericson, J., (2001). Specification of neuronal fates in the ventral neural tube. Curr. Opin. Neurobiol. 11, 43-49.
9. Briscoe, J. Pierani, A., Jessell, T. M., and Ericson, J. (2000). A homeodomain protein code specifies progenitor cell identity and neuronal fate in the ventral neural tube. Cell. 101, 435-445.
10. Buck, L., and Axel, R. (1991). A novel multigene family may encode odorant receptors: A molecular basis for odor recognition. Cell 65, 175-187.
11. D'Amour, K. A., Bang, A. G., Eliazer, S., Kelly, O. G., Agulnick, A. D., Smart, N. G., Moorman, M. A., Kroon, E., Carpenter, M. K., and Baetge, E. E. (2006). Production of pancreatic hormone-expressing endocrine cells from human embryonic stem cells. Nat Biotech 24, 1392-1401.
12. Dasen, J. S. (2009). Transcriptional networks in the early development of sensory-motor circuits. Curr Top Dev Biol 87, 119-148.
13. Dasen, J. S., De Camilli, A., Wang, B., Tucker, P. W., and Jessell, T. M. (2008). Hox Repertoires for Motor Neuron Diversity and Connectivity Gated by a Single Accessory Factor, FoxP1. Cell 134, 304-316.
14. Dasen, J. S., Liu, J. P. and Jessell, T. M. (2003). Motor neuron columnar fate imposed by sequential phases of Hox-c activity. Nature 425, 926-933.
15. Dasen, J. S., Tice, B. C., Brenner-Morton, S., and Jessell, T. M. (2005). A Hox regulatory network establishes motor neuron pool identity and target-muscle connectivity. Cell 123, 477-491.
16. Dauer, W., and Przedborski, S. (2003). Parkinson's Disease: Mechanisms and Models. Neuron 39, 889-909.
17. De la Cruz, C. C., Der-Avikian, A., Spyropoulos, D. D., Tieu, D. D., and Carpenter, E. M. (1999). Targeted disruption of Hoxd9 and Hoxd10 alters locomotor behavior, vertebral identity, and peripheral nervous system development. Dev Biol 216, 595-610.
18. Dessaud, E., McMahon, A. P., and Briscoe, J. (2008). Pattern formation in the vertebrate neural tube: a sonic hedgehog morphogen-regulated transcriptional network. Development 135, 2489-2503.

19. di Sanguinetto, S. A. D. T., Dasen, J. S., and Arber, S. (2008). Transcriptional mechanisms controlling motor neuron diversity and connectivity. Current Opinion in Neurobiology 18, 36-43.
20. Dimos, J. T., Rodolfa, K. T., Niakan, K. K., Weisenthal, L. M., Mitsumoto, H., Chung, W., Croft, G. F., Saphier, G., Leibel, R., Goland, R., et al. (2008). Induced Pluripotent Stem Cells Generated from Patients with ALS Can Be Differentiated into Motor Neurons. Science 321, 1218-1221.
21. Doone, V. G., Pelissier, N. Manchester, T., and Vizzard, A. M. (1999). Distribution of NADPH-d and nNOS-IR in the thoracolumbar and sacrococcygeal spinal cord of the guinea pig. J Auton Nery Syst 77, 98-113.
22. Ebert, A. D., Yu, J., Rose, F. F., Mattis, vs. B., Lorson, C. L., Thomson, J. A., and Svendsen, C. N. (2009). Induced pluripotent stem cells from a spinal muscular atrophy patient. Nature 457, 277-280.
23. Eiraku, M., Watanabe, K., Matsuo-Takasaki, M., Kawada, M., Yonemura, S., Matsumura, M., Wataya, T., Nishiyama, A., Muguruma, K., and Sasai, Y. (2008). Self-Organized Formation of Polarized Cortical Tissues from ESCs and Its Active Manipulation by Extrinsic Signals. Cell Stem Cell 3, 519-532.
24. Eisen J. S. (1992). The role of interactions in determining cell fate of two identified motorneurons in the embryonic zebrafish. Neuron 8, 231-240.
25. Gage, F. H. (2000). Mammalian neural stem cells. Science 287, 1433-1438.
26. Gaspard, N., Bouschet, T., Hourez, R., Dimidschstein, J., Naeije, G., van den Ameele, J., Espuny-Camacho, I., Herpoel, A., Passante, L., Schiffmann, S, N., et al. (2008). An intrinsic mechanism of corticogenesis from embryonic stem cells. Nature 455, 351-357.
27. Haase, G., Dessaud, E., Garces, A., de Bovis, B., Birling, M., Filippi, P., Schmalbruch, H., Arber, S., and deLapeyriere, O. (2002). GDNF acts through PEA3 to regulate cell body positioning and muscle innervations of specific motor neuron pools. Neuron 35, 893-905.
28. Hamburger, vs., and Hamilton, H. L. (1992). A series of normal stages in the development of the chick embryo. 1951. Dev Dyn 195, 231-272.
29. Harper J M, Krishnan C, Darman J S, Deshpande D M, Peck S, Shats I, Backovic S, Rothstein J D, and Kerr D A. (2004) Axonal growth of embryonic stem cell-derived motoneurons in vitro and in motoneuron-injured adult rats. Proc Natl Acad Sci USA. 101, 7123-7128.
30. Helmbacher, F., Dessaud, E., Arber, S., deLapeyriere, O., Henderson, C. E., Klein, R., and Maina, F. (2003). Met signaling is required for recruitment of motor neurons to PEA3-positive motor pools. Neuron 39, 767-777.
31. Hollyday, M. (1980). Motoneuron histogenesis and the development of limb innervations. Curr Top Dev Biol. 15 Pt 1, 181-215.
32. Hollyday, M. (1980). Organization of motor pools in the chick lumbar lateral motor column. J Comp Neurol 194, 143-70.
33. Hollyday, M., and Jacobson, R. D. (1990). Location of motor pools innervating chick wing. J Comp Neurol 302, 575-588.
34. Ikeda, H., Osakada, F., Watanabe, K., Mizuseki, K., Haraguchi, T., Miyoshi, H., Kamiya, D., Honda, Y., Sasai, N., Yoshimura, N., et al., (2005). Generation of Rx+/Pax6+ neural retinal precursors from embryonic stem cells. Proceedings of the National Academy of Sciences of the United States of America 102, 11331-11336.
35. Jessell, T. M. (2000) Neuronal specification in the spinal cord: inductive signals and transcriptional codes. Nat Rev Genet 1, 20-9.
36. Kania, A., and Jessell, T. M. (2003). Topographic motor projections in the limb imposed by LIM homeodomain protein regulation of ephrin-A:EphA interactions. Neuron 38, 581-596.
37. Kania, A., Johnson, R. L., and Jessell, T. M. (2000). Coordinate roles for LIM homeobox genes in directing the dorsoventral trajectory of motor axons in the vertebrate limb. Cell 102, 161-173.
38. Kawasaki, H., Mizuseki, K., Nishikawa, S., Kaneko, S., Kuwana, Y., Nakanishi, S., Nishikawa, S. I., and Sasai, Y. (2000). Induction of midbrain dopaminergic neurons from ES cells by stromal cell-derived inducing activity. Neuron. 28, 31-40.
39. Kiecker, C., and Niehrs, C. (2001). A morphogen gradient of Wnt/{beta}-catenin signalling regulates anteroposterior neural patterning in Xenopus. Development 128, 4189-4201.
40. Kubo, A., Shinozaki, K., Shannon, J. M., Kouskoff, vs., Kennedy, M., Woo, S., Fehling, H. J., and Keller, G. (2004). Development of definitive endoderm from embryonic stem cells in culture. Development 131, 1651-1662.
41. Kyba, M., Perlingeiro, R. C., and Daley, G. Q. (2002). HoxB4 confers definitive lymphoid-myeloid engraftment potential on embryonic stem cell and yolk sac hematopoietic progenitors. Cell 109, 29-37.
42. Lako, M., Lindsay, S., Lincoln, J., Cairns, P. M., Armstrong, L., and Hole, N. (2001). Characterisation of Wnt gene expression during the differentiation of murine embryonic stem cells in vitro: role of Wnt3 in enhancing haematopoietic differentiation. Mech Dev 103, 49-59.
43. Landmesser, L. (1978). The distribution of motoneurons supplying chick hind limb muscles. J Physiol 284, 371-389.
44. Landmesser, L. T. (1980). The generation of neuromuscular specificity. Annu Rev Neurosci 3, 279-302.
45. Landmesser, L. T. (2001). The acquisition of motoneuron subtype identity and motor circuit formation. Int J Dev Neurosci 19, 175-182.
46. Lee, H., Shamy, G. A., Elkabetz, Y., Schofield, C. M., Harrsion, N. L., Panagiotakos, G., Socci, N. D., Tabar, vs., and Studer, L. (2007). Directed differentiation and transplantation of human embryonic stem cell-derived motoneurons. Stem Cells 25, 1931-1939.
47. Lee, S. H., Lumelsky, N., Studer, L., Auerbach, J. M., and McKay, R. D. (2000). Efficient generation of midbrain and hindbrain neurons from mouse embryonic stem cells. Nat Biotechnol 18, 675-679.
48. Lee, S. K. and Pfaff, S. L. (2001). Transcriptional networks regulating neuronal identity in the developing spinal cord. Nat Neurosci 4 Suppl. 1183-1191.
49. Li, X. J., Du, Z. W., Zarnowska, E. D., Pankratz, M., Hansen, L. O., Pearce, R. A., and Zhang, S. C. (2005). Specification of motoneurons from human embryonic stem cells. Nat Biotechnol 23, 215-221.
50. Lin, A. W., and Carpenter, E. M. (2003). Hoxa10 and Hoxd10 coordinately regulate lumbar motor neuron patterning. J Neurobiol 56, 328-337.
51. Lin, J. H., Saito, T., Anderson, D. J., Lance-Jones, C., Jessell, T. M., and Arber, S. (1998). Functionally related motor neuron pool and muscle sensory afferent subtypes defined by coordinate ETS gene expression Cell 95, 393-407.

52. Liss, B., and Roeper, J. (2008). Individual dopamine midbrain neurons: Functional diversity and flexibility in health and disease. Brain Research Reviews 58, 314-321.
53. Liu, J. P. (2006). The function of growth/differentiation factor 11 (Gdf11) in rostro-caudal patterning of the developing spinal cord. Development 133, 2865-2874.
54. Liu, J. P., Laufer, E., and Jessell, T. M. (2001). Assigning the Positional Identity of Spinal Motor Neurons Rostrocaudal Patterning of Hox-c Expression by FGFs, Gdf11, and Retinoids. Neuron 32, 997-1012.
55. Livet, J., Sigrist, M., Stroebel, S., De Paola, vs., Price, S. R., Henderson, C. E., Jessell, T. M., and Arber, S. (2002). ETS gene Pea3 controls the central position and terminal arborization of specific motor neuron pools. Neuron 35, 877-892.
56. MacNeil, M. A., and Masland, R. H. (1998). Extreme Diversity among Amacrine Cells: Implications for Function. Neuron 20, 971-982.
57. Marquardt, T., Shirasaki, R., Ghosh, S., Andrews, S. E., Carter, N., Hunter, T., and Pfaff, S. L. (2005). Coexpressed EphA receptors and ephrin-A ligands mediate opposing actions on growth cone navigation from distinct membrane domains. Cell 121, 127-139.
58. Martinat, C., Bacci, J.-J., Leete, T., Kim, J., Vanti, W. B., Newman, A. H., Cha, J. H., Gether, U., Wang, H., and Abeliovich, A. (2006). Cooperative transcription activation by Nurr1 and Pitx3 induces embryonic stem cell maturation to the midbrain dopamine neuron phenotype. Proceedings of the National Academy of Sciences of the United States of America 103, 2874-2879.
59. Miles G B, Yohn D C, Wichterle H, Jessell T M, Rafuse V F, and Brownstone R M. (2004) Functional properties of motoneurons derived from mouse embryonic stem cells. J Neurosci. 8, 7848-7858.
60. Mizuguchi, R., Sugimori, M., Takebayashi, H., Kosako, H., Nagao, M., Yoshida, S., Nabeshima, Y., Shimamura, K., and Kakafuku, M. (2001). Combinatorial roles of olig2 and neurogenin2 in the coordinated induction of pan-neuronal and subtype-specific properties of motoneurons. Neuron 31, 757-771.
61. Mohammadi, M., Froum, S., Hamby, J. M., Schroeder, M. C., Panek, R. L., Lu, G. H., Eliseenkova, A. V., Green, D., Schlessinger, J., and Hubbard, S. R. (1998). Crystal structure of an angiogenesis inhibitor bound to the FGF receptor tyrosine kinase domain. Embo J 17, 5896-5904.
62. Moret, F., Renaudot, C., Bozon, M., and Castellani, vs. (2007). Semaphorin and neuropilin co-expression in motoneurons sets axon sensitivity to environmental semaphorin sources during motor axon pathfinding. Development 134, 4491-4501.
63. Muhr, J., Graziano, E., Wilson, S., Jessell, T. M., and Edlund, T. (1999). Convergent inductive signal specify midbrain, hindbrain, and spinal cord identity in gastrula stage chick embryos. Neuron 23, 689-702.
64. Munoz-Sanjuan, I. and Brivanlou, A. H. (2002). Neural induction, the default model and embryonic stem cells. Nat Rev Neurosci. 3, 271-280.
65. Murray, L. M., Comley, L. H., Thomson, D., Parkinson, N., Talbot, K., and Gillingwater, T. H. (2008). Selective vulnerability of motor neurons and dissociation of pre- and post-synaptic pathology at the neuromuscular junction in mouse models of spinal muscular atrophy. Hum Mol Genet 17, 949-962.
66. Murry, C. E., and Keller, G. (2008). Differentiation of Embryonic Stem Cells to Clinically Relevant Populations: Lessons from Embryonic Development. 132, 661-680.
67. Nordstrom, U., Maier, E., Jessell, T. M., and Edlund, T. (2006). An early role for WNT signaling in specifying neural patterns of Cdx and Hox gene expression and motor neuron subtype identity. PLoS Biol 4, e252.
68. Novitch, B. G. Wichterle, H., Jessell, T. M., and Sockanathan, S. (2003). A requirement for retinoic acid-mediated transcriptional activation in ventral neural patterning and motor neuron specification. Neuron 40, 81-95.
69. Park, I.-H., Arora, N., Huo, H., Maherali, N., Ahfeldt, T., Shimamura, A., Lensch, M. W., Cowan, C., Hochedlinger, K., and Daley, G. Q. (2008). Disease-Specific Induced Pluripotent Stem Cells. Cell 134, 877-886.
70. Price, S. R., De Marco Garcia, N. V., Ranscht, B., and Jessell, T. M. (202). Regulation of motor neuron pool sorting by differential expression of type II caherins. Cell 109, 205-216.
71. Renoncourt, Y., Caroll, P., Filippi, P., Arce, V., and Alonso, S. (1998). Neurons derived in vitro from ES cells express homeoproteins characteristic of motoneurons and interneurons. Mech Dev. 79, 185-197.
72. Rockhill, R. L., Daly, F. J., MacNeil, M. A., Brown, S. P., and Masland, R. H. (2002). The Diversity of Ganglion Cells in a Mammalian Retina. J Neurosci 22, 3831-3843.
73. Rosas, D. H., Salat, D. H., Lee, S. Y., Zaleta, A. K., Hevelone, N., and Hersch, S. M. (2008). Complexity and Heterogeneity: What Drives the Ever-changing Brain in Huntington's Disease? Annals of the New York Academy of Sciences 1147, 196-205.
74. Shaner, N. C., Campbell, R. E., Steinbach, P. A., Giepmans, B. N., Palmer, A. E., and Tsien, R. Y. (2004). Improved monomeric red, orange and yellow fluorescent proteins derived from *Discosoma* sp. Red fluorescent protein. Nat Biotechnol 22, 1567-1572.
75. Sharma, K., Leonard, A. E., Lettieri, K., and Pfaff, S. L. (2000). Genetic and epigenetic mechanisms contribute to motor neuron pathfinding. Nature 406, 515-519.
76. Sharma, K., Sheng, H. Z., Lettieri, K., Li, H., Karavanov, A., Potter, S., Westphal, H., and Pfaff, S. L. (1998). LIM homeodomain factors Lhx3 and Lhx4 assign subtype identities for motor neurons. Cell 95, 817-828.
77. Shin, S., Dalton, S., and Stice, S. L. (2005). Human motor neuron differentiation form human embryonic stem cells. Stem Cells Dev 14, 266-269.
78. Singh Roy, N., Nakano, T., Xuing, L., Kang, J., Nedergaard, M., and Goldman, S. A. (2005). Enhancer-specified FGP-based FACS purification of human spinal motor neurons from embryonic stem cells. Exp Neurol 196, 224-234.
79. Sockanathan, S., and Jessell, T. M. (1998). Motor neuron-derived retinoid signaling specifies the subtype identity of spinal motor neurons. Cell 94, 503-514.
80. Sockanathan, S., Perlamnn, T., and Jessell, T. M. (2003). Retinoid receptor signaling in postmitotic motor neurons regulates rostrocaudal positional identity and axonal projection patter. Neuron 40, 97-111.
81. Soldner, F., Hockemeyer, D., Beard, C., Gao, Q., Bell, G. W., Cook, E. G., Hargus, G., Blak, A., Cooper, O., Mitalipova, M., et al. (2009). Parkinson's Disease Patient-Derived Induced Pluripotent Stem Cells Free of Viral Reprogramming Factors. Cell 136, 964-977.
82. Soundararajan, P. Miles, G. B., Rubin, L. L., Brownstone, R. M., and Rafuse, V. F. (2006). Motorneurons derived from embryonic stem cells express transcription factors and develop phenotypes characteristic of medial motor column neurons. J Neurosci 26, 3256-3268.
83. Stpyridis, M. P., Lunn, J. S., Collins, B. J., and Storey, K. G. (2007). A discrete period of FGF-induced Erk1/2 signalling is required for vertebrate neural specification. Development 134, 2889-2894.

84. Su, H.-L., Muguruma, K., Matsuo-Takasaki, M., Kengaku, M., Watanabe, K., and Sasai, Y. (2006). Generation of cerebellar neuron precursors from embryonic stem cells. Developmental Biology 290, 287-296.
85. Takahashi, K., and Yamanaka, S. (2006). Induction of pluripotent stem cells from mouse embryonic and adult fibroblast cultures by defined factors. Cell 126, 663-676.
86. Tamura, S., Morikawa, Y., Iwanishi, H., Hisaoka, T., and Senba, E. (2003). Expression pattern of the winged-helix/forkhead transcription factor Foxp1 in the developing central nervous system. Gene Expr Patterns 3, 193-197.
87. ten Berge, D., Koole, W., Fuerer, C., Fish, M., Eroglu, E., and Nusse, R. (2008). Wnt Signaling Mediates Self-Organization and Axis Formation in Embryoid Bodies. Cell Stem Cell 3, 508-518.
88. Tropepe, V., Hitoshi, S., Sirard, C., Mak, T. W., Rossant, J., and van der Kooy, D., (2001). Direct neural fate specification from embryonic stem cells: a primitive mammalian neural stem cell stage acquired through a default mechanism. Neuron. 30, 65-78.
89. Tsuchida, T., Ensini, M., Morto, S. B., Baldassare, M., Edlund, T., Jessell, T. M., and Pfaff, S. L. (1994). Topographic organization of embryonic motor neurons defined by expression of LIM homeoboxygenes. Cell 79, 957-970.
90. Uchida, N., Buck, D. W., He, D., Reitsma, M. J., Masek, M., Phan, T. V., Tsukamoto, A. S., Gage, F. H., and Weissman, I. L. (2000). Direct isolation of human central nervous system stem cells. Proc Natl Acad Sci USA. 97, 14720-14725.
91. Vanselow, B. K., and Keller, B. U. (2000). Calcium dynamics and buffering in oculomotor neurones from mouse that are particularly resistant during amyotrophic lateral sclerosis (ALS)-related motoneurone disease. J Physiol 525, 433-445.
92. Wahba, G. M., Hostikka, S. L., and Carpenter, E. M. (2001). The paralogous Hox genes Hoxa10 and Hoxd10 interact to pattern the mouse hindlimb peripheral nervous system and skeleton. Dev Biol 231, 87-102.
93. Watanabe, K., Kamiya, D., Nishiyama, A., Katayama, T., Nozaki, S., Kawasaki, H., Watanabe, Y., Mizuseki, K., and Sasai, Y. (2005). Directed differentiation of telencephalic precursors from embryonic stem cells. Nat Neurosci 8, 288-296.
94. Wichterle, H., and Peljto, M. (2008). Differentiation of mouse embryonic stem cells to spinal motor neurons. In Current Protocols In Stem Cell Biology (John Wiley & Sons, Inc.).
95. Wichterle, H., Lieberam, I., Porter, J. and Jessell, T. (2002). Directed differentiation of embryonic stem cells into motor neurons. Cell 110, 385-397.
96. Wichterle, H., Peljto, M., and Nedelec, S. (2009). Xenotransplantation of Embryonic Stem Cell-Derived Motor Neurons into the Developing Chick Spinal Cord. In Stem Cells in Regenerative Medicine, pp. 171-183.
97. Williams, J. A., Guicherit, O. M., Zaharian, B. I., Xu, Y., Chai, L., Wichterle, H., Kon, C., Gatchalian, C., Porter, J. A., Rubin, L. L., et al. (2003). Identification of a small molecule inhibitor of the hedgehog signaling pathway: effects on "basal" cell carcinoma-like lesions. Proc Natl Acad Sci USA 100, 4616-4621.
98. Yan, Y., Yang, D., Zarnowska, E. D., Du, Z., Werbel, B., Valliere, C., Pearce, R. A., Thomson, J. A., and Zhang, S.-C. (2005). Directed Differentiation of Dopaminergic Neuronal Subtypes from Human Embryonic Stem Cells. Stem Cells 23, 781-790.
99. Ying, Q. L., Stpyridis, M., Griffiths, D., Li, M., and Smith, A. (2003). Conversion of embryonic stem cells into neuroectodermal precursors in adherent monoculture. Nat Biotechnol 21, 183-186.
100. Zhou, Q., and Anderson, D. J. (2002). The bHLH transcription factors OLIG2 and LIG1 couple neuronal and glial subtype specification. Cell 109, 61-73.

What is claimed is:

1. A method for producing a caudal brachial motor neuron from an embryonic stem cell, comprising
   a) culturing the embryonic stem cell in a composition essentially free of any retinoid and comprising Advanced Dulbecco's Modified Eagle's Medium/F12 and Neurobasal medium that has been supplemented with 10% Knockout-Serum Replacement (ADFNK medium) wherein the amount of the composition is effective to generate the caudal brachial motor neuron under conditions such that the caudal brachial motor neuron is produced, and
   b) recovering the caudal brachial motor neuron so produced.

2. The method of claim 1, wherein during culturing the embryonic stem cell is contacted with at least one neurotrophic factor.

3. The method of claim 1, wherein the embryonic stem cell is a murine embryonic stem cell.

4. The method of claim 1, wherein the embryonic stem cell is a human embryonic stem cell.

5. The method of claim 1, wherein the caudal brachial motor neuron is transfected so that it expresses enhanced green fluorescent protein (eGFP).

6. The method of claim 1, wherein the culturing is effected in vivo in a subject.

7. The method of claim 1, wherein the culturing is effected in vitro.

8. A method for producing a caudal motor neuron comprising
   a) culturing an embryonic stem cell in a serum-free neural induction composition which is essentially free of any retinoid and comprises an isotonic salt solution, wherein the amount of the composition is effective to generate the caudal motor neuron under condition such that the caudal motor neuron is produced, and
   b) recovering the caudal motor neuron so produced.

9. The method of claim 8, wherein during culturing the embryonic stem cell is contacted with at least one neurotrophic factor.

10. The method of claim 8, wherein the embryonic stem cell is a murine embryonic stem cell.

11. The method of claim 8, wherein the embryonic stem cell is a human embryonic stem cell.

12. The method of claim 8, wherein the caudal motor neuron is transfected so that it expresses enhanced green fluorescent protein (eGFP).

13. The method of claim 8, wherein the culturing is effected in vivo in a subject.

14. The method of claim 8, wherein the culturing is effected in vitro.

15. The method of claim 8, wherein composition further comprises an amount of Fibroblast Growth Factor-2 (FGF-2).

16. The method of claim 8, wherein composition further comprises an amount of Growth differentiation factor 11 (Gdf11).

17. The method of claim 8, wherein composition further comprises an amount of a Wnt factor.

18. The method of claim 8, wherein composition further comprises an amount of Fibroblast Growth Factor-2 (FGF-2), an amount of Growth differentiation factor 11 (Gdf11), and an amount of a Wnt factor.

* * * * *